United States Patent
Dean

(10) Patent No.: US 11,222,722 B2
(45) Date of Patent: Jan. 11, 2022

(54) SYSTEMS AND METHODS FOR DYNAMIC DENTAL TREATMENT PLANS

(71) Applicant: FLEX DENTAL SOLUTIONS, LLC, Rancho Santa Fe, CA (US)

(72) Inventor: Brennon Dean, Rancho Santa Fe, CA (US)

(73) Assignee: FLEX DENTAL SOLUTIONS, LLC, Rancho Santa Fe, CA (US)

( * ) Notice: Subject to any disclaimer, the term of this patent is extended or adjusted under 35 U.S.C. 154(b) by 0 days.

(21) Appl. No.: 16/950,599

(22) Filed: Nov. 17, 2020

(65) Prior Publication Data

US 2021/0151172 A1 May 20, 2021

Related U.S. Application Data

(60) Provisional application No. 62/937,020, filed on Nov. 18, 2019.

(51) Int. Cl.
*G16H 20/00* (2018.01)
*G06Q 10/10* (2012.01)
(Continued)

(52) U.S. Cl.
CPC ............ *G16H 40/20* (2018.01); *G06F 16/27* (2019.01); *G06F 16/9566* (2019.01);
(Continued)

(58) Field of Classification Search
CPC ........ G16H 40/20; G16H 10/60; G16H 70/20; G16H 10/20; G16H 20/00; G06Q 40/02;
(Continued)

(56) References Cited

U.S. PATENT DOCUMENTS 8,572,576 B2 * 10/2013 Elvanoglu ............... G06F 9/543
717/127
8,688,474 B2 * 4/2014 Walter ................... G16H 40/20
705/3
(Continued)

OTHER PUBLICATIONS

YAPI. Paperless Dental Software—promotional materials available to the public as of Jan. 18, 2019, retrieved via Internet Archive on Jan. 4, 2021. 17 pages. (Year: 2019).*
(Continued)

*Primary Examiner* — Amy M Levy
(74) *Attorney, Agent, or Firm* — Sheppard, Mullin, Richter & Hampton LLP

(57) ABSTRACT

System and methods are disclosure herein for a web-based platform that provides dynamic creation and control of dental treatment plans, and other data that may be related to a dental patient. The disclose platform allows for seamless integration with many existing practice management systems (PMS). Furthermore, the web-based platform can be accessed in order to control the scheduling, accounting, and charting related to treatment planning for patients. The web-based platform provides various dynamic features, which can be customized to be specific to the patient, such as dynamic forms and specific payment options. Moreover, various features of the web-based platform are updated and synchronized in real-time. The web-based platform is particularly configured to provide automations, synchronization, and interactions with patients in a manner that reduces the risks and time consumed by traditional systems currently used in the dental field.

20 Claims, 86 Drawing Sheets

(51) Int. Cl.

| | |
|---|---|
| *G16H 70/20* | (2018.01) |
| *G06Q 20/40* | (2012.01) |
| *G06F 16/27* | (2019.01) |
| *H04L 29/06* | (2006.01) |
| *H04L 29/08* | (2006.01) |
| *G16H 10/60* | (2018.01) |
| *H04L 12/58* | (2006.01) |
| *G16H 40/20* | (2018.01) |
| *G16H 10/20* | (2018.01) |
| *G06Q 40/02* | (2012.01) |
| *G06F 16/955* | (2019.01) |
| *G06F 3/0482* | (2013.01) |
| *H04W 4/14* | (2009.01) |

(52) U.S. Cl.
CPC ......... *G06Q 10/107* (2013.01); *G06Q 20/405* (2013.01); *G06Q 40/02* (2013.01); *G16H 10/20* (2018.01); *G16H 10/60* (2018.01); *G16H 20/00* (2018.01); *G16H 70/20* (2018.01); *H04L 63/0853* (2013.01); *H04L 67/02* (2013.01); *H04L 67/10* (2013.01); *G06F 3/0482* (2013.01); *H04L 51/08* (2013.01); *H04L 51/22* (2013.01); *H04W 4/14* (2013.01)

(58) Field of Classification Search
CPC .... G06Q 10/107; G06Q 20/405; G06F 16/27; G06F 16/9566; G06F 3/0482; H04L 63/0853; H04L 67/02; H04L 67/10; H04L 51/08; H04L 51/22; H04L 67/12; H04L 63/0807; H04L 51/18; H04W 4/14; H04W 4/12

See application file for complete search history.

(56) References Cited

U.S. PATENT DOCUMENTS

| | | | |
|---|---|---|---|
| 8,930,219 B2* | 1/2015 | Trosien | G16H 20/30 705/3 |
| 2002/0007284 A1* | 1/2002 | Schurenberg | H04L 67/10 705/2 |
| 2007/0226005 A1* | 9/2007 | Smith | G16H 40/67 705/2 |
| 2007/0239488 A1* | 10/2007 | DeRosso | G16H 10/60 705/3 |
| 2010/0020967 A1* | 1/2010 | Kailash | H04L 63/08 380/45 |
| 2010/0145726 A1* | 6/2010 | Duke | G16H 50/20 705/3 |
| 2011/0054944 A1* | 3/2011 | Sandberg | G06Q 30/04 705/3 |
| 2012/0016792 A1* | 1/2012 | Fontenot | G06Q 40/00 705/38 |
| 2012/0065985 A1* | 3/2012 | Royal | G16H 10/60 705/2 |
| 2012/0239560 A1* | 9/2012 | Pourfallah | G06Q 40/08 705/40 |
| 2014/0006055 A1* | 1/2014 | Seraly | G06Q 10/10 705/3 |
| 2014/0047513 A1* | 2/2014 | van 't Noordende | H04L 63/0823 726/4 |
| 2014/0081667 A1* | 3/2014 | Joao | G06Q 10/10 705/3 |
| 2014/0372269 A1* | 12/2014 | Ternan | G06Q 40/00 705/35 |
| 2015/0193872 A1* | 7/2015 | Ivanoff | G16H 50/20 705/38 |
| 2015/0363563 A1* | 12/2015 | Hallwachs | H04B 5/0062 705/3 |
| 2016/0124920 A1* | 5/2016 | Golay | G06F 40/14 705/3 |
| 2016/0147944 A1* | 5/2016 | Douglass | G06F 21/6245 705/51 |
| 2016/0210424 A1* | 7/2016 | Di Battista | G06Q 10/0631 |
| 2017/0161439 A1* | 6/2017 | Raduchel | G06Q 10/063 |
| 2017/0177800 A1* | 6/2017 | Fuhrmann | H04L 51/046 |
| 2017/0228501 A1* | 8/2017 | Turner, Jr. | H04L 67/18 |
| 2018/0039733 A1* | 2/2018 | Golay | A61B 6/14 |
| 2018/0197636 A1* | 7/2018 | Firminger | A61B 5/4836 |
| 2019/0156928 A1* | 5/2019 | Chen | H04W 12/06 |
| 2019/0333622 A1* | 10/2019 | Levin | A61C 7/10 |
| 2019/0333644 A1* | 10/2019 | Lamarre | G16H 50/50 |
| 2021/0151147 A1* | 5/2021 | Dempers | H04L 9/12 |

OTHER PUBLICATIONS

Open Dental Version and partner information; retrieved from [https://www.opendental.com] on [Jan. 4, 2021]. 28 pages. (Year: 2021).*

Open Dental Manual 17.4—Treatment Plan module information. Version available to the public May 4, 2018. Retrieved from [https://www.opendental.com] and Internet Archive on [Jan. 4, 2021]. 10 pages. (Year: 2018).*

Open Dental Manual 17.4—Patient Portal, Web Forms, Web Scheduling information. Version available to the public May 4, 2018. Retrieved from [https://www.opendental.com] and Internet Archive on [Jan. 4, 2021]. 42 pages. (Year: 2018).*

Sybase Inc. "Relational database concepts" © 2000. Retrieved from [https://www.upi.pr.it/docs/easfg/easvrfgp7.htm] on [Aug. 24, 2021]. 4 pages. (Year: 2000).*

* cited by examiner

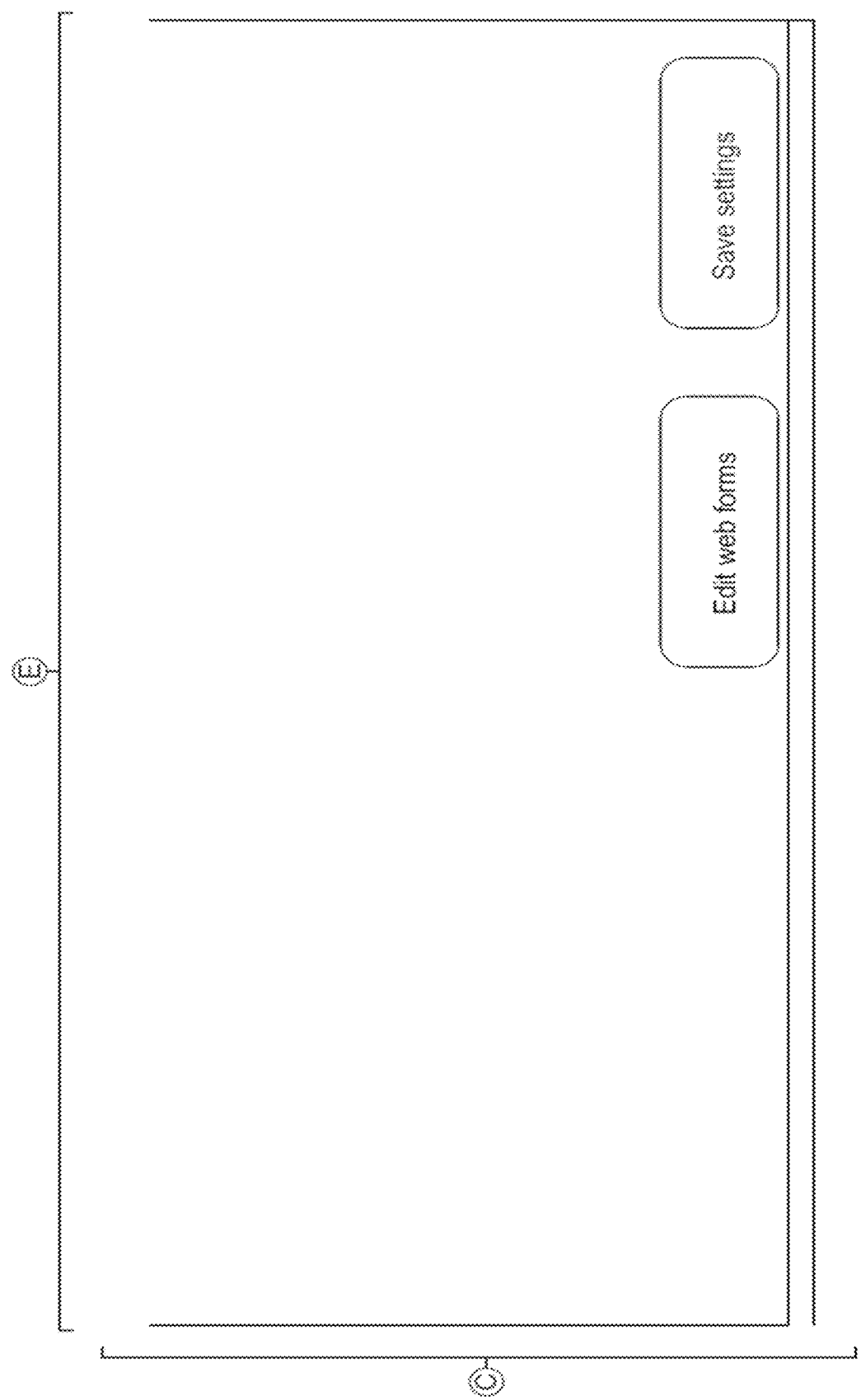

Informed Consent for Filling(s)

I understand that by signing below I am authorizing the procedure(s) including the possible risks and complications of the chosen the

Fillings:

Fillings are used to protect a sensitive surface of the tooth, to replace structure.

I understand that care must be exercised in chewing after the more extensive filling than originally diagnosed may be required due be sensitivity of the teeth that can last for a short period of time. If the FIG. 29 (Continued)

to be performed and I have read and understand the entirety of this form, procedure(s) and the available alternatives.

tooth structure, relive pain, cover an eroded area and fill in a hole or space in the tooth placement of fillings, especially during the first 24 hours, to avoid breakage. I understand that a to additional decay or fractures present at the time of treatment. Following a filling, there may sensitivity continues. I will notify my dentist as this can be a sign of more serious problems.

FIG. 29 (Continued)

During the preparation for a filling, the removal of tooth structure may possible abscess often indicate that the pulp did not heal. If that is masticatory (chewing) pressures or other traumatic forces, it is material to te tooth structure can also fail resulting in leakage and I understand that delaying treatment may cause harm, the dental creating additional treatment and associated expenses

Anesthesia:

In connection with my dental work, local anesthetic may be used for p
These include, but are not limited to, swelling, bruising, soreness, etc
the lip, tongue or cheek. Partial or complete numbness may linger aft
may be permanent.

FIG. 29 (Continued)

lead to exposure or trauma to underlying nerve or pulp issue. Extreme sensitivity or the case, a root canal treatment or extraction may be required. Because of extreme possible for fillings to become dislodged or fracture. The resin-enamel bond that adheres the filling recurrent decay.

disease may progress, further damage to teeth may occur and swelling and infection may occur ain control during dental procedures. All anesthetics create risks and possible side effects. vated blood pressure or pulse, allergic reaction and altered sensation that may lead to biting er the dental appointment. In rare cases, it can last for an extended time and occasionally FIG. 29 (Continued)

The following teeth or surfaces are the subject of the consent written above.

18 MOD

Name: Mike Foster

Date: 11-10-2019

| 15, 16 | D2740 | All Ceramic Crown | $2961.00 |
| 18-MOD | D2393 | resin-based composite - three surfaces, posterior | |

Treatment total: $7202.13
Current balance: ($148.04)
Office discount: $10015.09
Your total: $10015.09
Amount due now:

Pay In Advance
Receive a discount of by paying for your treatment in fully today
$9874.44
(5% discount)
choose this Patient name: Mike Foster
Signed by: Mike Foster
Date: 7/30/2020

SYSTEMS AND METHODS FOR DYNAMIC DENTAL TREATMENT PLANS

RELATED APPLICATION

This application claims the benefit of U.S. Provisional Patent Application No. 62/937,020, filed on Nov. 18, 2019, the contents of which are incorporated herein by reference in their entirety.

TECHNICAL FIELD

The present disclosure relates generally to systems and methods for dynamic creation and control of dental treatment plans, and related data. More specifically, systems and methods are disclosed that provide an application-based platform, allowing integration of practice management systems (PMS) and patient interactions.

DESCRIPTION OF RELATED ART

A patient's medical or dental written record can be a collection of all relevant data relating to the patient's personal, medical and dental information, which may be further utilized in order to provide proper diagnosis and treatment. This patient data is required to be properly maintained and managed as records. However, vast amounts of data can be amassed related to patients, especially in the case of larger dental practices. Management and dissemination of such large volumes of data has led to efforts in the medical and dental professions to manage patient data with a computer rather than in handwritten form.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

FIG. 69 depicts an example of a treatment plan including payment options that may be generated by the web-based platform as displayed on a patient device, according to one or more embodiments shown and described herein.

Figure 1:
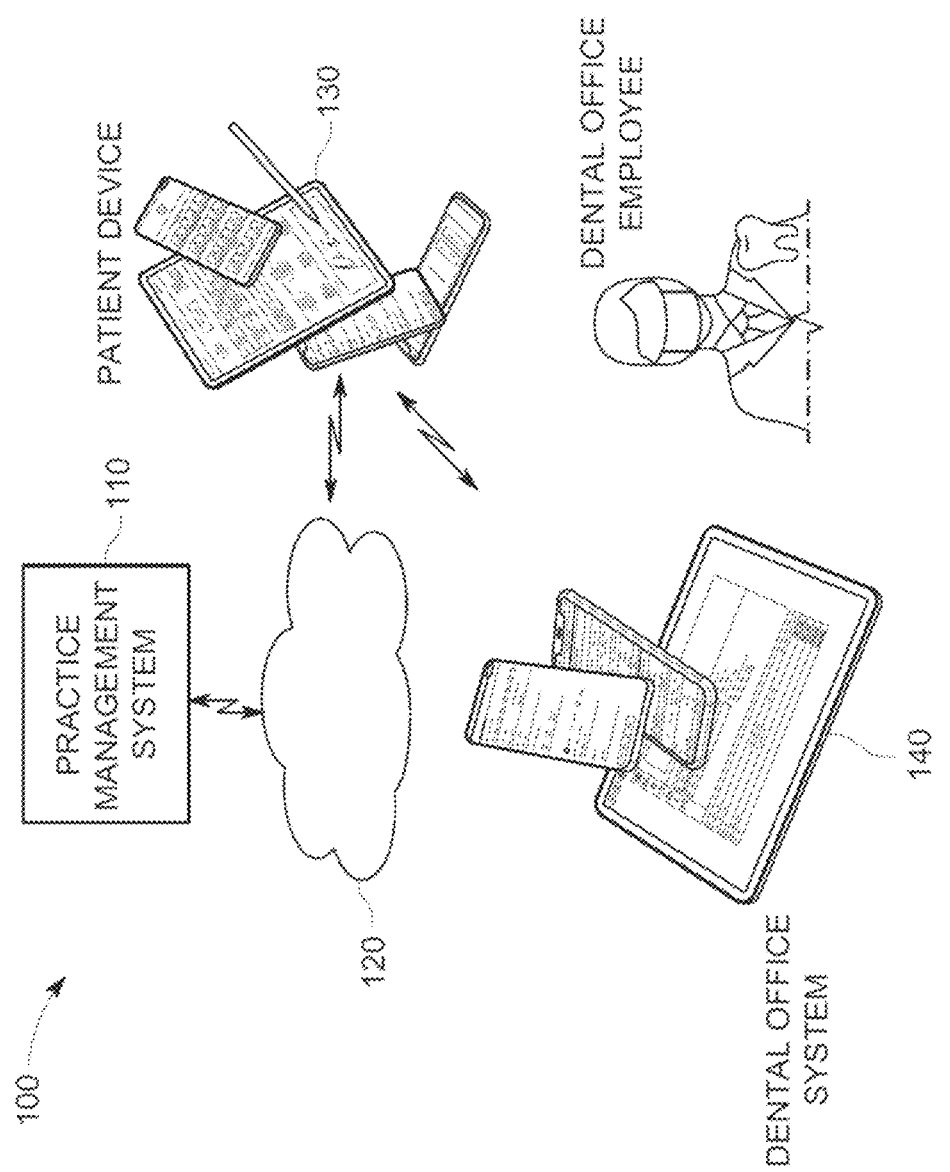
FIG. 1 illustrates an example of a communication system in which embodiments disclosed herein may be implemented for providing a web-based platform, according to one or more embodiments shown and described herein.

The figures are not exhaustive and do not limit the present disclosure to the precise form disclosed.

BRIEF SUMMARY OF THE DISCLOSURE

System and methods are disclosure herein for a web-based platform that includes a practice management system (PMS), a first computer device associated with a with a patient; and a second computer device associated with a medical office and communicatively connected to the PMS and to the first computer device via a distributed network. The second device of the platform being programed to create a treatment plan corresponding to the patient, wherein creating the treatment plan comprises dynamically adjusting the treatment plan based on selections entered into the second device and based on data received from the first device. The second device also programmed to create one or more payment options corresponding to the treatment plan, wherein creating the one or more payment options comprises dynamically adjusting the one or more payments options based on additional selections entered into the second device and based on additional data received from the first device. Additionally, the second device of the platform is programmed to synchronize the created treatment plan and the created one or more payment options with the PMS in real-time.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

DETAILED DESCRIPTION

The systems and techniques disclosed herein relate to a web-based platform that provides dynamic creation and control of dental treatment plans, and other data that may be related to a dental patient (or dental office, such as financial data, and identification data). The disclosed platform can be considered an adjunct service, allowing seamless integration with many existing practice management systems (PMS). The web-based platform also provides a collection of integrated tools that pair seamlessly to a PMS, such as Open Dental™. Moreover, the web-based platform is customizable. That is, the platform's design allows for a flexibility, where the features can be adapted for optimal use in a particular operational environment (e.g., dental office, primary care office, and the like). Moreover, due to the platform being web-based (e.g., accessible via a web browser), its features can run on various types of devices.

Furthermore, the web-based platform provides a plurality of dynamic features that can be customized to be specific to a specific user, namely a patient. For example, the web-based platform can dynamically adjust a treatment plan to only present payment options that are available to that particular patient. Moreover, various features of the web-based platform can update and synchronize data in real-time. The web-based platform is particularly configured to provide automation, synchronization, and interactions between the PMS, patients (via their user devices), and the platform itself, in a manner that reduces security risks (e.g., patient data is not permanently stored by the web-based platform) and eliminates the time consumed using many traditional systems in the dental field (e.g., manually managing records, forms, and payments).

FIG. 1 illustrates an example communication environment 100 in which embodiments of the web-based platform (or web-based platform), as disclosed herein, may be implemented. As used herein, the term "platform" can refer to a group of technologies functioning together to perform various tasks, including at least a major piece of software (e.g., Operating System), smaller application programs, and a set of compatible hardware devices on which the software applications can be run. The web-based platform may provide a plurality of features that can be accessed and interacted with by a user, such as a dental office employee, via a computer system 140, also referred to as a dental office system. As a general description, the features provided by the web-based platform can include, but are not limited to:

dynamic creation of treatment plans automated patient communications (e.g., confirmations, e-mail blasts, unscheduled treatment reminders, review requests, etc.)

dynamic creation of data forms (e.g., intake forms, medical forms, etc.)

integrated treatment payment (e.g., pay in-office through treatment plans, send customized statements to patients via text or e-mail)

integration and real-time synchronization with PMS (e.g., automatic import, log, update, and synch with PMS)

dynamic customization of forms, treatment plans, and patient communications (e.g., dynamically adjust contents to be specific to intended patient)

phone integrations (e.g., automatically display patient's info during an active call, and automatically log key call details)

automated consent forms (e.g., electronic consent forms, automatically link consent forms to procedure codes to track patient completion)

automated scheduling (e.g., optimized and customizable real-time scheduling and/or booking)

two way text messaging (two way SMS capabilities to send text messages to patients and receive text messages and inbound picture messages from patients)

instant photo capture (e.g., use photo-enabled devices to capture photos of patients, ID cards, EOBs, handwritten notes, images updated and stored to PMS)

intraoffice messaging (e.g., support chat messaging to various devices on the dental office system)

The computer system 140 may be a part of a larger system that can electronically store and transmit data throughout a medical practice, for example a dental office. In an example, the dental office employee can access the web-based platform via the computer system 140 (shown as a plethora of computer devices, including smartphones and tablet computers) to control the scheduling, accounting, and charting related to treatment planning for patients. The web-based platform is particularly configured to provide automation, synchronization, and in a manner that reduces the risks and time consumed in traditional systems currently used in the dental field.

A network 120 may provide communication between the PMS 110, patient device 130, and the computer system 140. Patient device 130 is shown as at least one device from a plethora of mobile devices, particularly smartphones and tablet computers. Accordingly, the patient device 130 may use any number of wireless communication protocols such as: WIFI, BLUETOOTH, ZIGBEE, cellular based protocols, and the like.

Examples of the network 120 may include, but are not limited to: an Internet Protocol (IP) or non-IP-based local area network (LAN); wireless LAN (WLAN); personal area network (PAN); machine-to-machine networks (M2M); metropolitan area network (MAN); wide area network (WAN); a cellular communication network; and the Internet. Communication over the network 120 may be performed in accordance with various communication protocols such as, but not limited to: Transmission Control Protocol and Internet Protocol (TCP/IP); User Datagram Protocol (UDP); IEEE 802.11; and cellular communication protocols over communication links 108. The communication links 108 may be enabled via a wired (e.g., copper, optical communication, etc.) or wireless (e.g., Wi-Fi®, cellular communication, satellite communication, Bluetooth® communication technologies. In some examples, the network 120 may be enabled via private communication links including, but not limited to: communication links established via Bluetooth®; cellular communication; optical communication; radio frequency communication; and the like. In some implementations, network 120 may comprise a wired link, or physical medium that interconnects the PMS 110, patient device 130, and the computer system 140.

Patient Device 130 can be any of a plurality of computer devices which are capable of being communicatively connected to the dental office system 140 and the Internet, and run the software applications implementing the features of the platform. For example, the patient device 130 can be a smartphone, a tablet computer, a laptop computer, a workstation, a local or remote server, or a wearable device such as a smartwatch. Additionally, patient device 130 and computer system 140 can utilize software applications that implement the user interfaces (UI) and user experience (UX) environments of the web-based platforms to allow a user to access, view, and interact with content from distributed computer networks, such as the Internet, and locally available information from local networks or individual computers and devices (e.g., computer, phone, etc.).

As alluded to above, the web-based platform provides various features and functions related to an efficient and secure control (and dissemination) of medical and/or dental data. For example, the web-based platform allows users related to the dental practice, such as dental professionals, as well as dental patients to interact with the system vis-à-vis a plethora of graphical user interfaces (GUIs) other interactive elements. Now referring to FIG. 2, an example of a sign-in screen 200 that may be displayed by the web-based platform is illustrated. As shown, the sign-in screen 200 can include entries for credentials allowing an authorized user, such as dental office employee, to access the system. In the illustrated example of FIG. 2, credentials include a username (e.g., administrator, employee, authorized user) and password.

Figure 2:
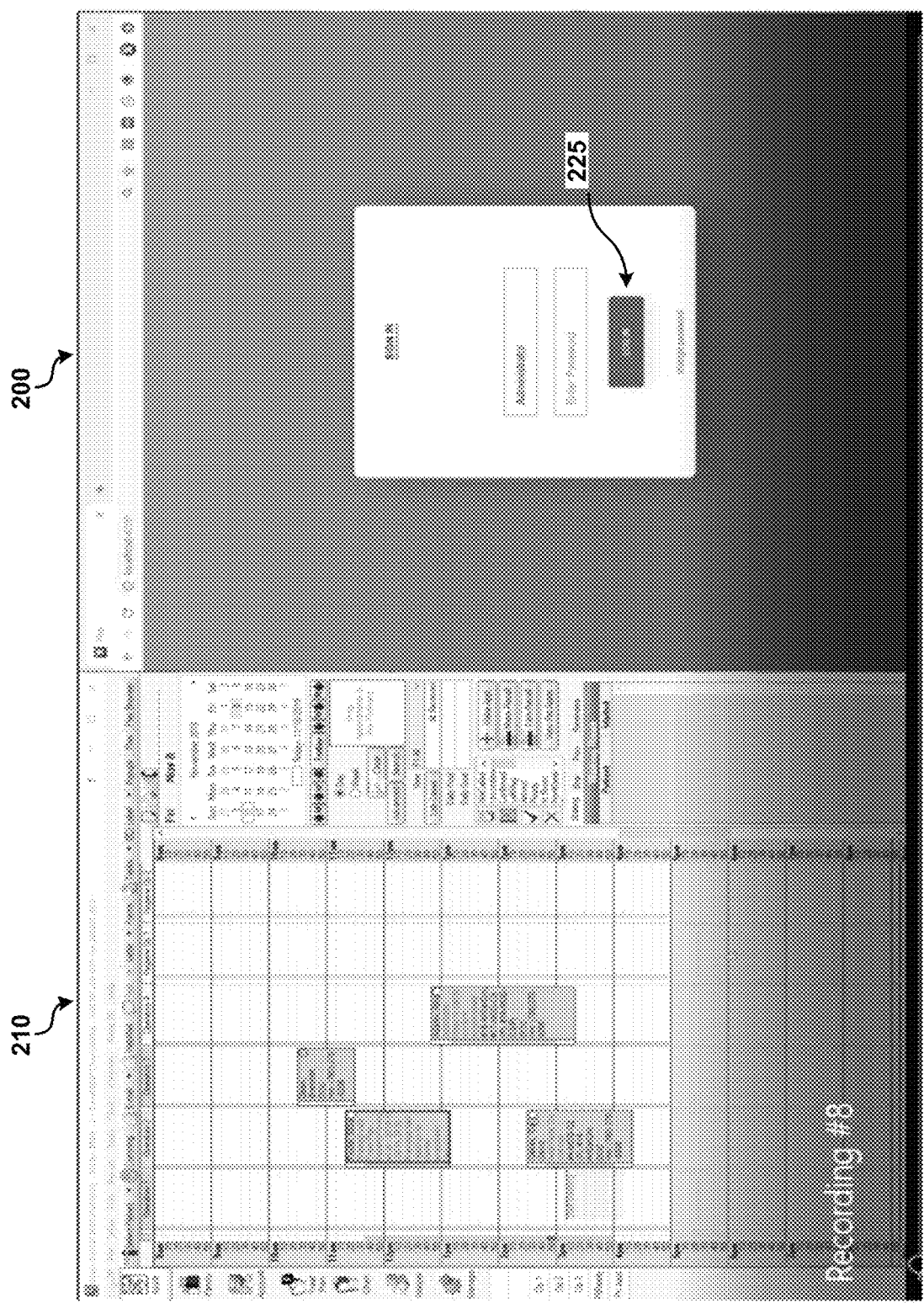
FIG. 2 illustrates an example of a displayed sign-in screen from the web-based platform and an interface associated with a practice management system (PMS), according to one or more embodiments shown and described herein.

Also, in FIG. 2, another screen 210 that may be associated with a PMS, such as Open Dental™, is shown next to the sign-in screen 220 (e.g., left side of screen) in a split-screen manner for purposes of illustration. In some cases, the sign-in screen 200 is the initial screen that is displayed by the web-based platform, prior to a user (e.g., dental office employee) gaining access to data and other features supported by the application. For example, after a user enters proper credentials, and then clicks the "log in" button 225, the user's credentials are authenticated, and subsequent screens which enable access and/or interaction with the various features of the web-based platform are presented for interaction.

Figure 3:
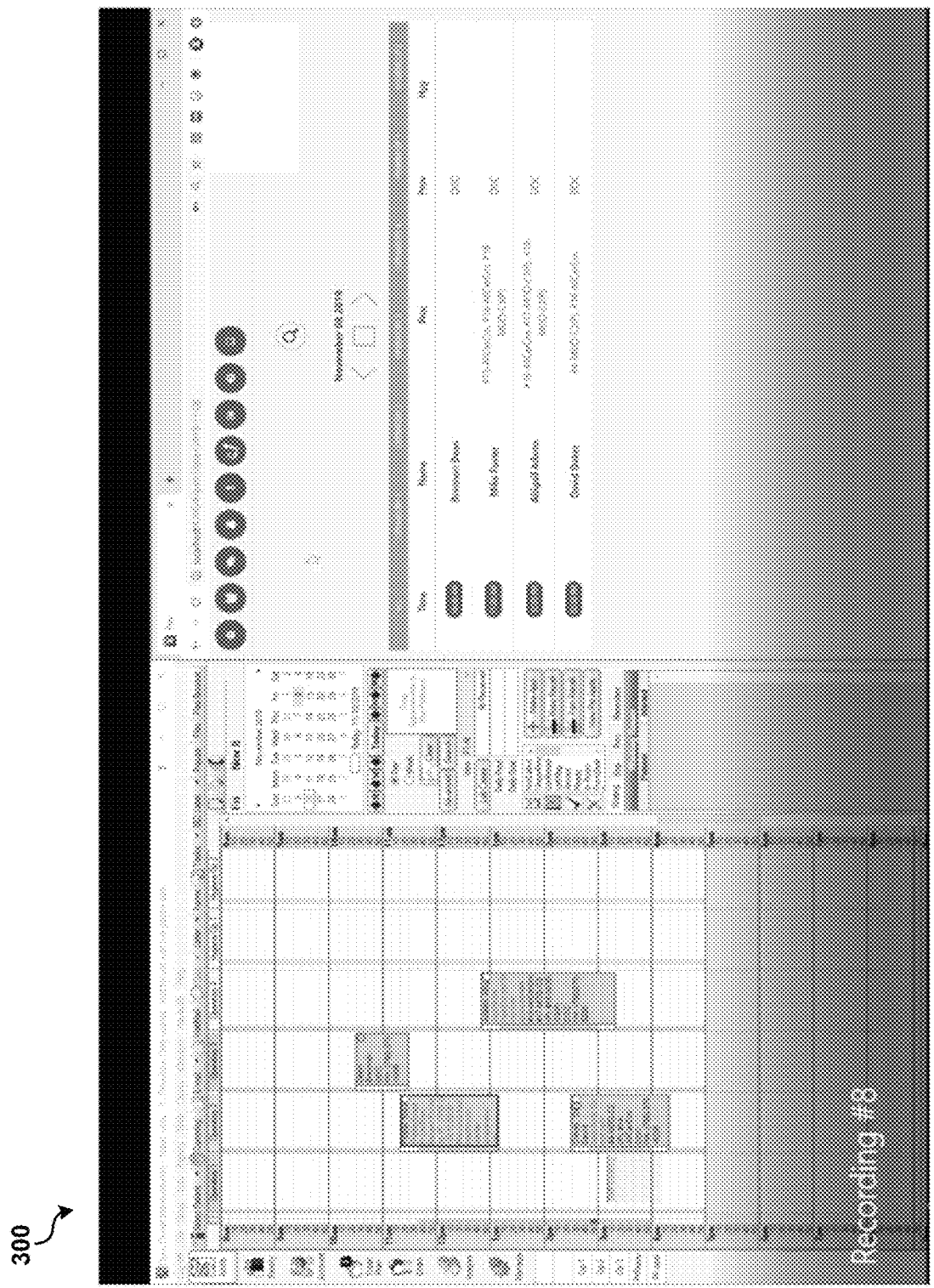
FIGS. 3-5 illustrate examples of displayed screens from the web-based platform associated with an implemented patient record feature, according to one or more embodiments shown and described herein.

FIG. 3 depicts an example of a screen 300 that displays multiple patients that are entered into the system is illustrated. In this screen, a patient schedule for a day "Nov. 8, 2019" is displayed. In the illustrated example, the dental office has four patients having appointments scheduled for that day, which is indicated in the screen by a patient's name, for instance, "Brennon Dean" being visibly listed. Corresponding data for the patient schedule displayed in screen 300, is also shown in PMS portion of the split-screen, illustrating the synchronicity of patients with the web-based platform. In other words, the same patients/patient schedule is visible in PMS and the web-based platform when accessing the same day in both platforms. Patients in the system can be updated in real-time. As an example, when new appointments are added to the PMS, the data is synchronized with the web-based platform in real-time and added to the displayed patient screen. Similarly, updates that made in the web-based platform are synchronized back with the PMS.

Figure 4:
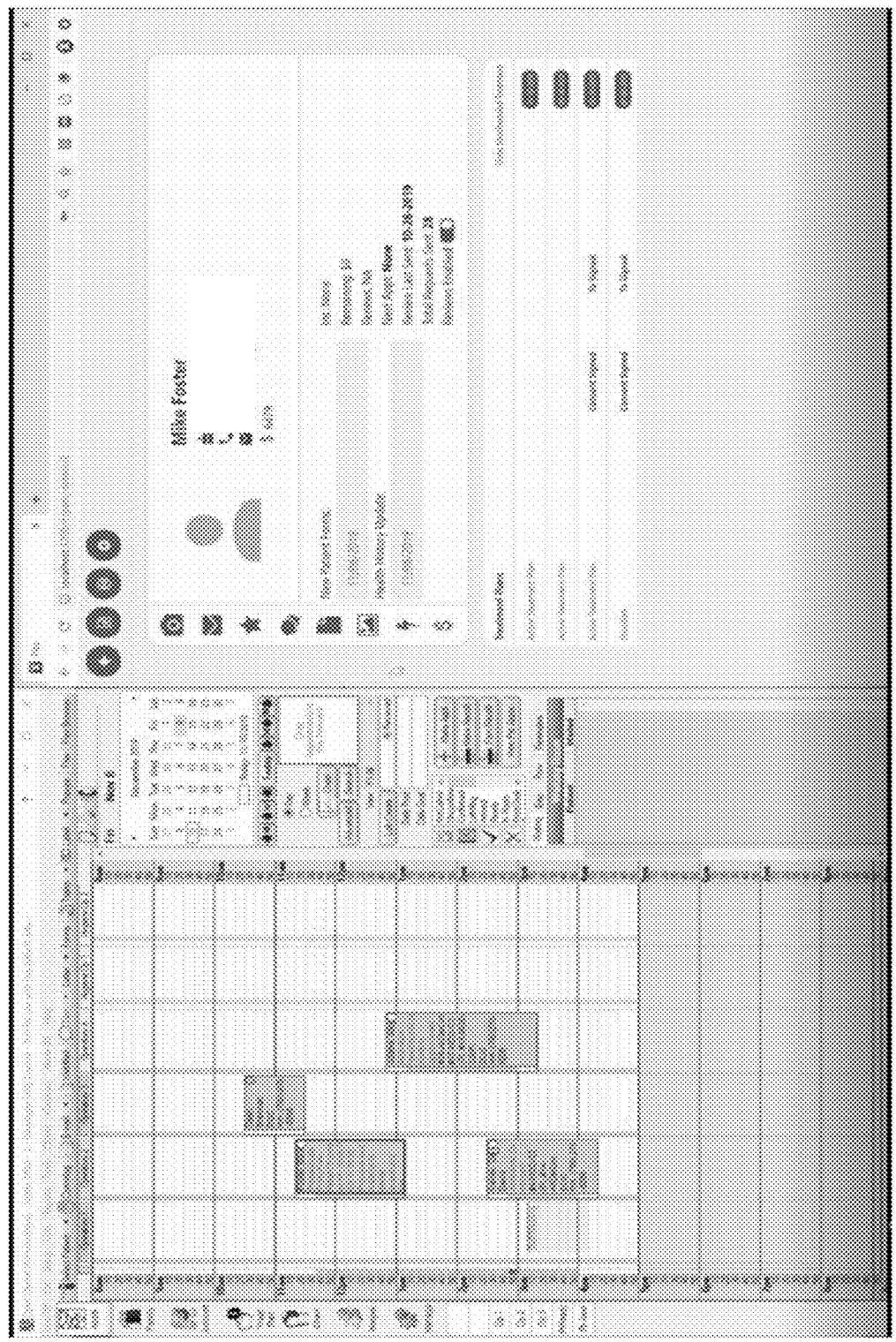

Clicking an appointment in screen 300 can result in opening a landing page for that specific patient. In FIG. 4, an example of a screen 400 is shown that displays a landing page. As seen in FIG. 4, the landing page corresponds to patient "Mike Foster," who is among the patients listed in the previous screen (shown in FIG. 3) displaying the patient schedule. For example, the web-based platform will display FIG. 4 as a result of a user clicking specifically on the name "Mike Foster" while viewing the patient schedule screen.

Figure 5:
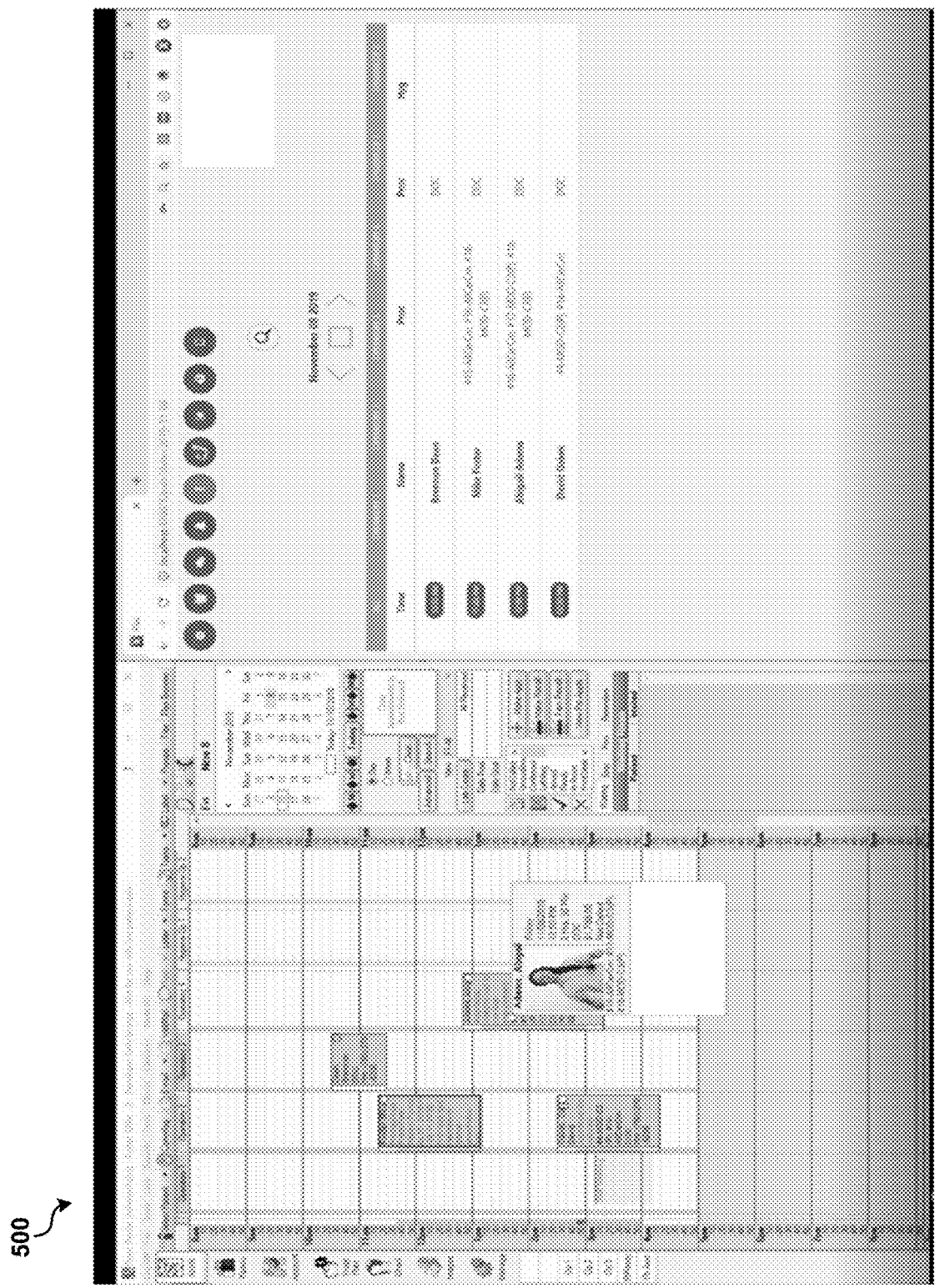

The data in FIG. 4 generally includes data for identifying the patient and described details of the appointment. Patient relevant information, such as photos of the patient, can be entered screen 400. Data entered into screen 400 integrates back to PMS, thereby updating the patient's record. Particularly, entering data into the landing page for "Mike Foster" in screen 400, would result in updating Mike Foster's record in the PMS shown in the opposing side of the split-screen. Additionally, pics of related documents for the patient, such as insurance cards, can be included into the patient record for that particular patient vis-à-vis the landing page in screen 400. FIG. 5 shows an example of an expanded patient record. The expanded patient record, displaying the patient's photo and other related data, can be displayed after clicking/hovering over that record in the PMS.

Figure 6:
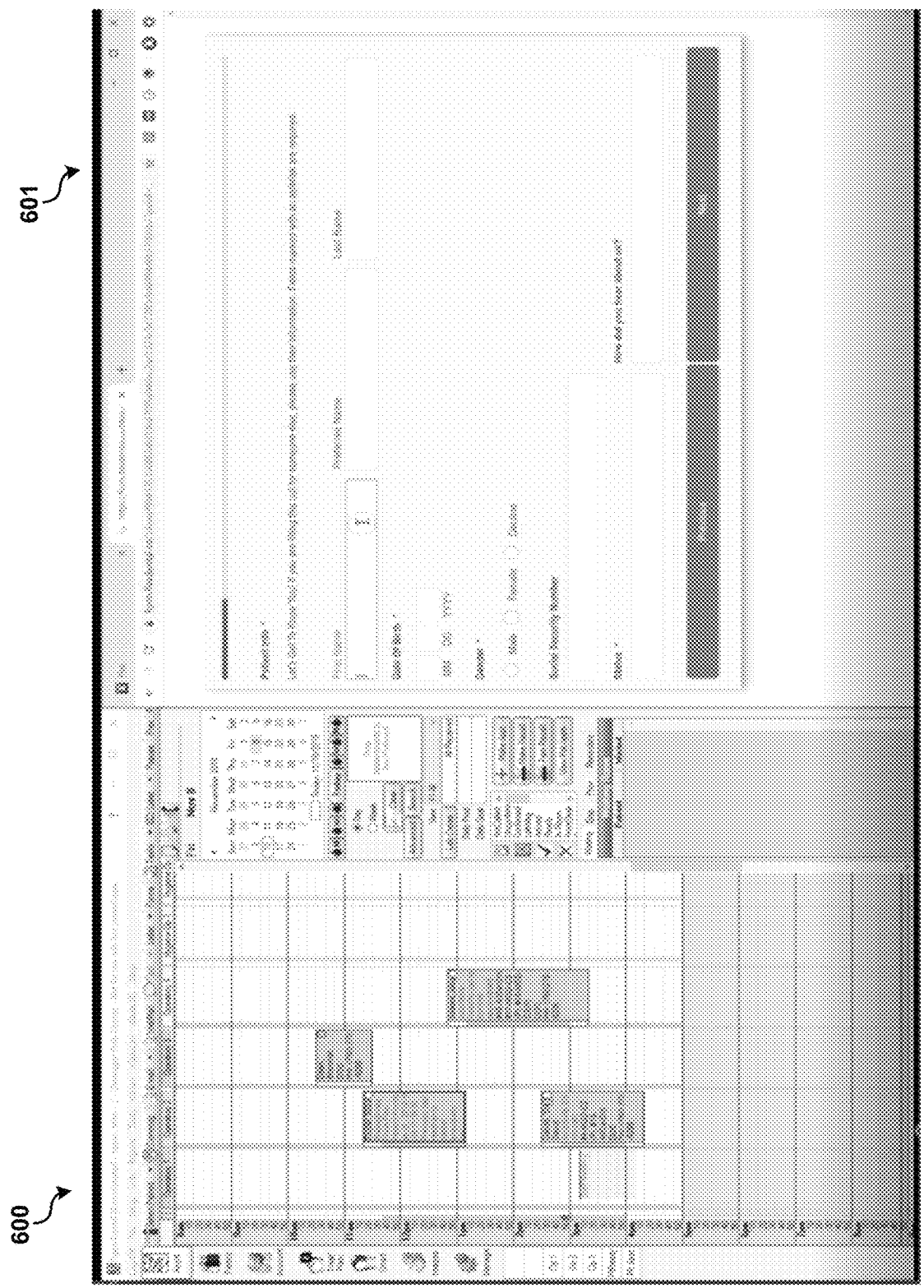
FIGS. 6-10 illustrate examples of displayed screens from the web-based platform associated with an implemented dynamic forms feature, according to one or more embodiments shown and described herein.

Now referring to FIG. 6, an example of a screen 600 that displays a dynamic form 601, which is a key feature of the web-based platform, is shown. The web-based platform is configured to allow its forms to be created, updated, and transferred using full automation. Thus, the web-based platform essentially eliminates the time and clutter associated with manually handling hard-copy (e.g., physical) forms. Instead of a dental office employee having to provide a stack of hard-copy (e.g., physical) forms to be filled out by (and collected from) each patient, a new patient (or appointment) can be created in the PMS and a form, such as the dynamic form 601 shown in screen 600. Furthermore, the web-based platform can automatically communicate the forms, once created, to the patient. For example, the dynamic form 601 can be e-mailed to the patient by the web-based platform via a Universal Request Locator (URL) link. By clicking on a URL that has been embedded into the e-mail opened by the patient's device, the corresponding dynamic form 601 (being customized for that particular patient) can be accessed from the web-based platform. Once accessed, the patient can use their patient device to fill out the dynamic form 601 electronically and subsequently submit the form 601 to the web-based platform to be stored and/or maintained by the PMS. Moreover, a feature of the dynamic form aspects platform involve the capability for all dynamic forms to fully (and automatically) integrate back into PMS without requiring any further interactions by the dental office employee. The platform's dynamic forms, such as dynamic form 601, can be easily customized and update dynamically in response to patient inputs (e.g., patient age, gender, insurance status, current health status, marital status, and current medications). That is, patient inputs are taken into account in order to dynamically streamline which questions are further presented within the form, adapting the form in manner that is optimized and specific to the patient. Additionally, dynamic forms can be automatically transmitted to the patient (e.g., via e-mail) by the web-based platform when new patients are created in the system. Consequently, pertinent intake forms can be filled out remotely via the patient's device, and automatically collected by the system even without the patient being physically present at the dental office. As an example, the web-based platform may be configured to ensure that a COVID-19 screening form is automatically transmitted to every new patient, and received by the system prior to their first scheduled appoint. Alternatively, dynamic forms of the web-based platform, such as dynamic form 601, may be used in a more traditional manner, being completed in-office by the user in electronic form on the dental office system (e.g., patient data being entered into tablet used by a dental office employee). Also, dynamic forms can be automatically pre-filled with existing information (e.g., updated medical history) ahead of that patient's next appointment.

Figure 7:
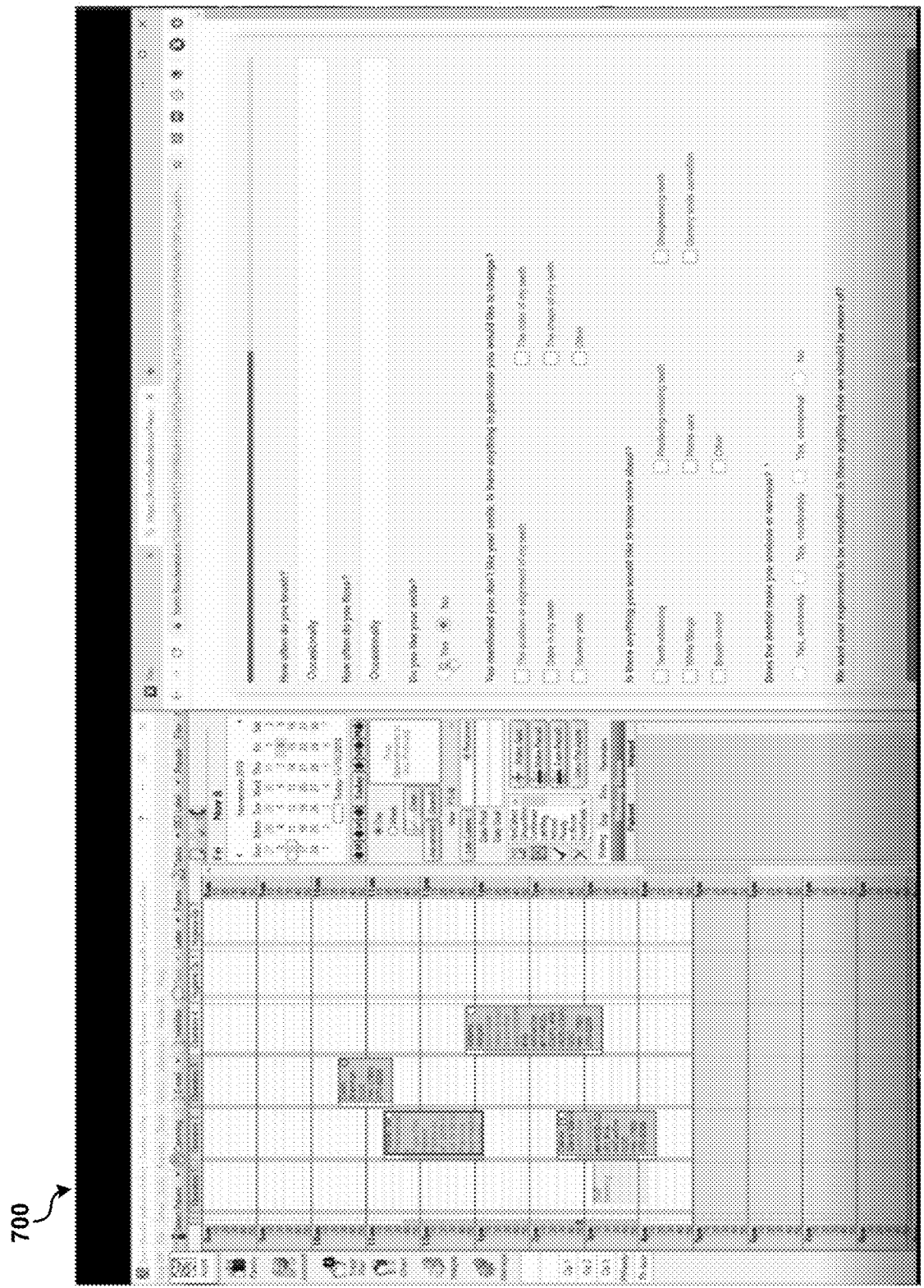
Figure 8:
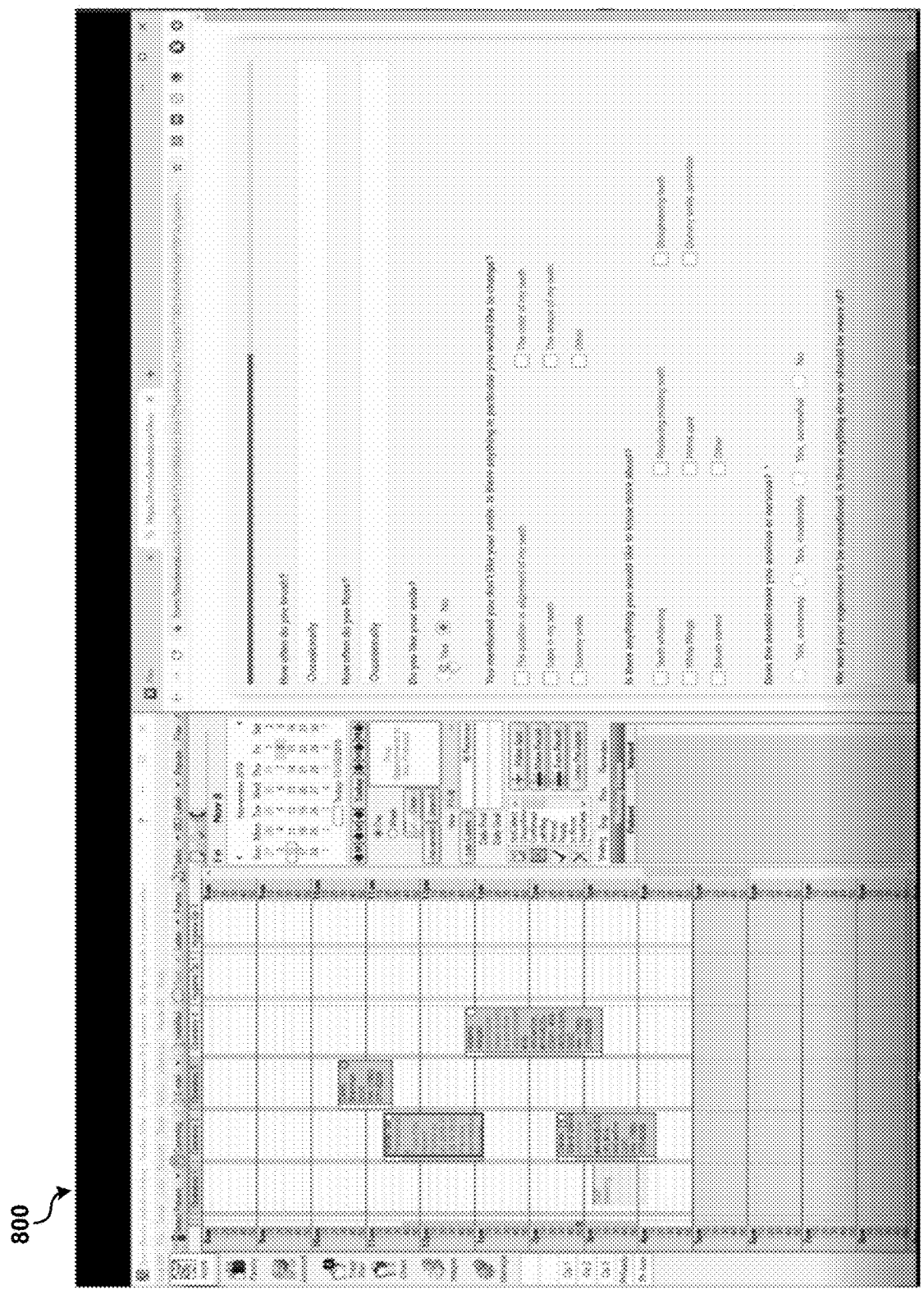

The dynamic form 601 displayed in screen 600 of FIG. 6, can be a patient intake form generated by the web-based platform. As alluded to above, the patient intake form can be dynamic. Referring now to FIG. 7, screen 700 shows a portion of a form that includes a question. In detail, screen 700 displays "Do you like your smile?" with options corresponding selectable responses (e.g., radio buttons) "Yes" or "No." To illustrate the dynamic functionality of the system's forms, the answer to this particular question can initiate a dynamic change to the form. In the illustrated example of FIG. 7, entering "No" can includes subsequent questions "You mentioned that you don't like your smile. Is there anything particular you would like to change?" with corresponding selectable responses. However, in FIG. 8, showing screen 800 including the same portion of the form as seen in FIG. 7, a user can alternatively select "Yes" to the "Do you like your smile?" questioned presented in the form. As a result, the other questions that are more pertinent for a patient that may desire more complex dental procedures (e.g., does not like their smile), are not displayed in the form in screen 800. Dynamically adjusting forms allows for the web-based platform to have a single form that can be applied to different patients, and having multiple uses, which typically would require a stack of different traditional hard-copy forms.

Figure 9:
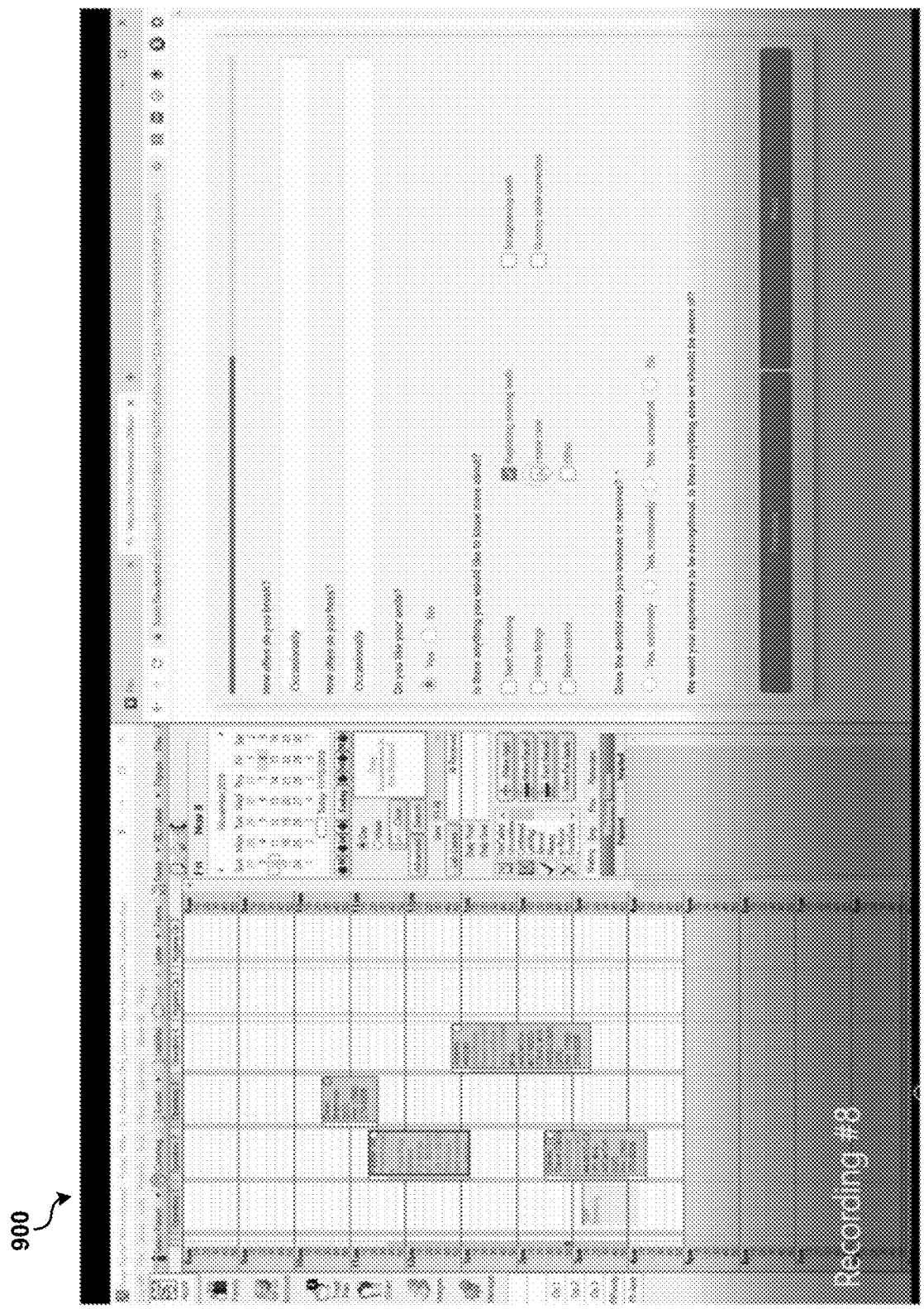
Figure 10:
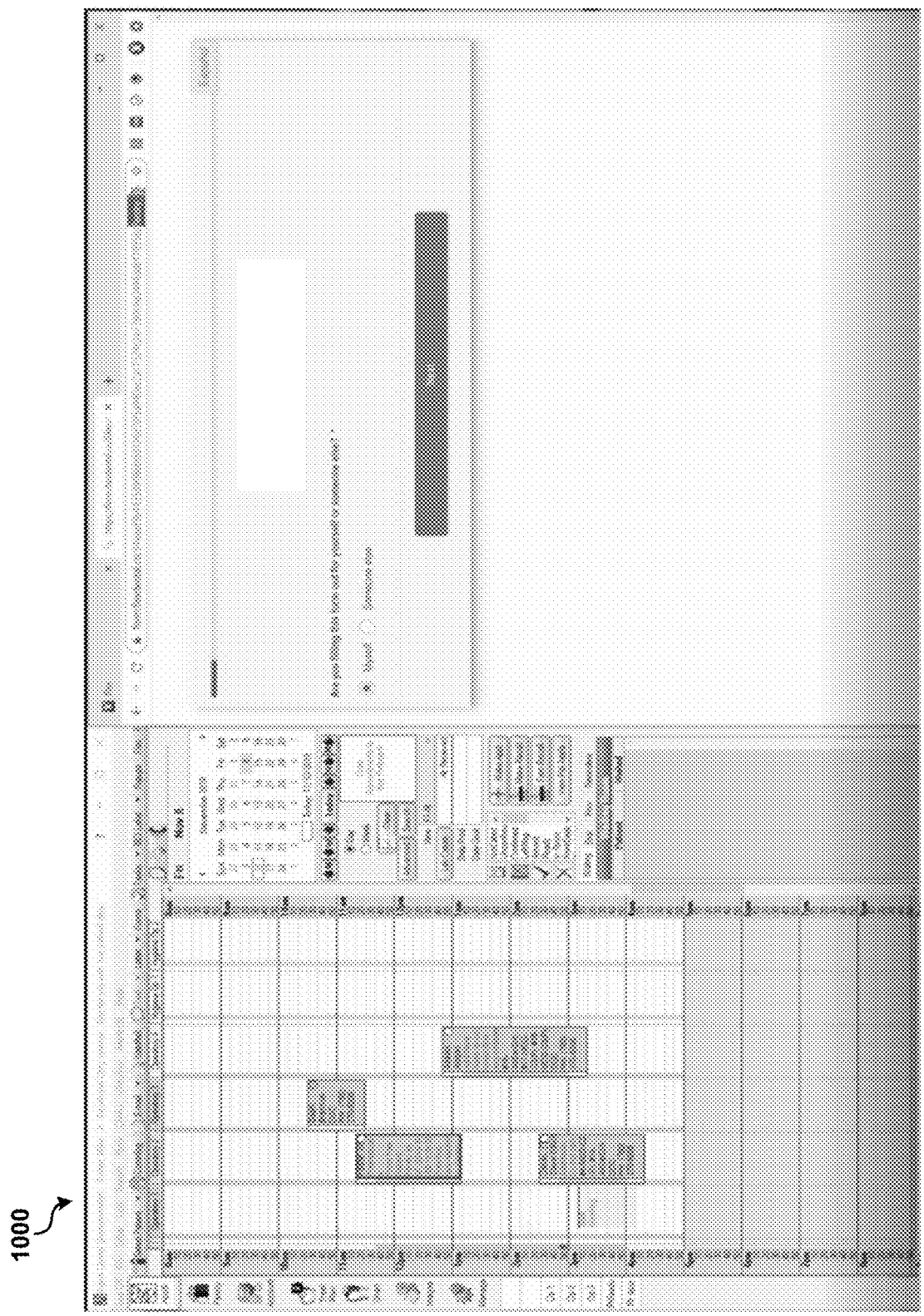

An example of this, many dental offices are required to have pediatric and adult versions of forms. In contrast, the web-based platform has the capability to dynamically modify the form to be usable for either an adult patient or a child patient (e.g., based on the answers). FIGS. 9-10 show additional examples of screen that can be displayed by the web-based platform, allowing interaction with its dynamic form features. FIG. 9 depicts a screen 900 that can be employed to display another example of a patient intake form, where the patient intake form include dynamic form features. In FIG. 10, another screen 1000 is depicted that can display another portion of a patient intake form. As another example of dynamic functionality of the forms in the web-based platform, of a patient enters information that indicates that they are a male of 65 years of age, then the forms will not present questions relating to pregnancy (e.g., younger, female) to that patient.

Figure 11:
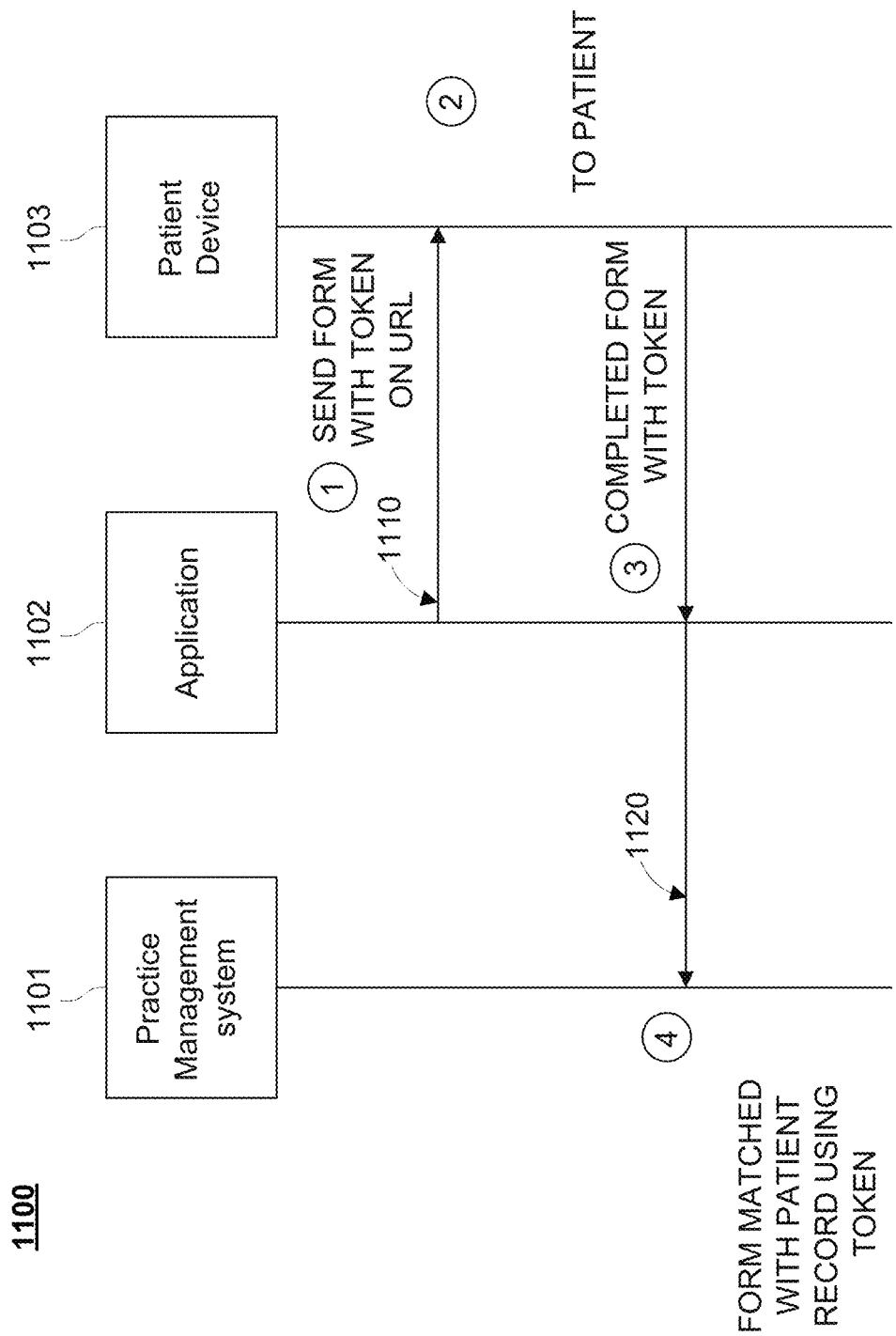
FIG. 11 illustrates an example of a message flow related to transmission of a dynamic form via the web-based platform, according to one or more embodiments shown and described herein.

Referring now to FIG. 11, an example of a message flow 1100 related to communication of a dynamic form via the web-based platform is depicted. The flow 1100 can start with at exchange 1110, where a form is transmitted form the web-based platform 1102 to a patient device, for instance the patient's smartphone. In some cases, the web-based platform can communicate a dynamic form via a SMS message (also referred to herein as text message). For an added layer of security and automation, the web-based platform utilizes tokens. For instance, the web-based platform can generate a unique token for a patient. Subsequently, when dynamic forms are transmitted to the patient, the token corresponding to the patient can also be communicated to the patient device. In some cases, the token can be represented using a series of characters that are automatically generated by the web-based platform. This token may be a digital object that is also known by the PMS, where the PMS corresponds the token to any records for that patient being stored on the system. Thus, the token acts a tamper-proof identifier for a user and enables automated accessibility to certain data linked to the user that is identified by the token. While a token is generally used to represent only security-related information, the token may be capable of holding additional free-form data that can be attached while the token is being created.

In some embodiments, the web-based platform appends, or otherwise embeds the token within the URL that is used by the user to access the web-based platform and ultimately their specific treatment plan and dynamic forms. When the initial SMS message is received by the patient device 1103, when the user clicks the URL, the token may be validated in order to generate a specific URL link that uniquely corresponds to accessing the forms for that particular patient. Thus, the web-based platform, being aware of the particular patient receiving the form and the token, has a point of reference with respect to the data that can be pulled into the form (e.g., from the PMS 1101). That is, the PMS 1101 can use the token to determine which records on the system correspond to the patient that has clicked the link and pass that data to the platform. For example, a dynamic form can be opened on the patient's device 1103, after a user clicks the URL link and the token is validated. Further, as a result of pulling data corresponding to the specific patient from the PMS 1101 (vis-à-vis the token), the dynamic form can be presented to the patient already including some patient-specific data from the PMS that is pre-populated in the form. For instance, the PMS may be able to determine general data for that patient from stored records, such as name, age, gender, using the token. Consequently, a dynamic form can be presented to the patient on their patient device 1103, already having their name, age, gender, already included into the form. Next, the patient can complete the form (e.g., entering detailed information or data not already in the PMS), in some cases using the patient device 1103 to enter data directly into the form's fields.

Thereafter, in exchange 1120, the patient device 1103 can send back the completed form to the web-based platform 1102. Similarly, the patient device 1103 returns the form to the web-based platform 1102 with the same unique token. Subsequently, the web-based platform 1102 then transfers the completed form to the PMS 1101. This serves to illustrate that, in many scenarios, the web-based platform 1102 functions as a pass-thru for data. In other words, the web-based platform 1102 exchanges information between the patient 1103 and the PMS 1101 in a transient manner (e.g., not persistently storing data), mitigating any security risk that may be associated with storing medial data or personal identifiable information of patients.

In response to the PMS 1101 receiving the completed dynamic form from the web-based platform 1102, this form can be matched with the patient record that is currently stored in the system (e.g., corresponding to the patient of patient device 1103) using the attached token. Once the form is successfully matched, the PMS 1101 can pull the data that was entered into the system.

Figure 12:
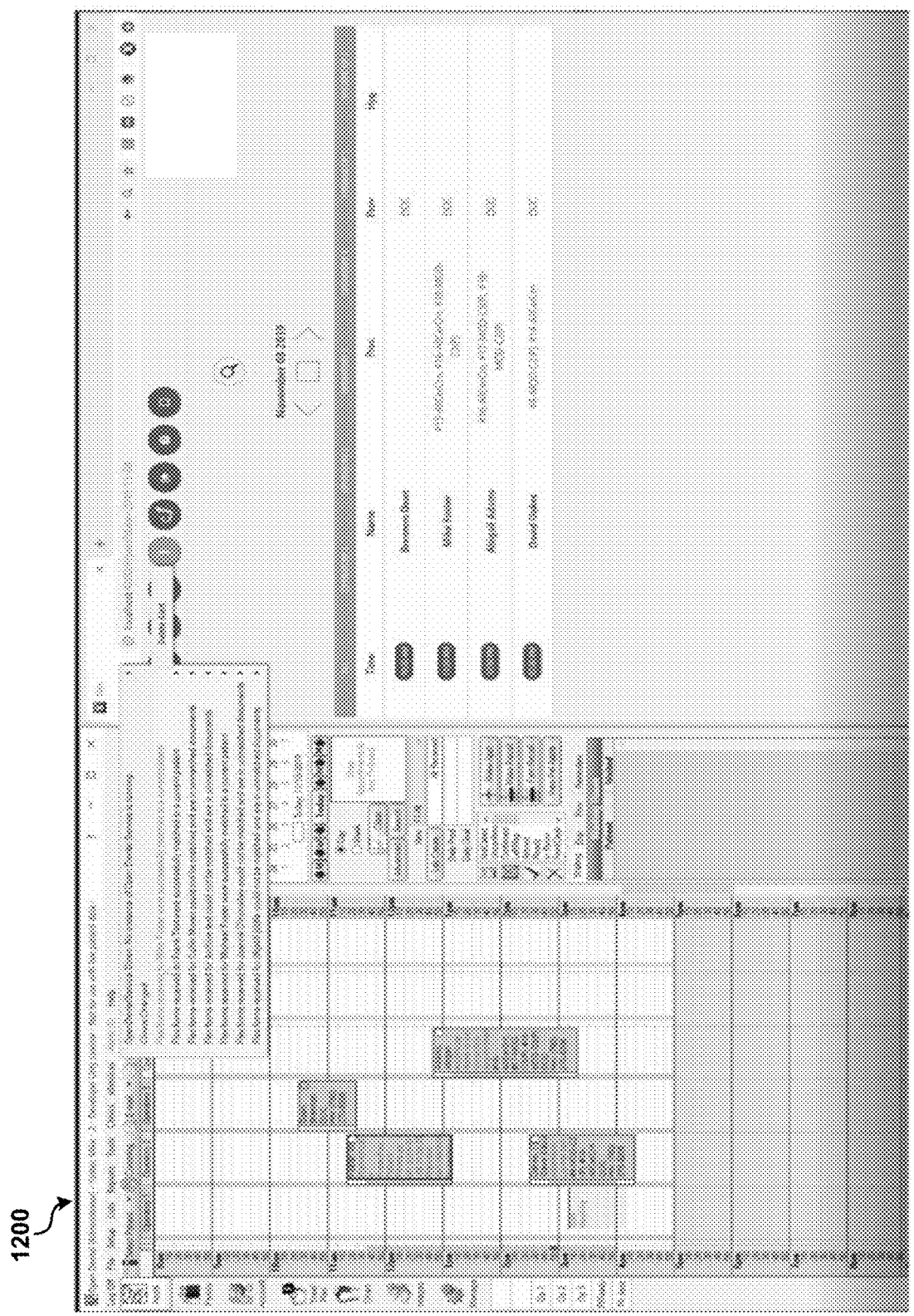
FIGS. 12-15 illustrate additional examples of displayed screens from the web-based platform associated with an implemented dynamic forms feature, according to one or more embodiments shown and described herein.
Figure 13:
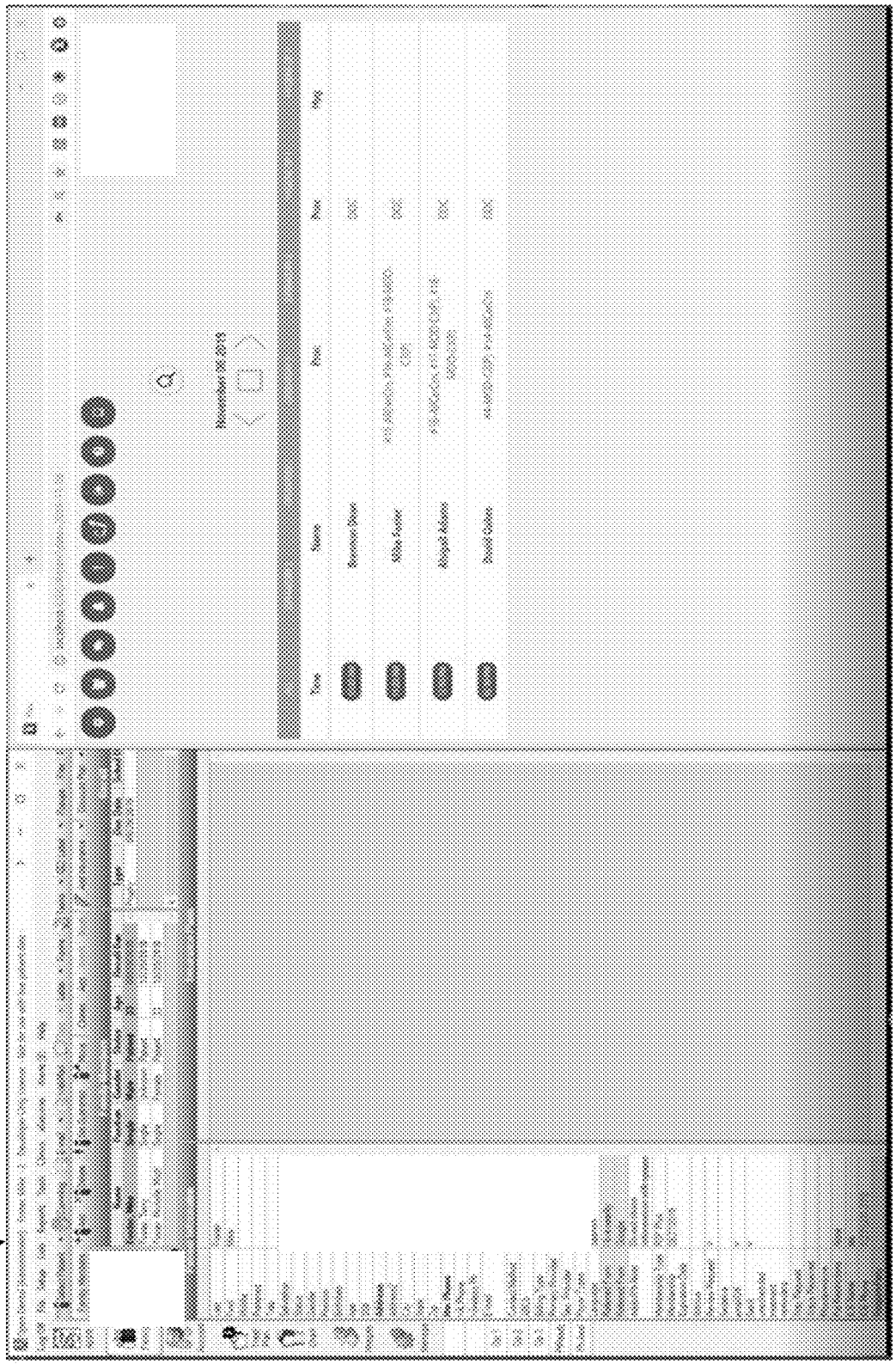
Figure 14:
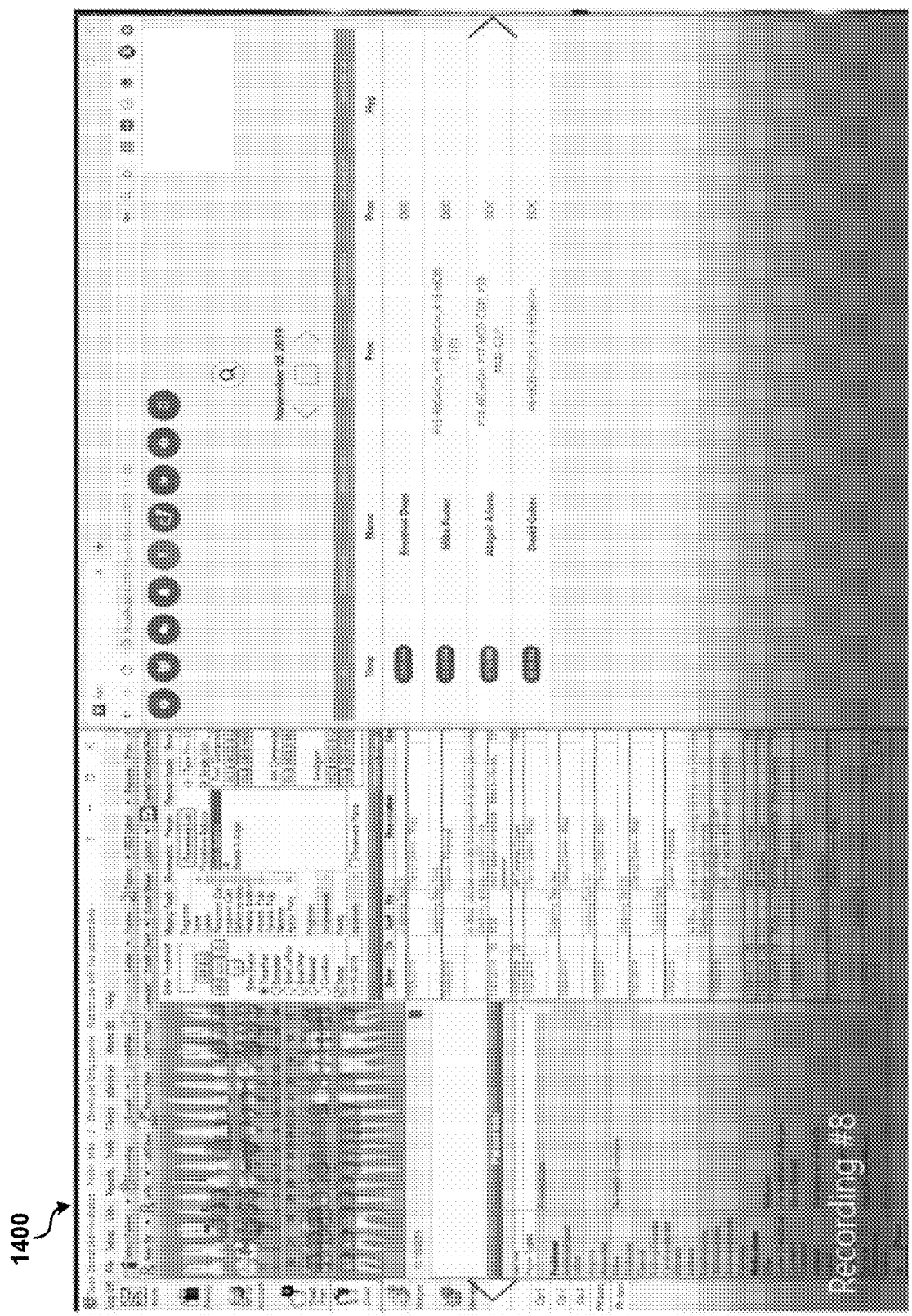
Figure 15:
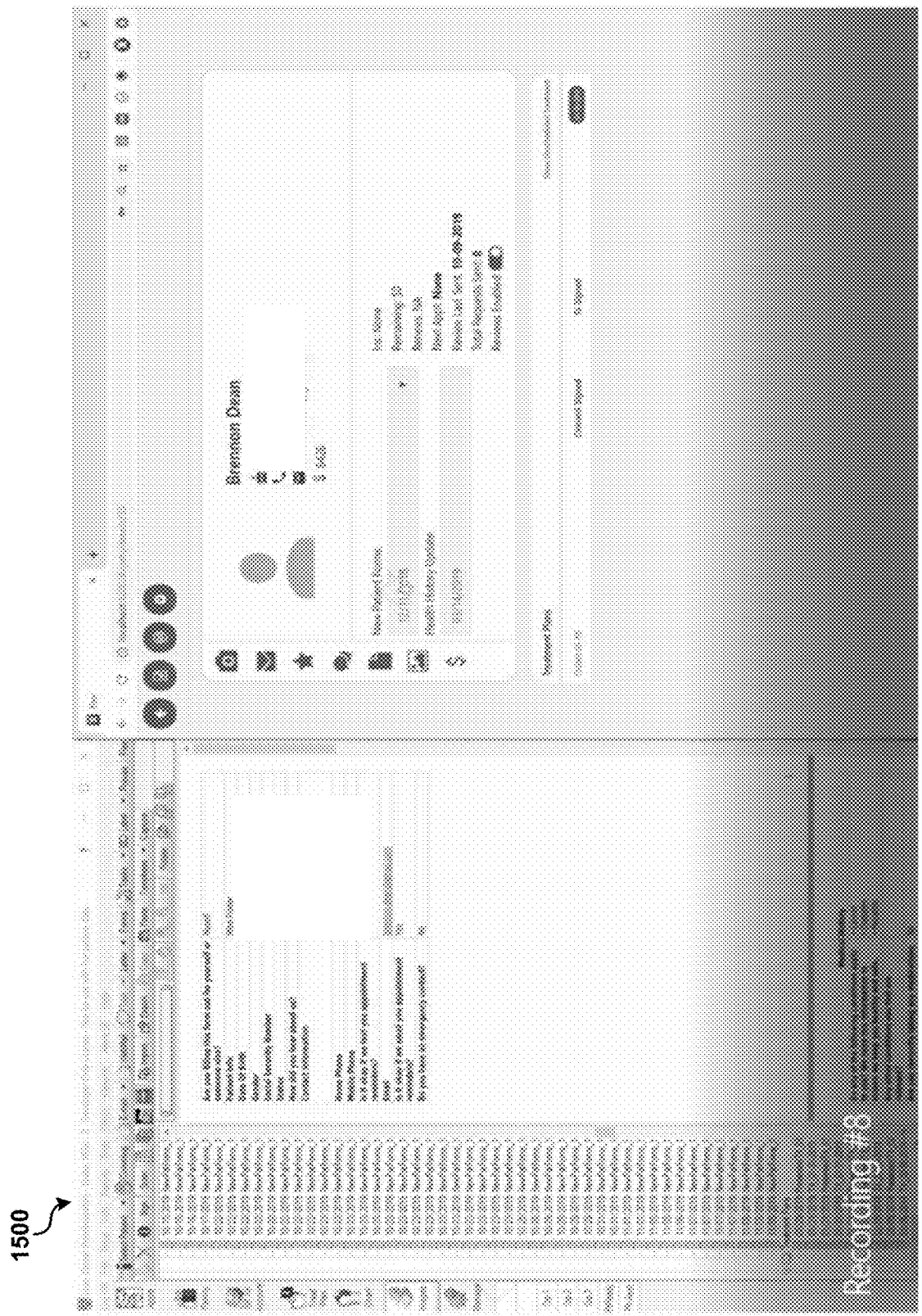
Figure 16:
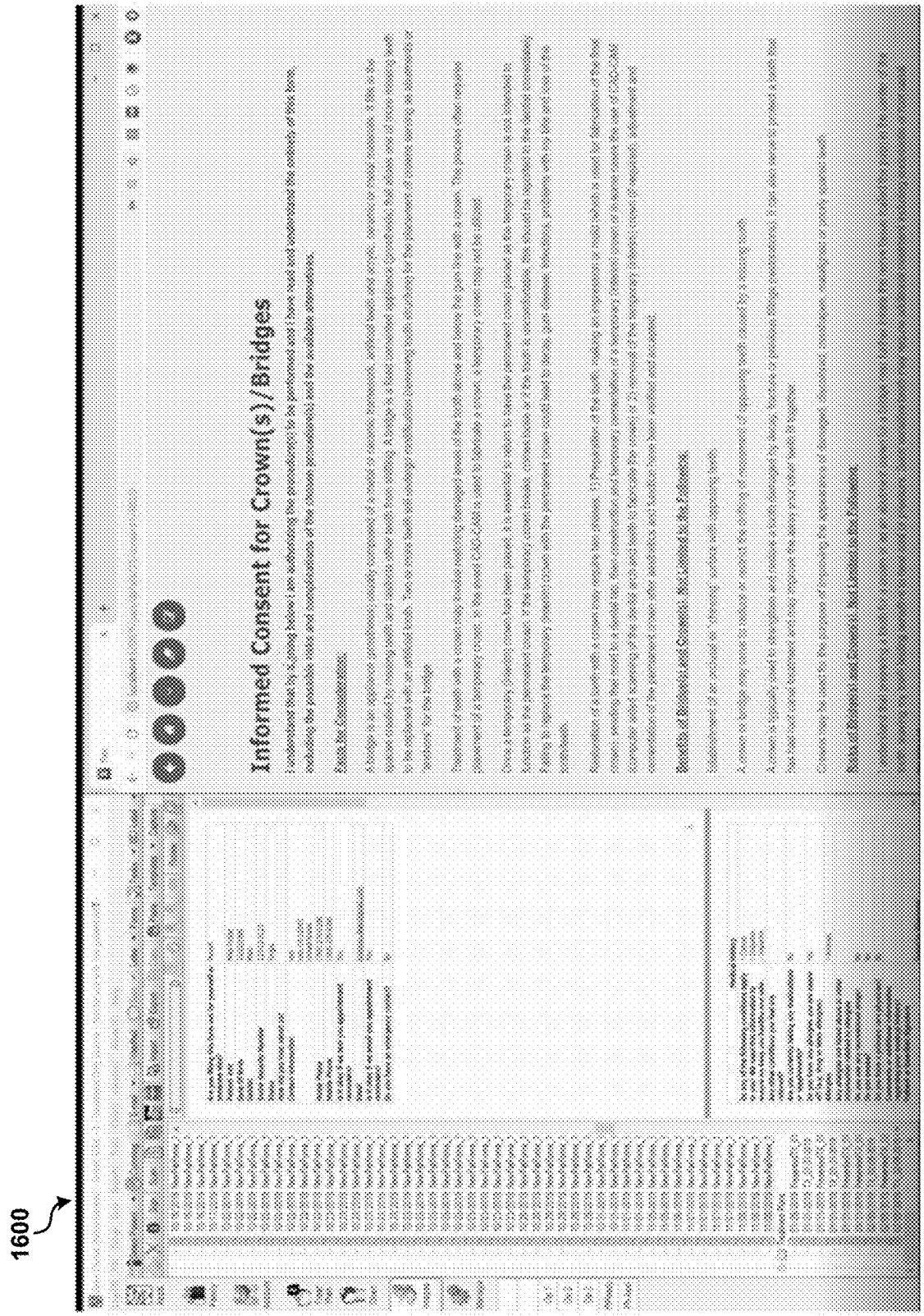
FIGS. 16-33 illustrate examples of displayed screens from the web-based platform associated with an implemented consent forms feature, according to one or more embodiments shown and described herein.
Figure 17:
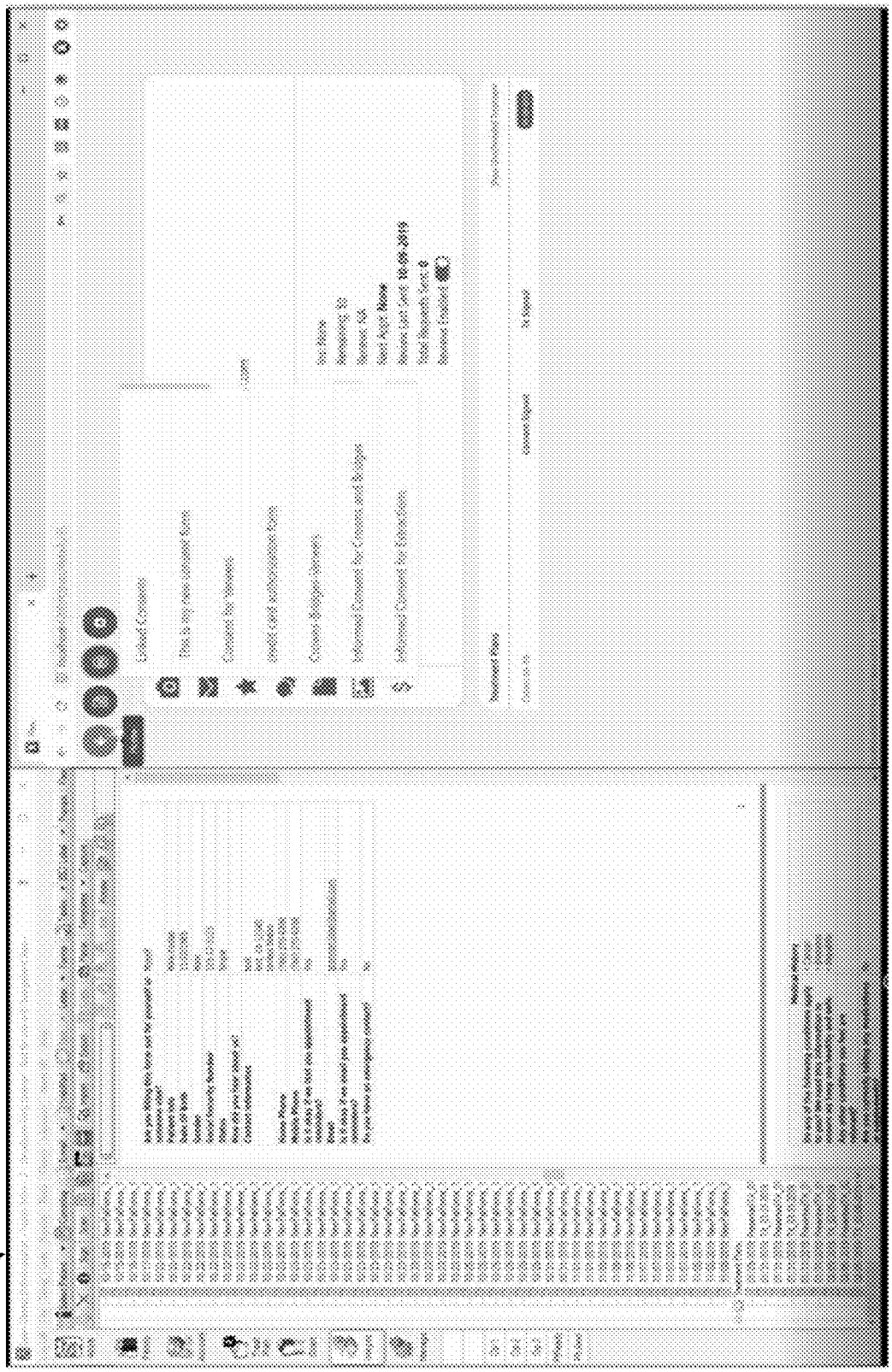
Figure 18:
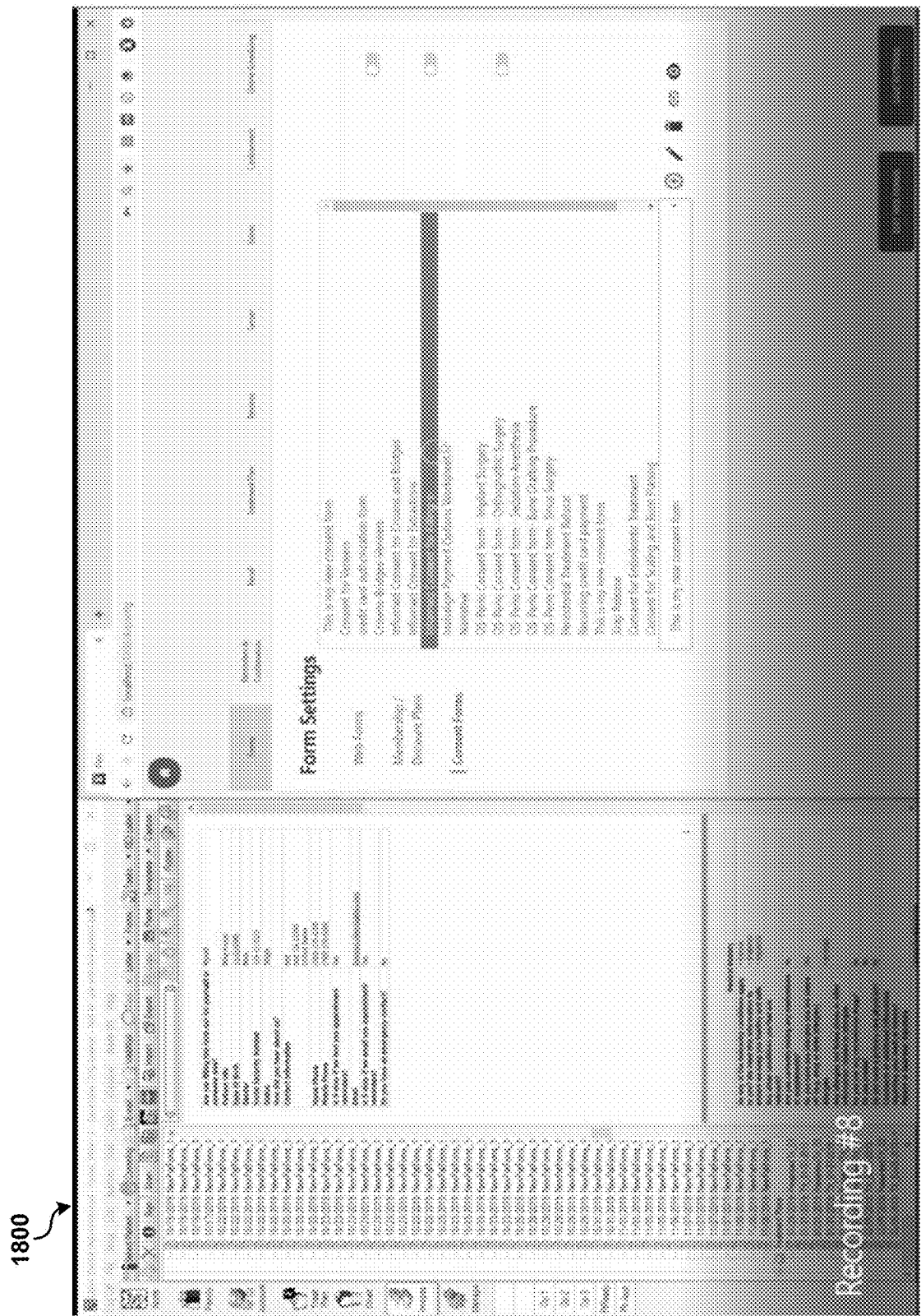
Figure 19:
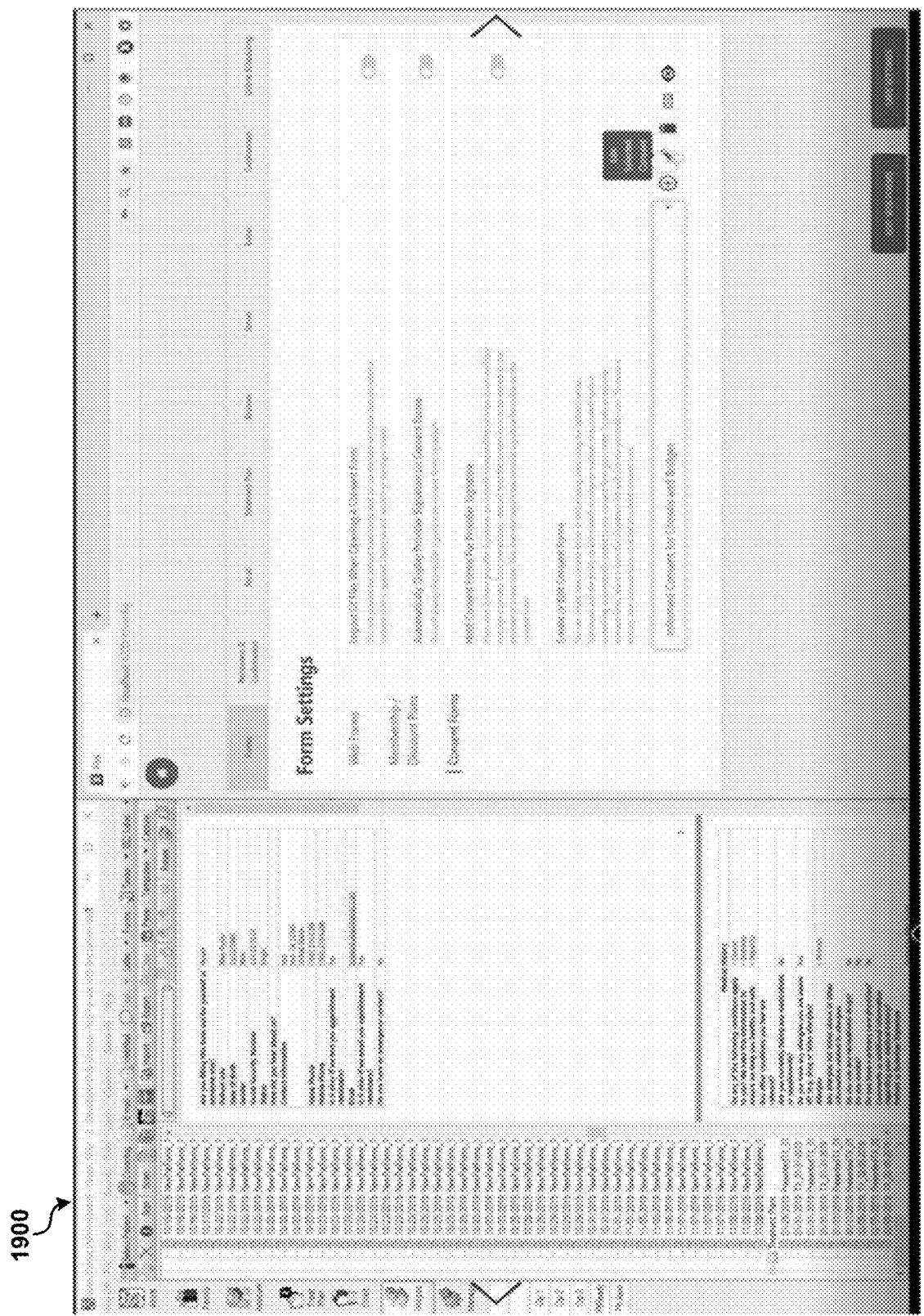
Figure 20:
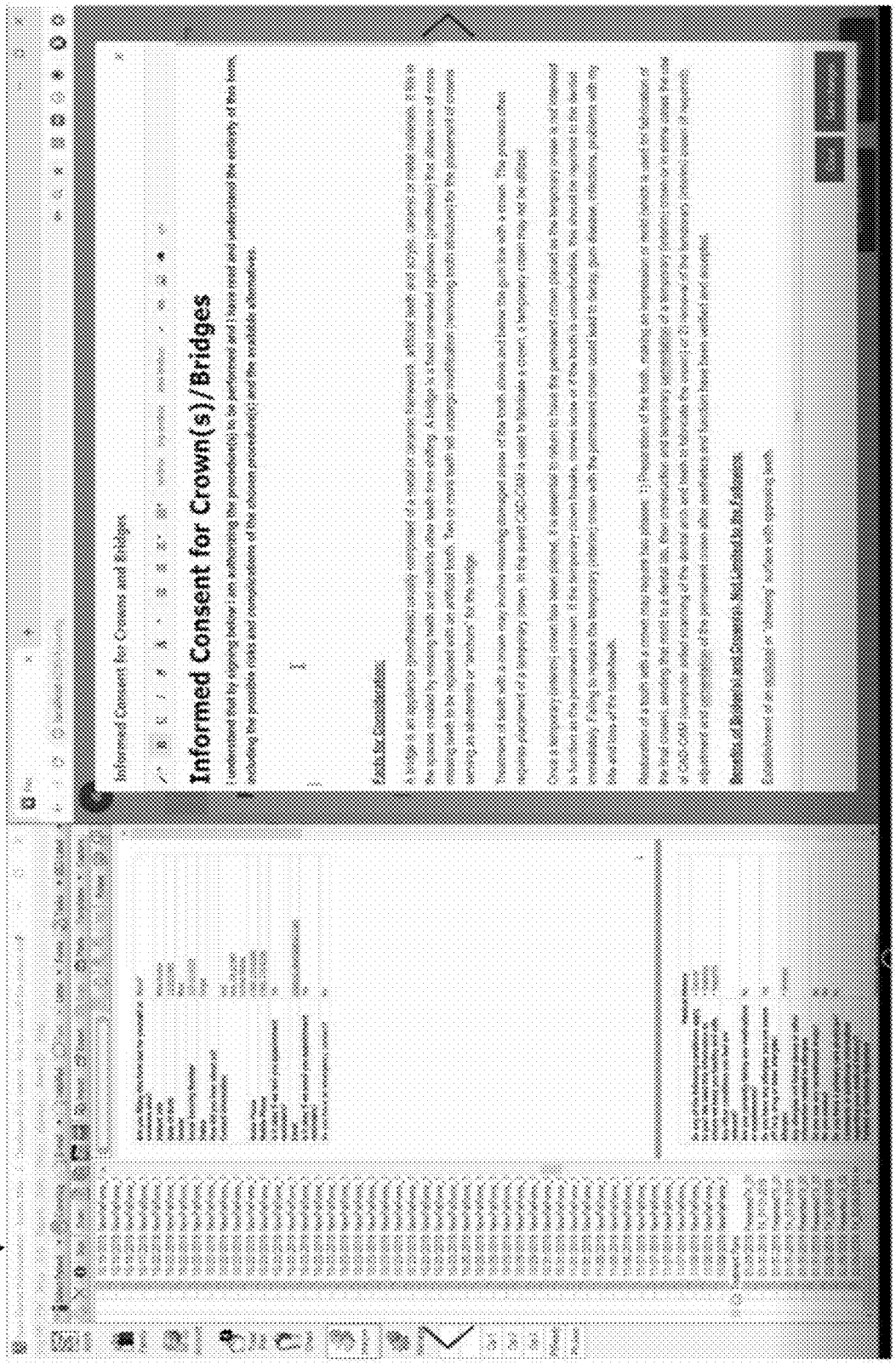
Figure 21:
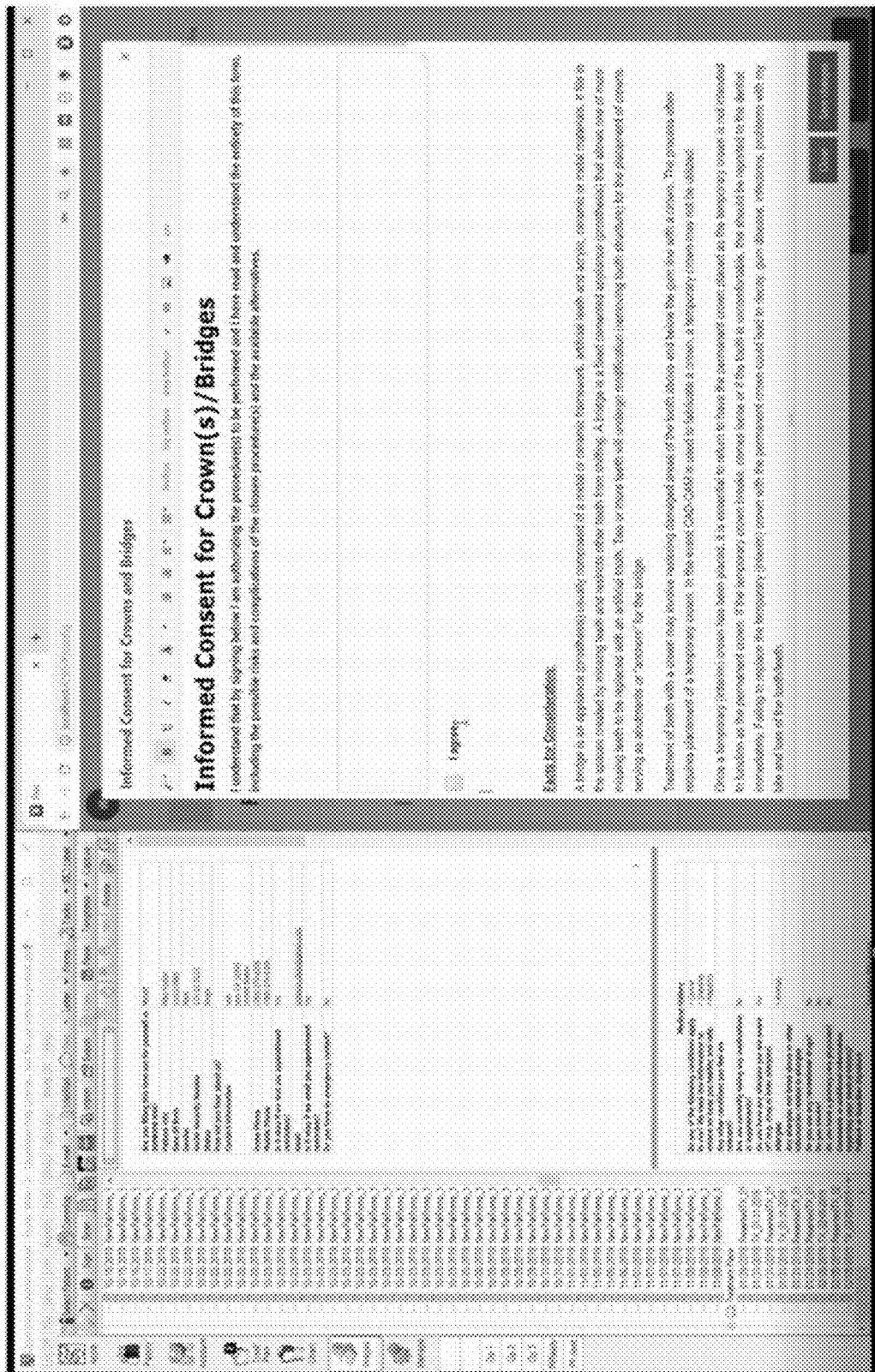
Figure 22:
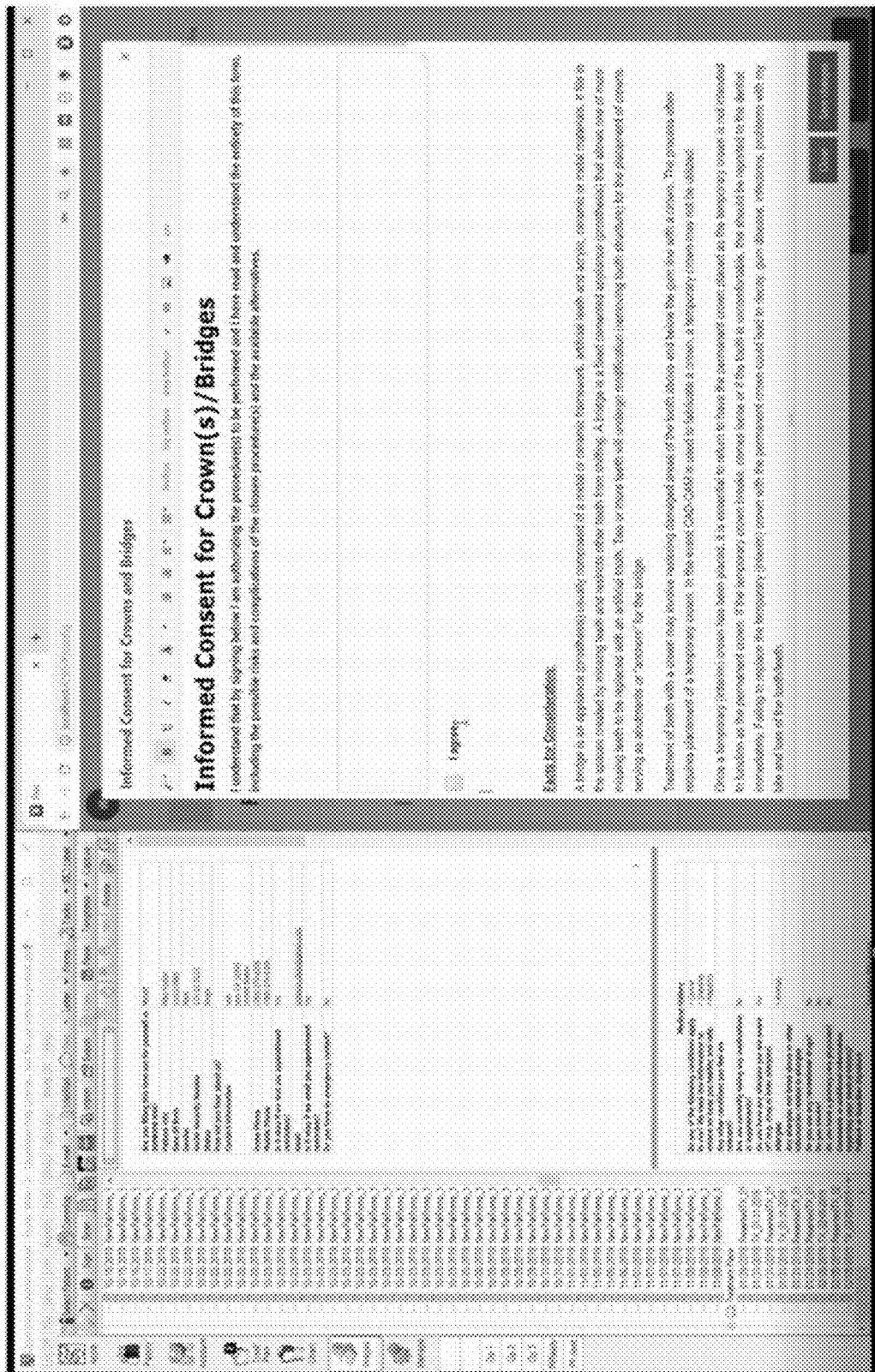
Figure 23:
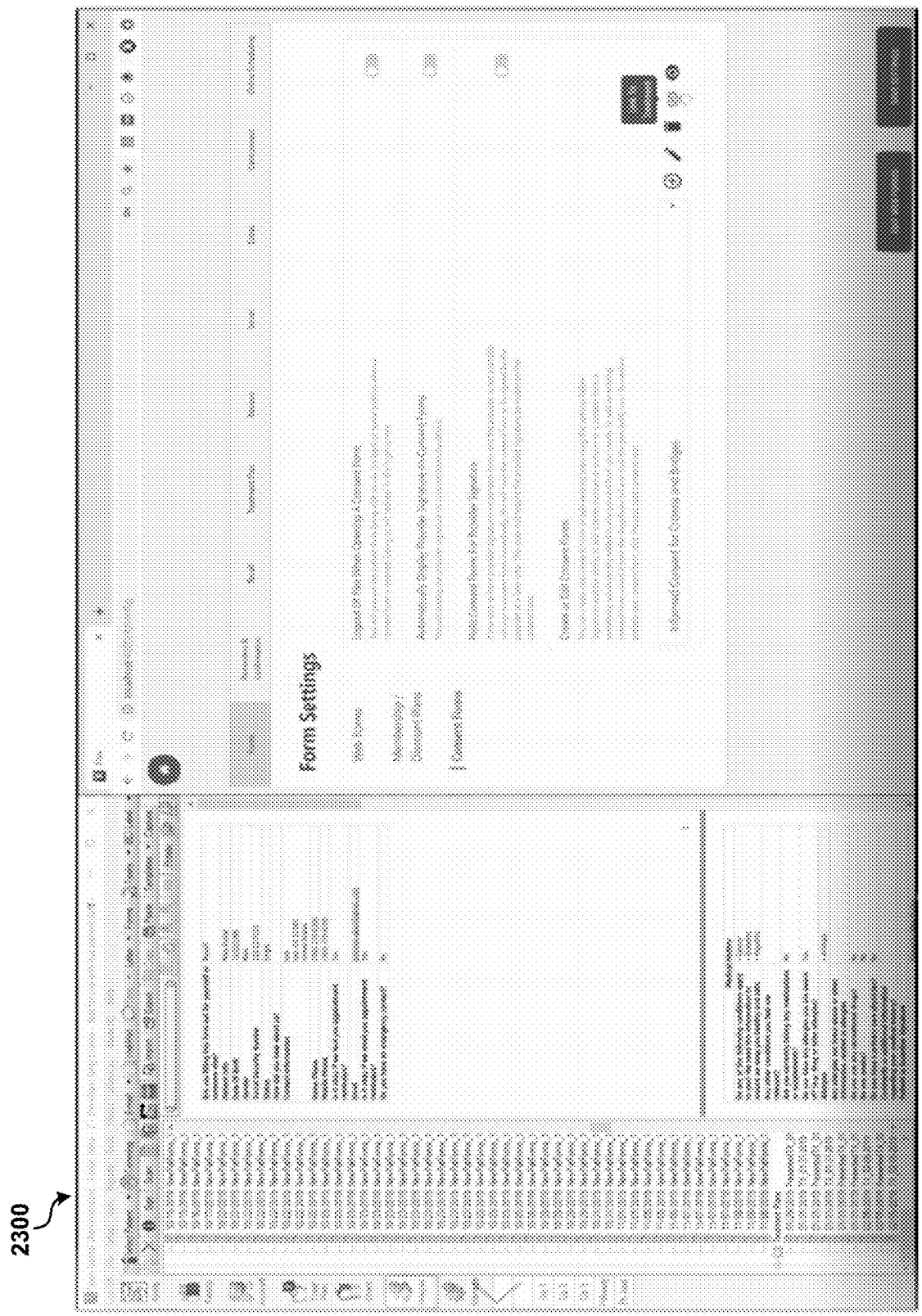
Figure 24:
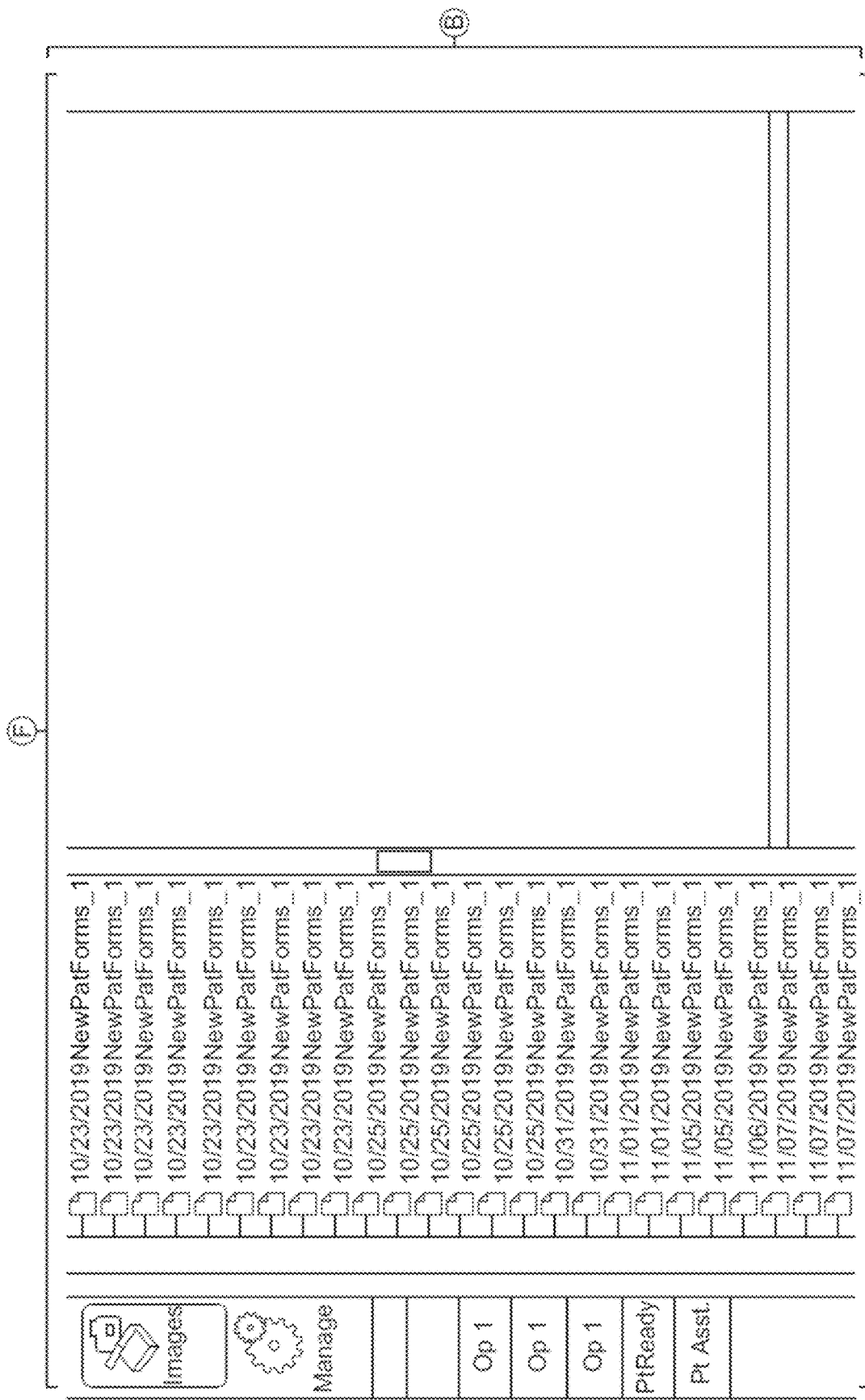
Figure 24:
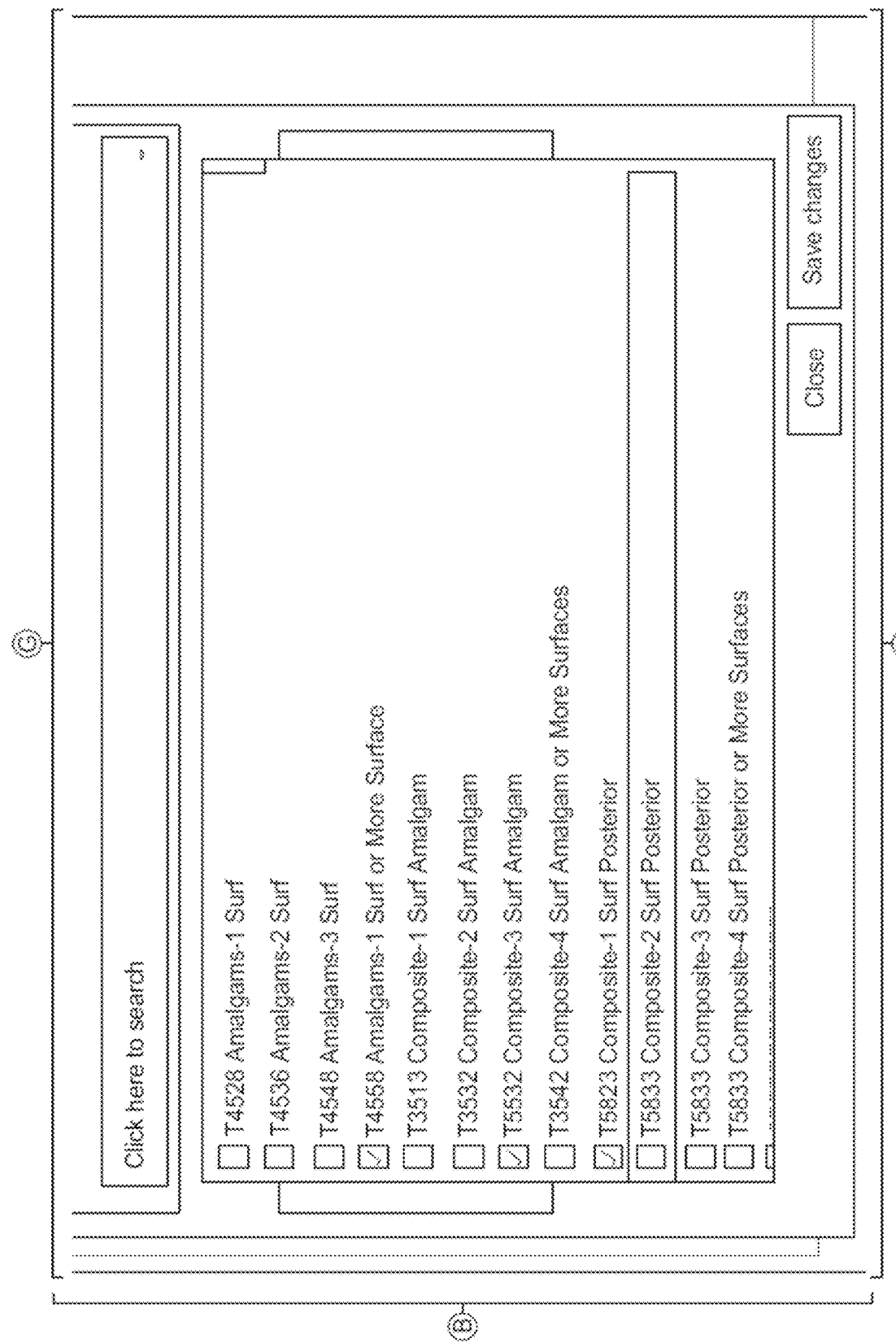
Figure 24:
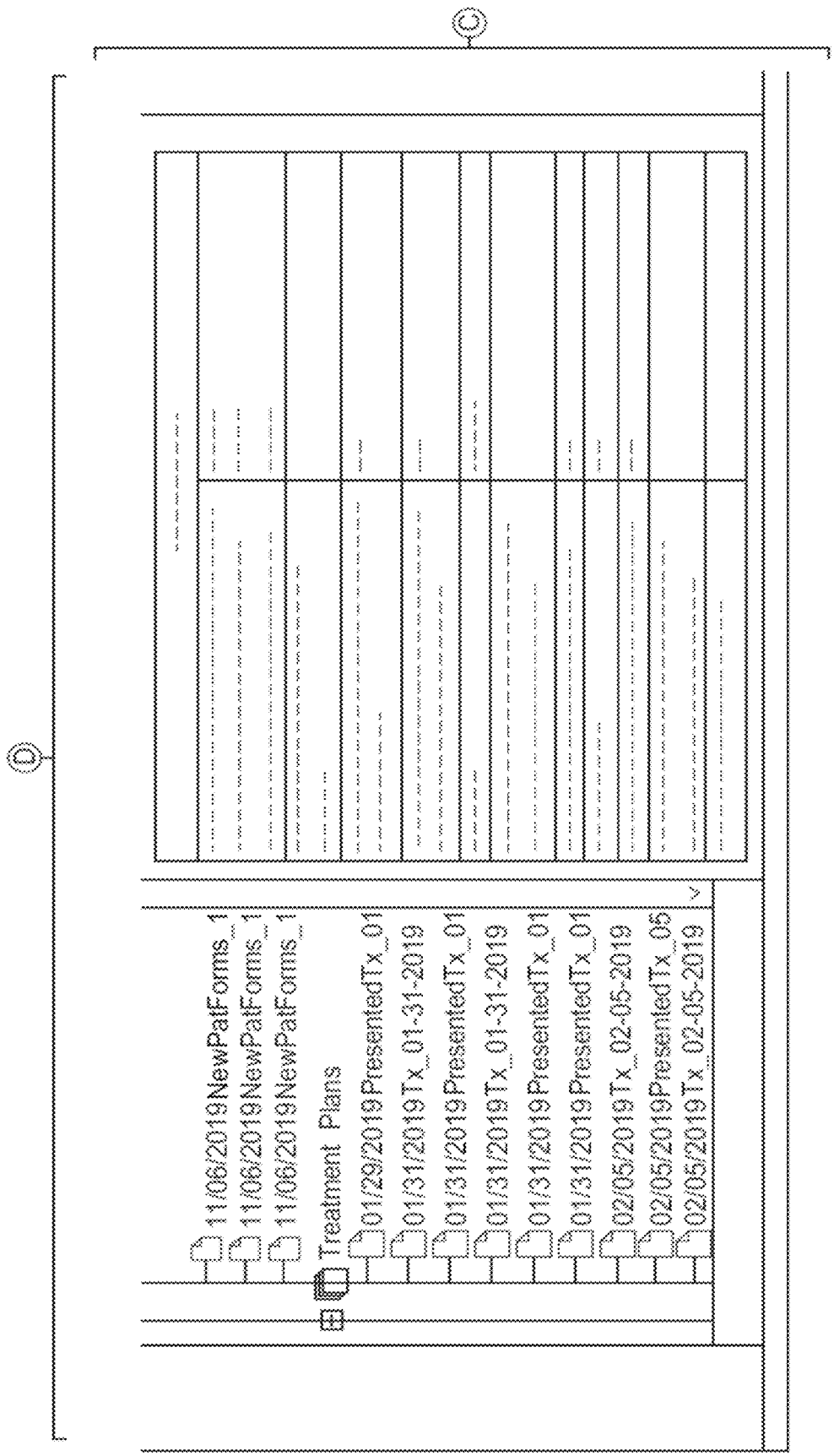
Figure 25:
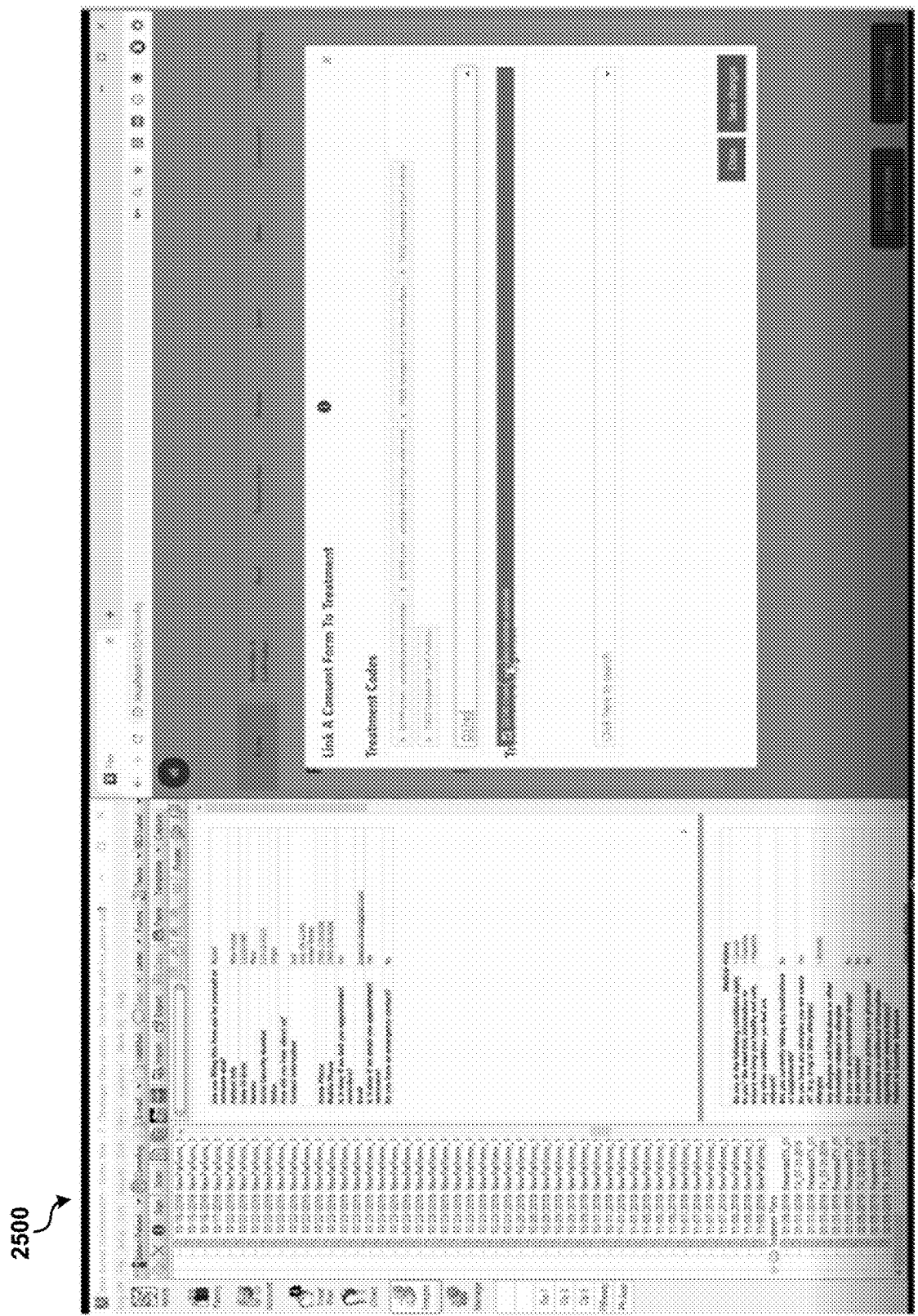
Figure 26:
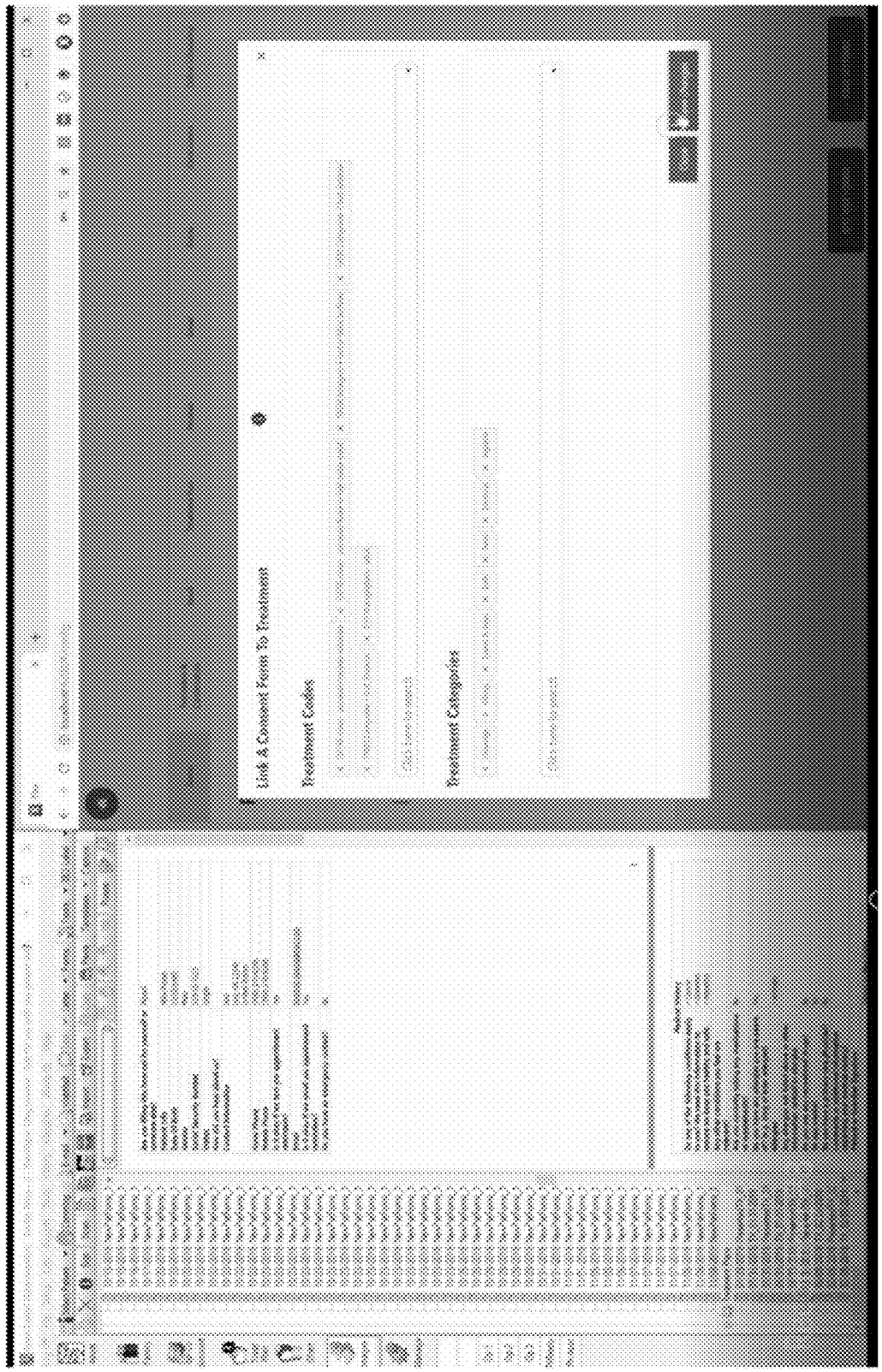
Figure 27:
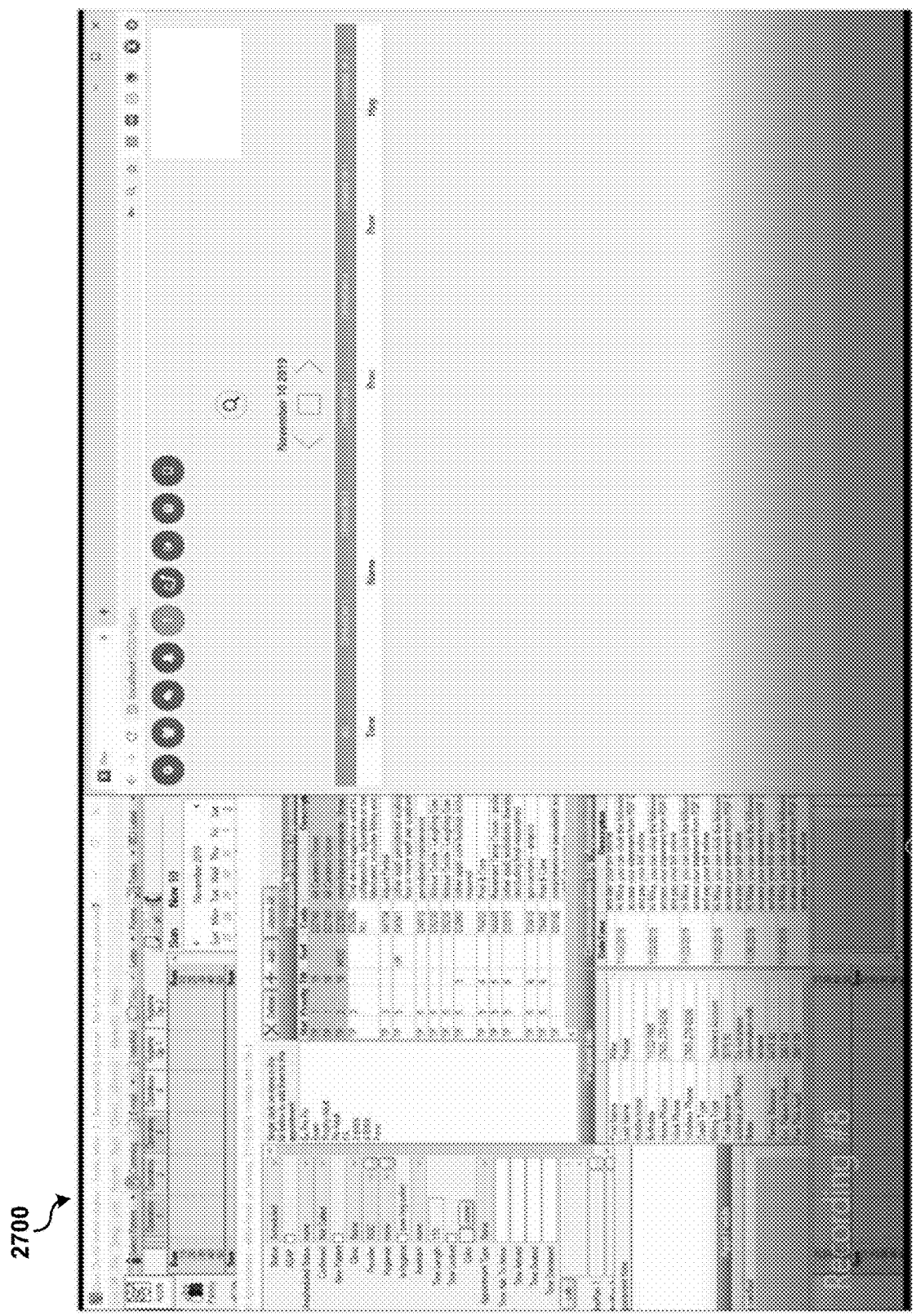
Figure 28:
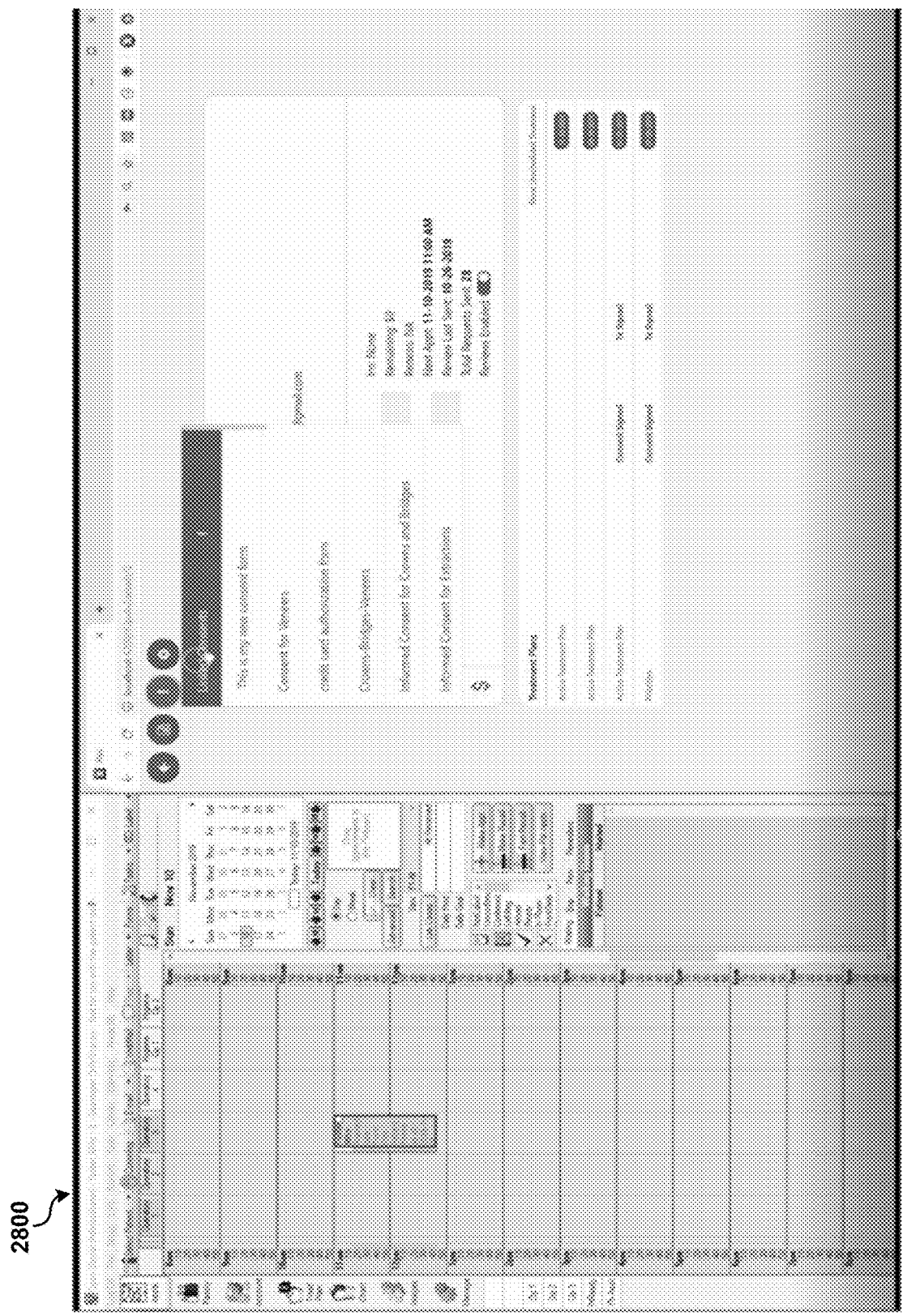
Figure 29:
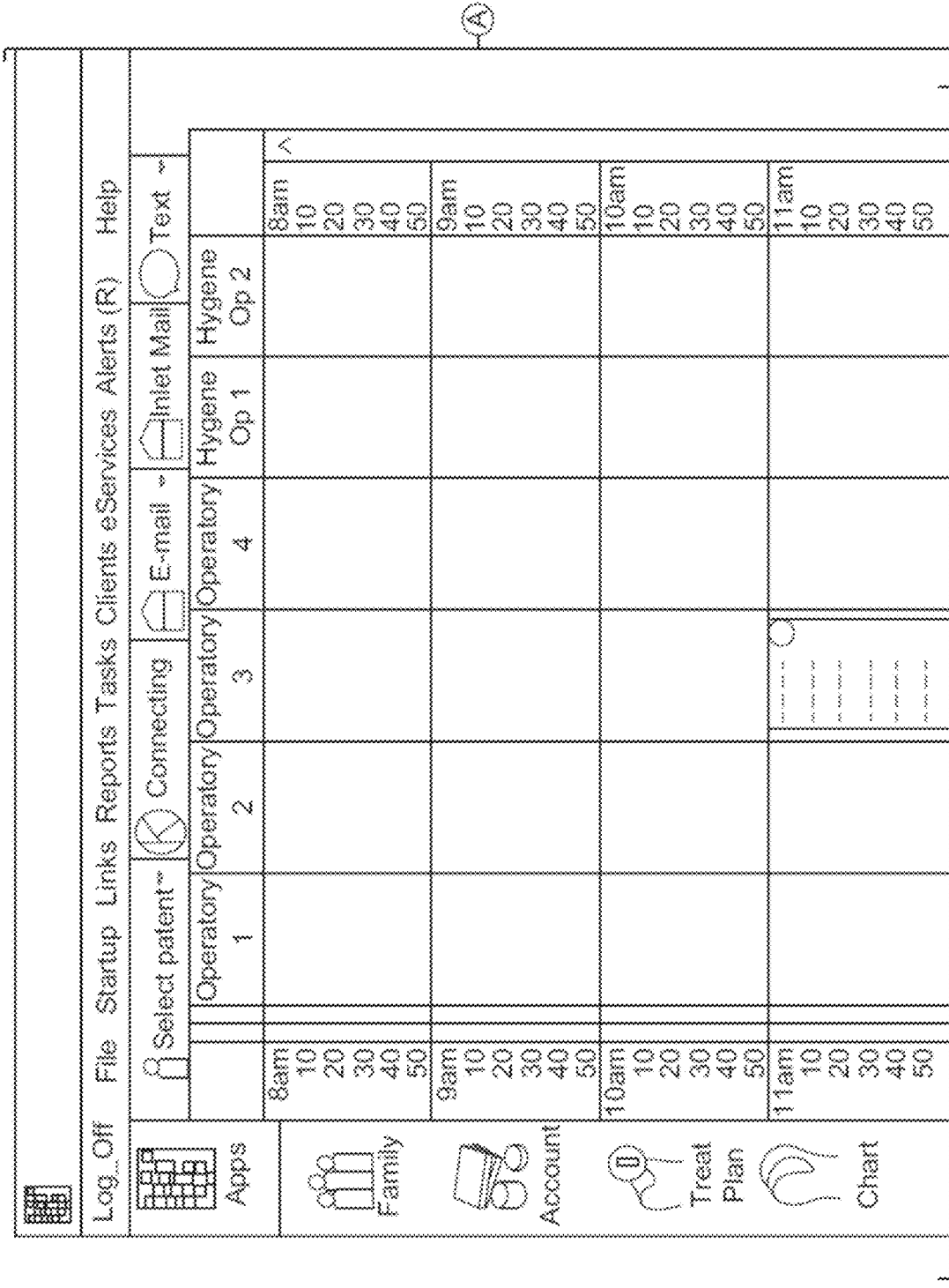
Figure 29:
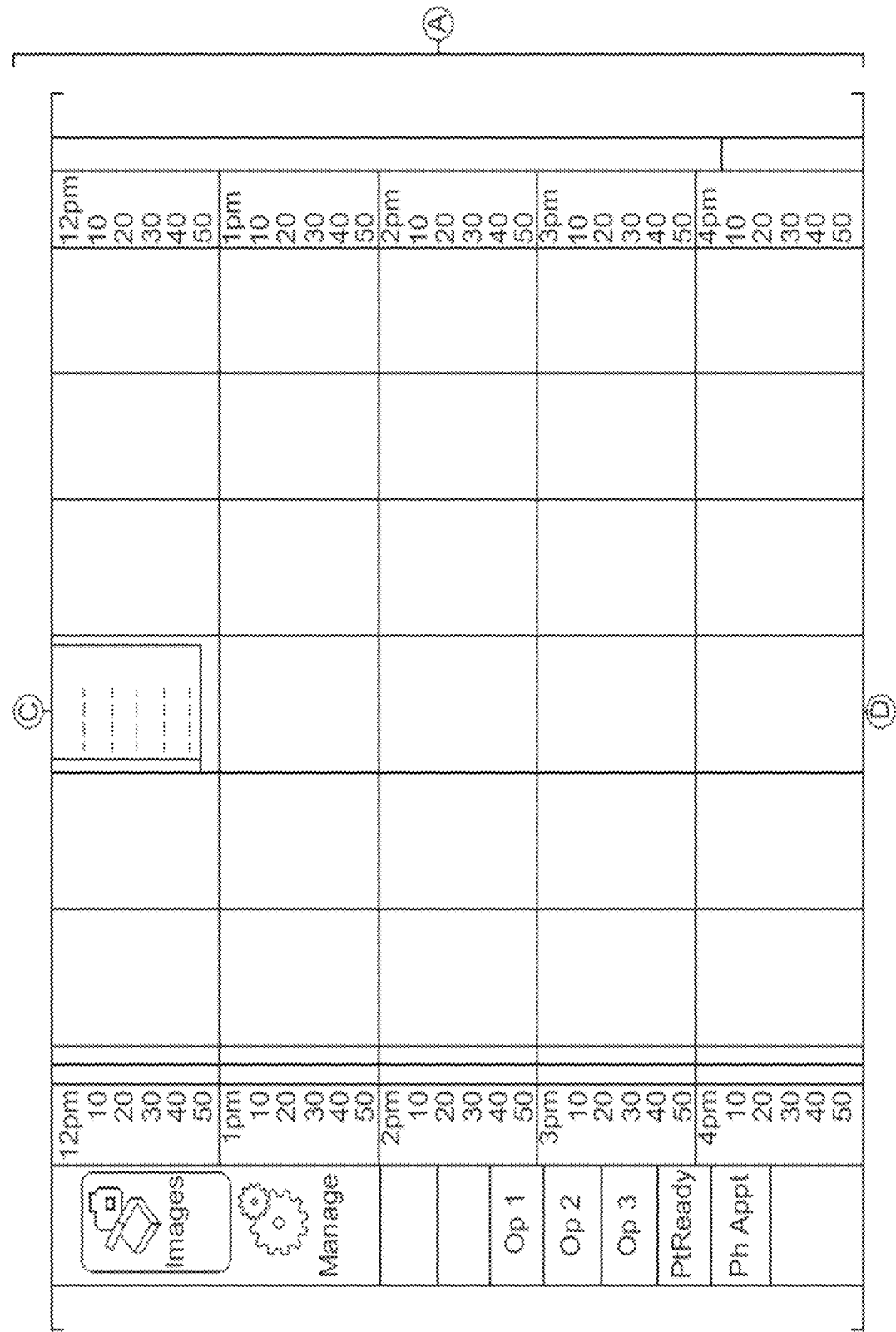
Figure 29:
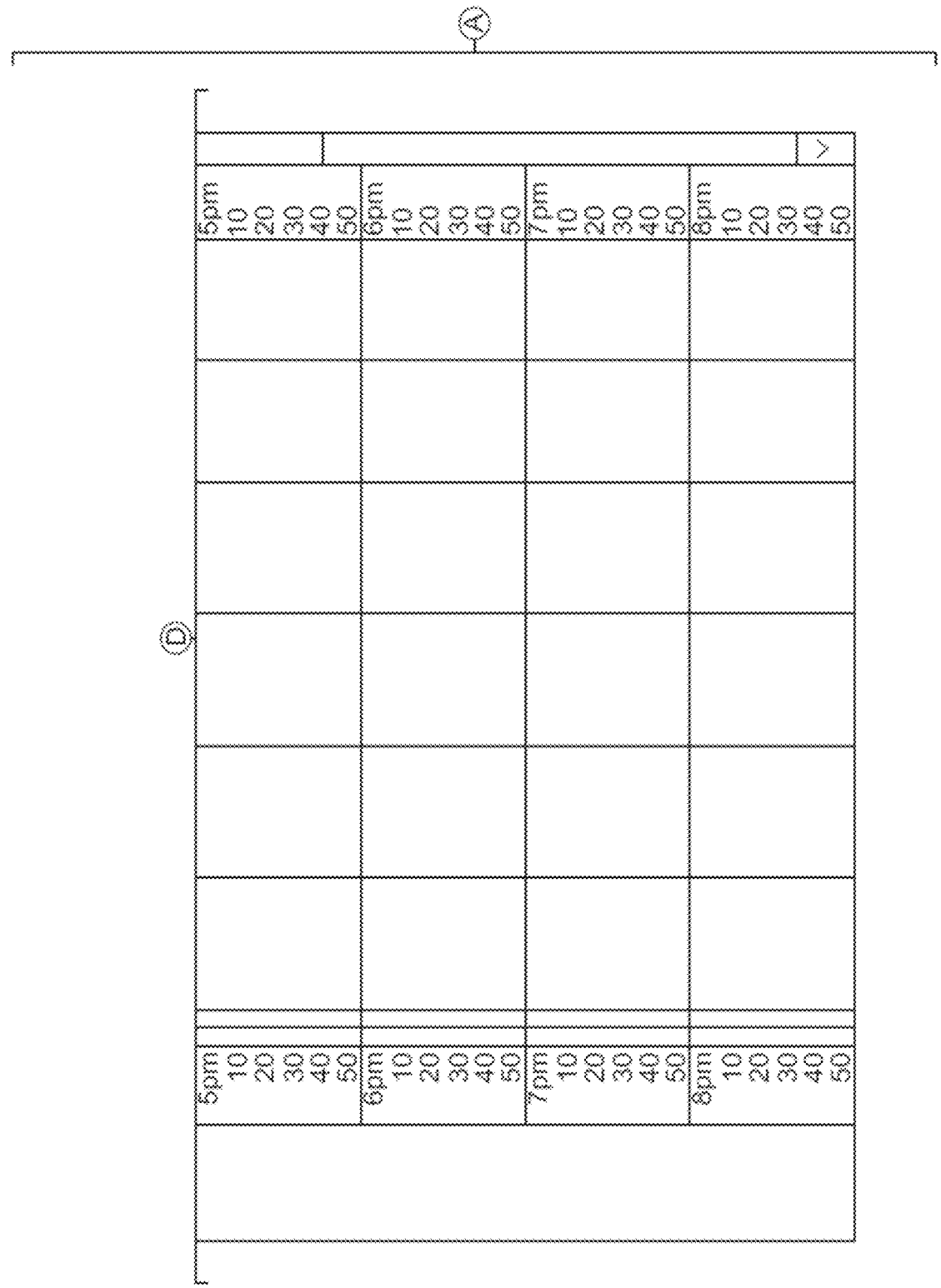
Figure 30:
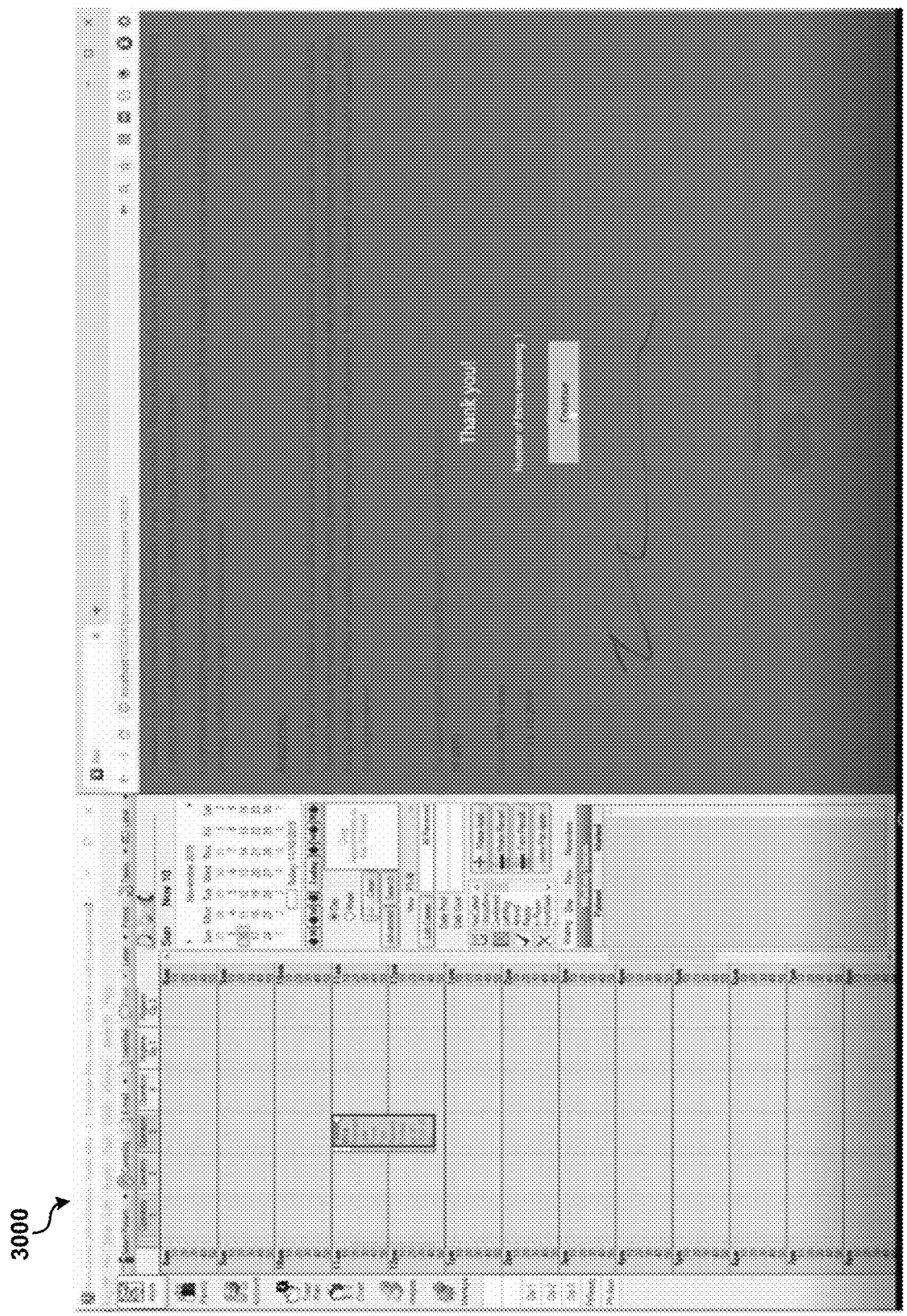
Figure 31:
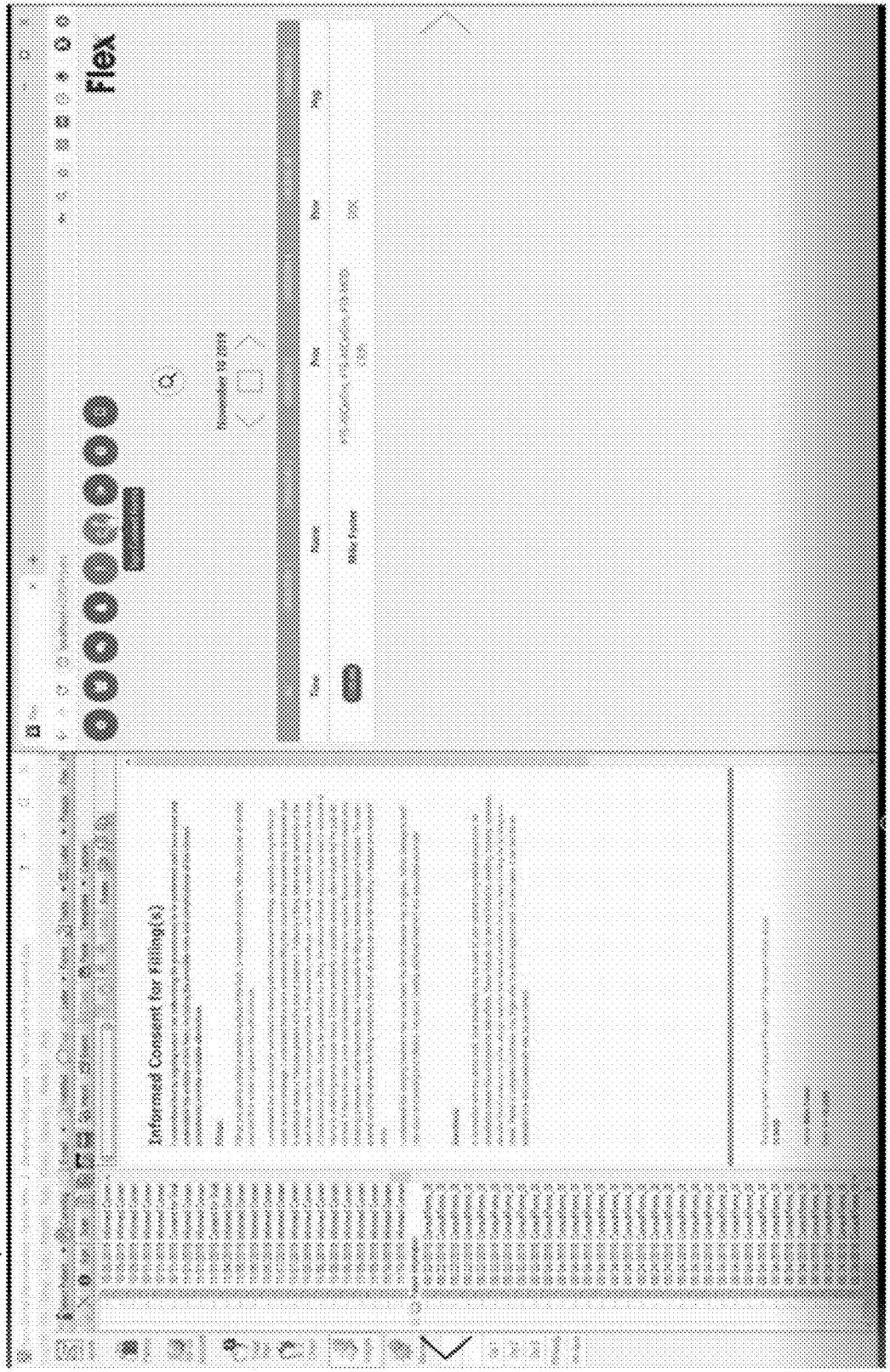
Figure 32:
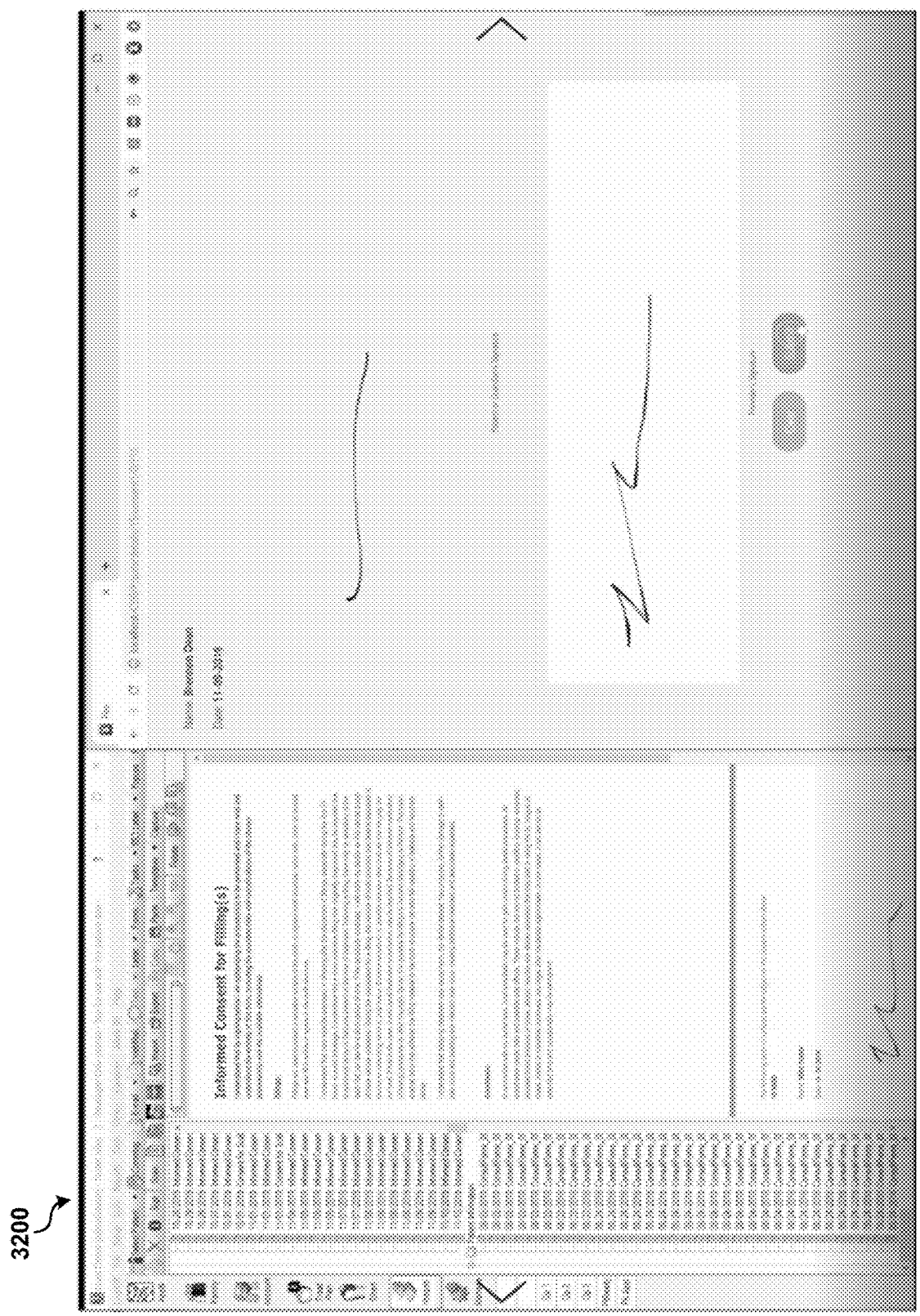
Figure 33:
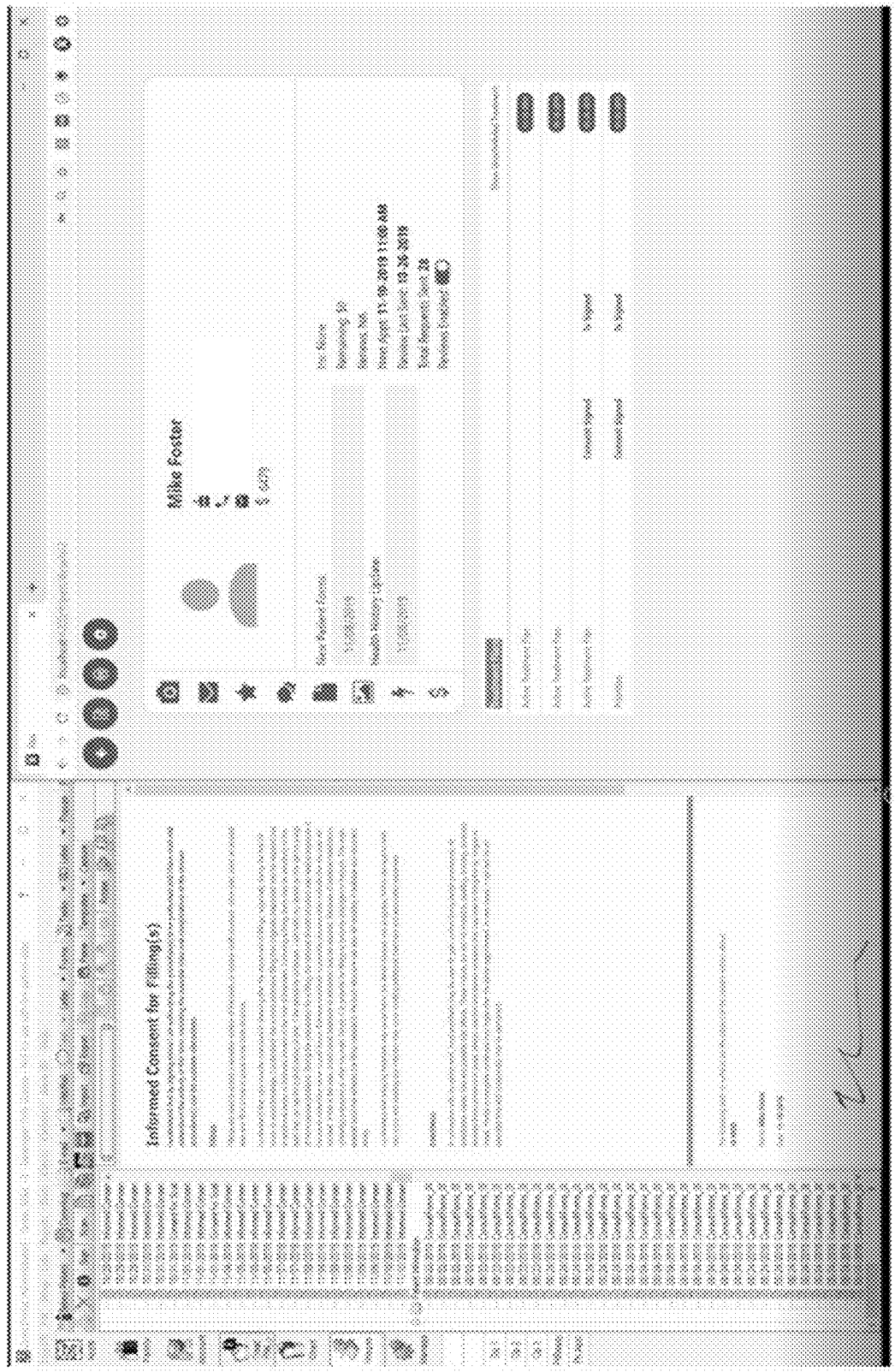

In FIGS. 12-15, additional examples of displayed screens from the web-based platform illustrating dynamic forms are shown. FIG. 12 depicts a screen 1200, FIG. 13 depicts an example of another screen 1300, and FIG. 14 depicts an example of yet another screen 1400, where each of the aforementioned screens 1200, 1300, and 1400 show details related to multiple patients having forms entered into the web-based platform. In FIG. 15, a screen 1500 is illustrated which displays details of a particular patient. Furthermore, FIGS. 16-33 show examples of displayed screens that are particularly related to consent forms that can be dynamically modified and electronically signed by patients and providers (shown in FIG. 32). FIG. 16 illustrates a screen 1600 displaying an example of an interactive consent form. FIG. 17 illustrates another screen 1700 displaying various options related to interactive consent forms. FIG. 18 illustrates a screen 1800 displaying multiple form settings related to interactive consent forms. FIG. 19 illustrates another screen 1900 including form settings related to interactive consent forms. FIG. 20 depicts a screen 2000, FIG. 21 depicts a screen 2100, and FIG. 22 depicts another screen 2200, where each of the screens 2000, 2100, and 2200 is displaying examples of editing an interactive consent form. In FIG. 23 an example of another screen 2300 that includes form settings related to interactive consent forms is shown. FIG. 24 illustrates an example of another screen 2400 that can be used to link a consent form to a treatment, including various treatment codes. FIG. 25 depicts another example of a screen 2500 that can be used to link a consent form to a treatment, including treatment codes. FIG. 26 depicts another example of a screen 2600 that can be used to link a consent form to a treatment, including treatment codes and treatment categories. FIG. 27 depicts another example of a screen 2700 that can related to a consent form. FIG. 28 depicts yet another example of a screen 2800 displaying linked consent forms and associated treatment plans. FIG. 29 depicts an example of a screen 2900 that can be used to enter a consent form linked to a treatment and a particular teeth/surfaces. FIG. 30 depicts an example of a screen 3000 that can be used to sign and submit a consent form. FIG. 31 depicts an example of a screen 3100 displaying an option to sign a consent form for a particular patient. FIG. 32 depicts an example of a screen 3200 that can be used to enter a patient signature, in order to sign a consent form. FIG. 33 depicts an example of a screen 3300 displaying patient details, treatment plans and the associated consent forms for a particular patient. In a busy medical practice, it can be difficult to ensure that all important consent forms are signed by every patient. Similar to the aforementioned dynamic forms, consent forms can be fully customizable forms. Additionally, consent forms are configured to capture digital signatures via a device, such as on an office tablet. Consent forms can also be automatically communicated to a patient's device from the web-based platform, via a SMS or e-mail for example. The web-based platform also supports procedure codes. A procedure code can be linked to a consent form, allowing key treatment details (e.g., tooth number and surfaces) to be included automatically into the form.

Figure 34:
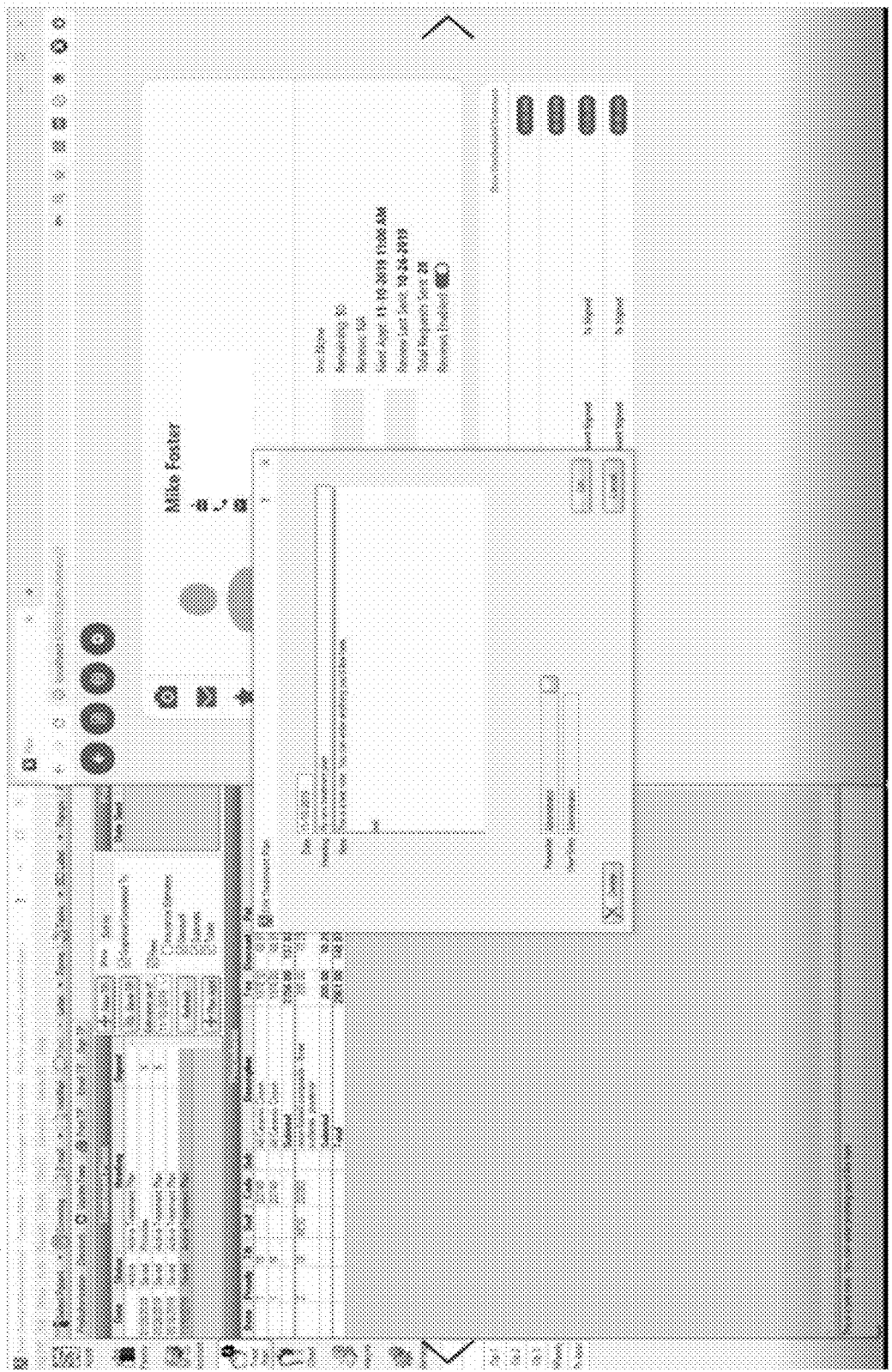
FIGS. 34-38 illustrate examples of displayed screens from the web-based platform associated with an implemented dynamic treatment plan feature, according to one or more embodiments shown and described herein.
Figure 35:

In FIG. 34, an example of a displayed screen 3400 associated with a dynamic treatment plan is shown. As a feature of the integration between the web-based platform and the PMS, any treatment plans that are saved in the PMS will automatically populate in GUIs of the web-based platform. Thus, once a treatment plan is saved in PMS, it can be accessed by any aspect of the web-based platform. For example, once a treatment plan in saved in Open Dental™, it synchronizes with the platform such that treatment plan is available to be shown to patients accessing the platform. As seen in FIG. 35, a summarized view of a treatment plan for a patient can be shown in a screen 3500 displayed by the web-based platform. In some embodiments, the treatment plan can be displayed broken down by appointment, including detailed insurance coverage information, or in a clean and summarized view.

Figure 36:
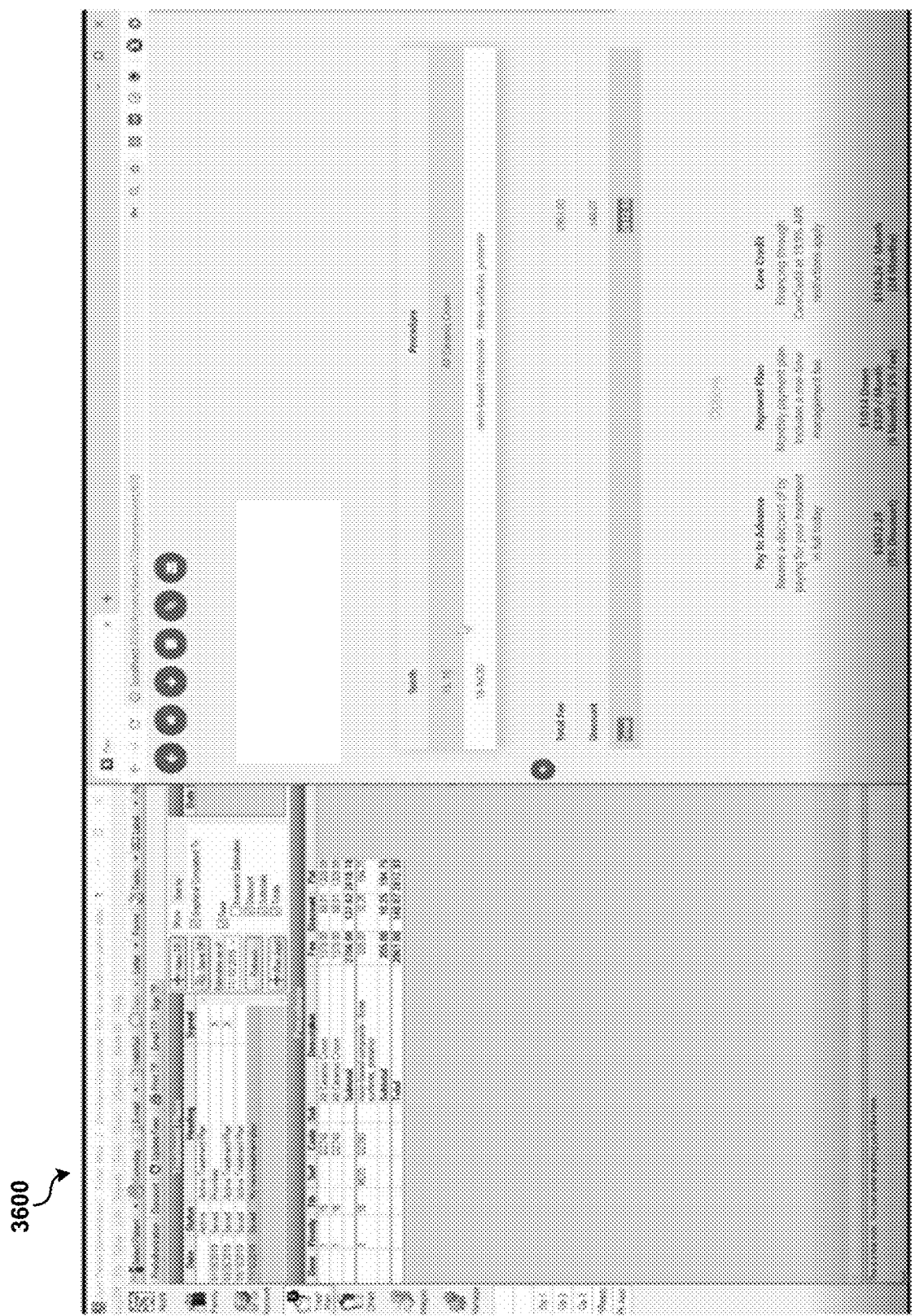
Figure 37:
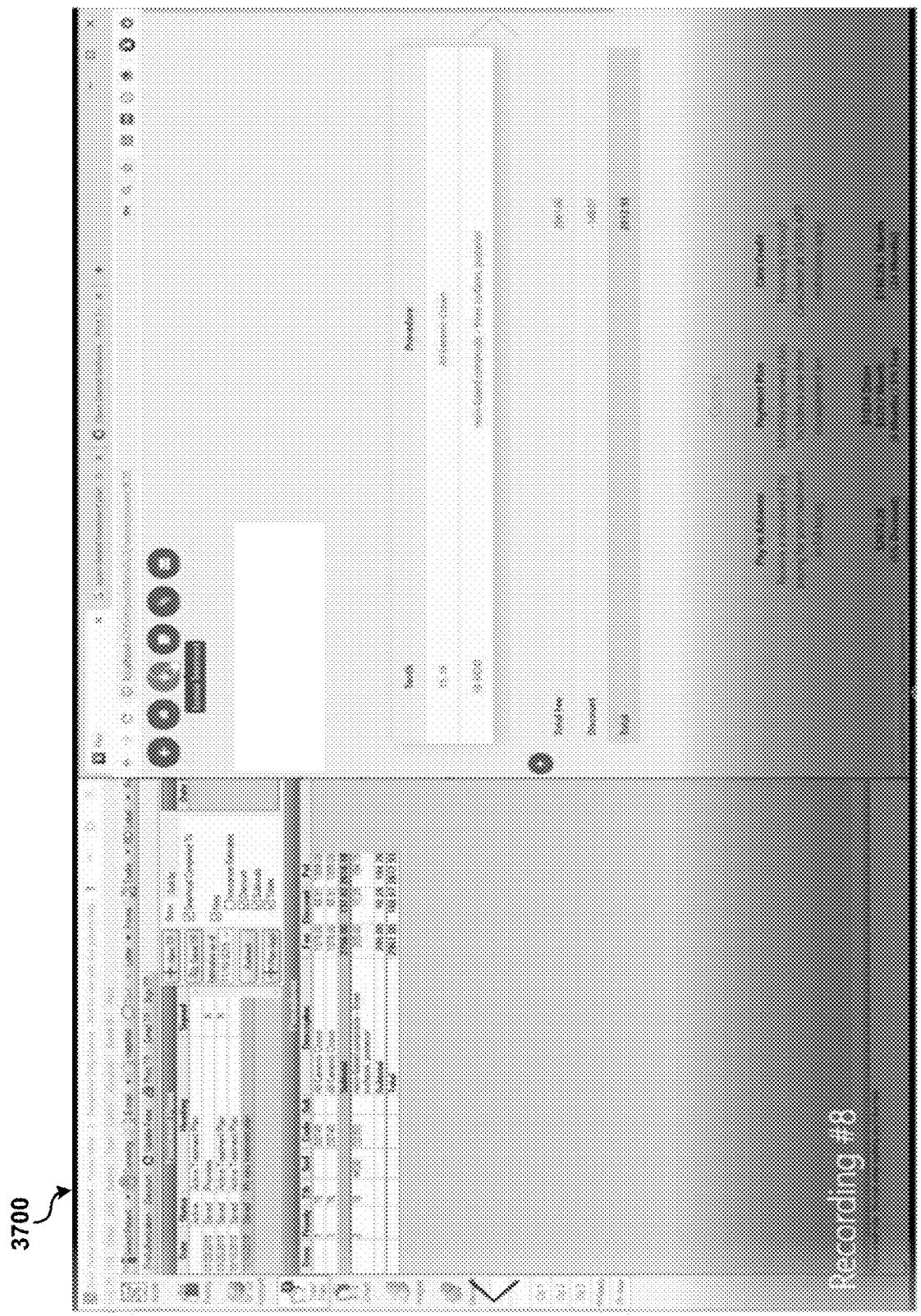
Figure 38:

Now referring to FIG. 36, an example of a screen 3600 that is displayed for presenting the payment option relating to a procedure are shown. Alluding back to the dynamic aspects of the web-based platform, a treatment plan can also by dynamically modified in a manner that is specific to the patient. Data that is irrelevant to the patient corresponding to the treatment plan can be omitted when being displayed. For example, if a user does not have insurance, then only payment options such as "Pay In Advance", "Payment Plan", and "Care Credit" (e.g., payment options that do not require insurance) are included in the treatment plan that is displayed in screen 3600. FIG. 37 includes an example of a screen 3700 that is displayed for presenting itemized treatments in a treatment plan including various procedures, and the associated payment options for the treatment plan. FIG. 38 includes an example of a screen 3800 that displays payment data including "fee", "discount", and "new price" relating to each of the various procedures of a shown itemized treatment.

Figure 39:
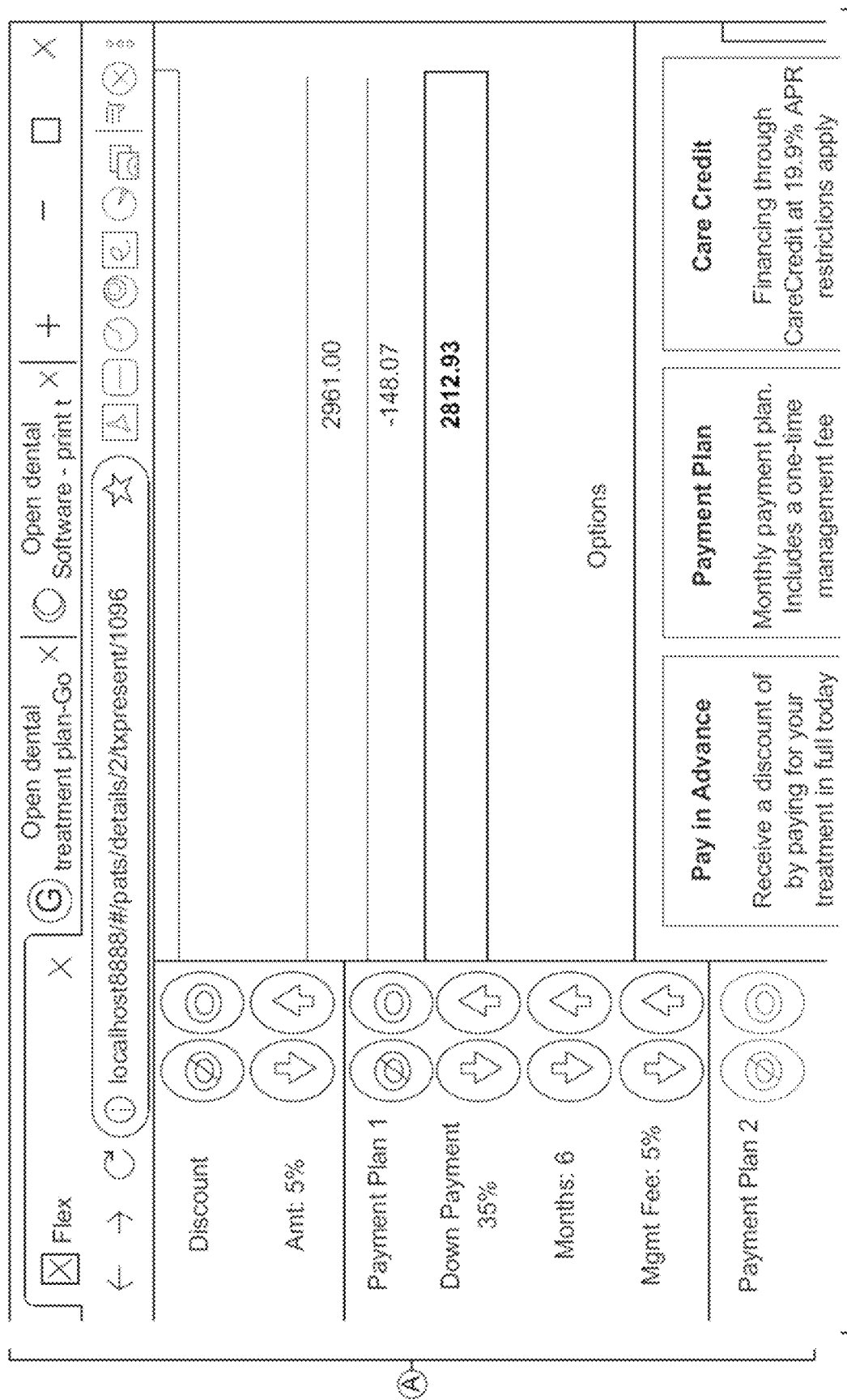
FIGS. 39-47 illustrate additional examples of displayed screens from the web-based platform associated with an implemented dynamic treatment plan feature, including payment options, according to one or more embodiments shown and described herein.
Figure 39:
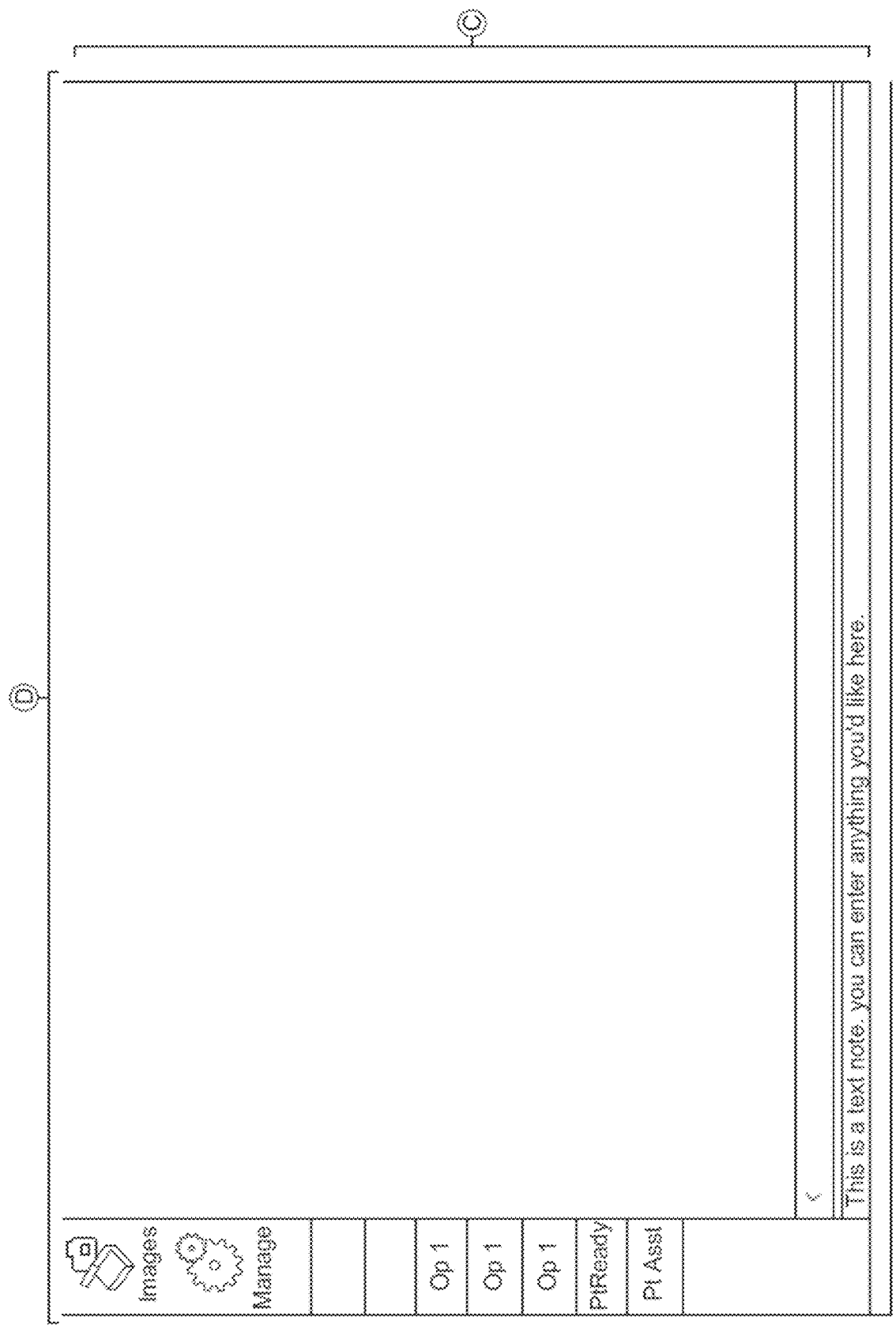
Figure 39:
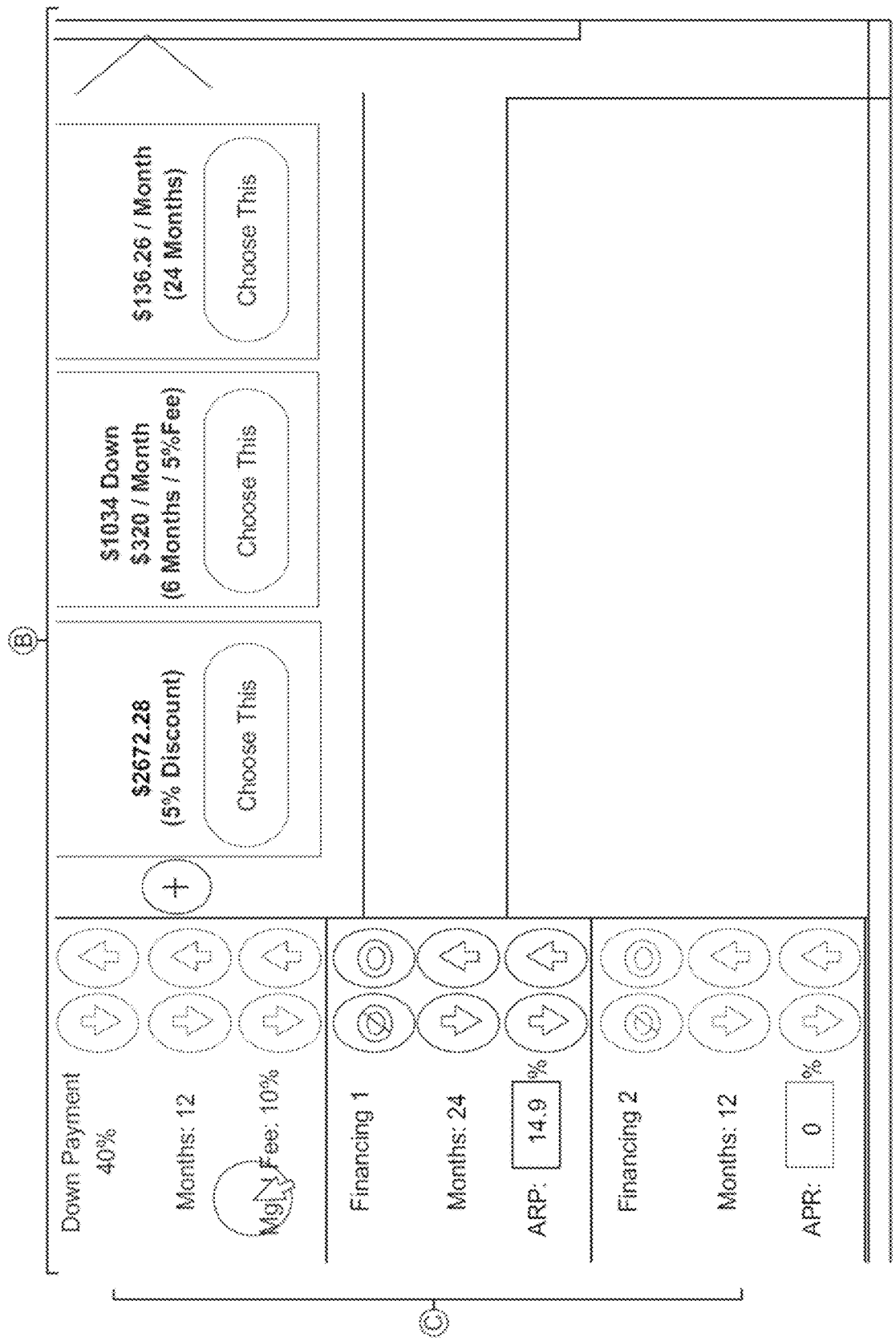

In addition, the payment options are highly customizable. A dental office can include, omit, and/or adjust payments options as deemed necessary. The web-based platform allows a dental office to edit payment options, such as updating the description and the payments amounts. FIG. 39 depicts a screen 3900 that can be used to enter adjustments to customize payment options for a treatment plan.

Figure 40:
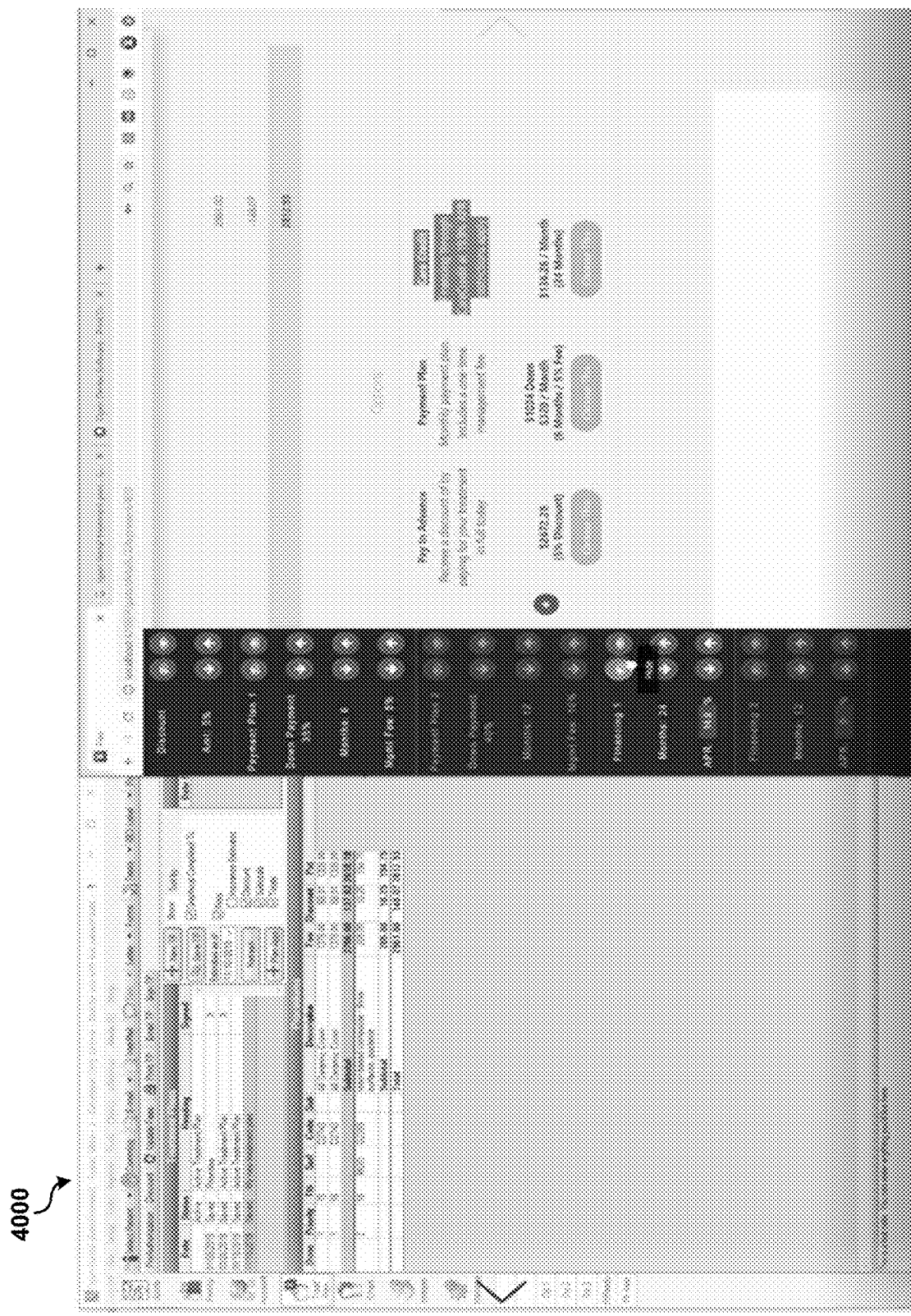
Figure 41:
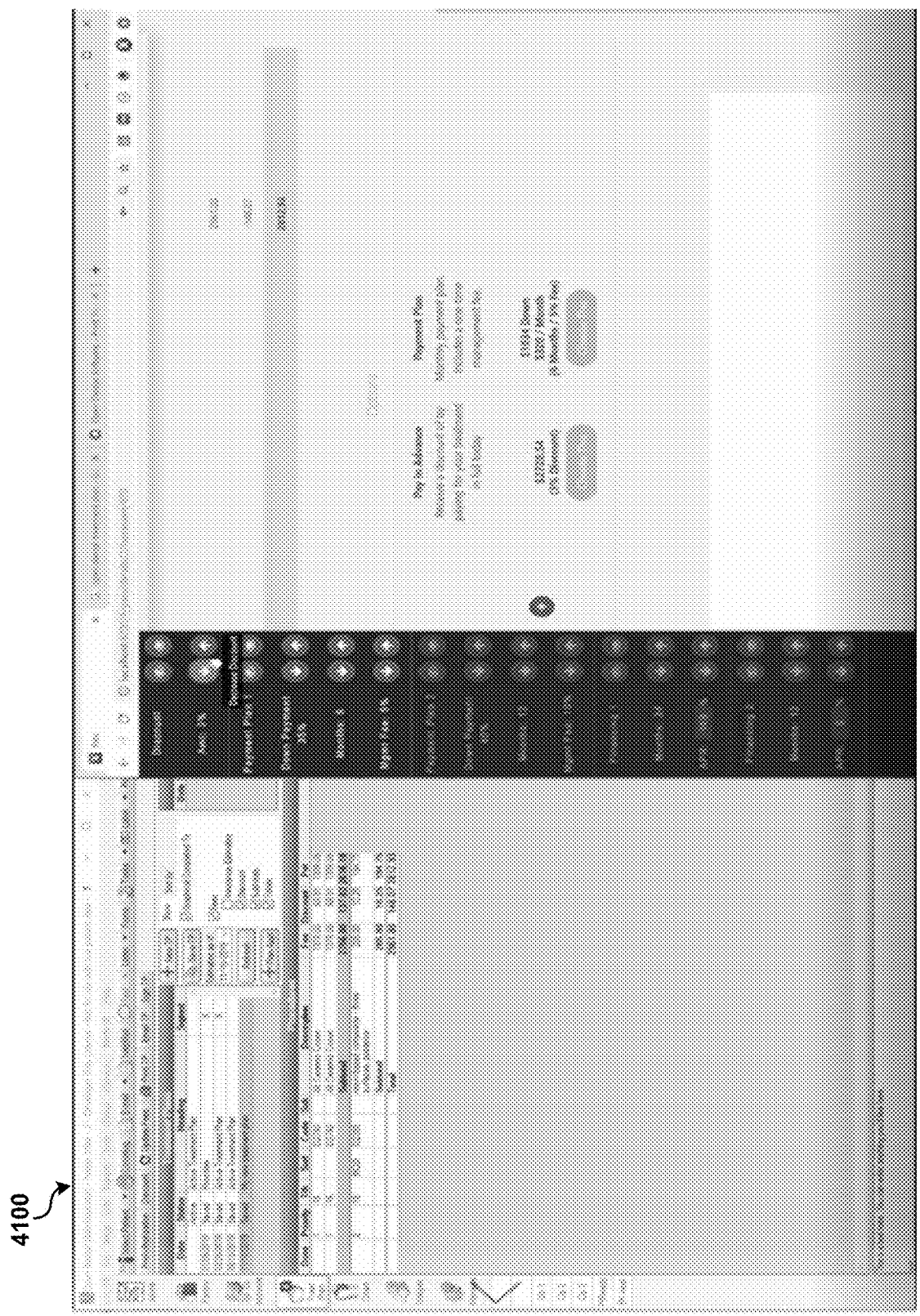

Referring to FIG. 40, screen 4000 shows that payment options including a "Care Credit" option, which would allow a user to select for their payment to be financed by a third-party company. However, the dental office may wish to remove financing as an option for some patients. In this case, the payment options can be customized for a particular user, removing that option when being displayed to a patient that may fail to meet that criteria. In FIG. 41, an example of a screen 4100 is shown in this scenario, where that option is not displayed, being removed for that patient.

Figure 42:
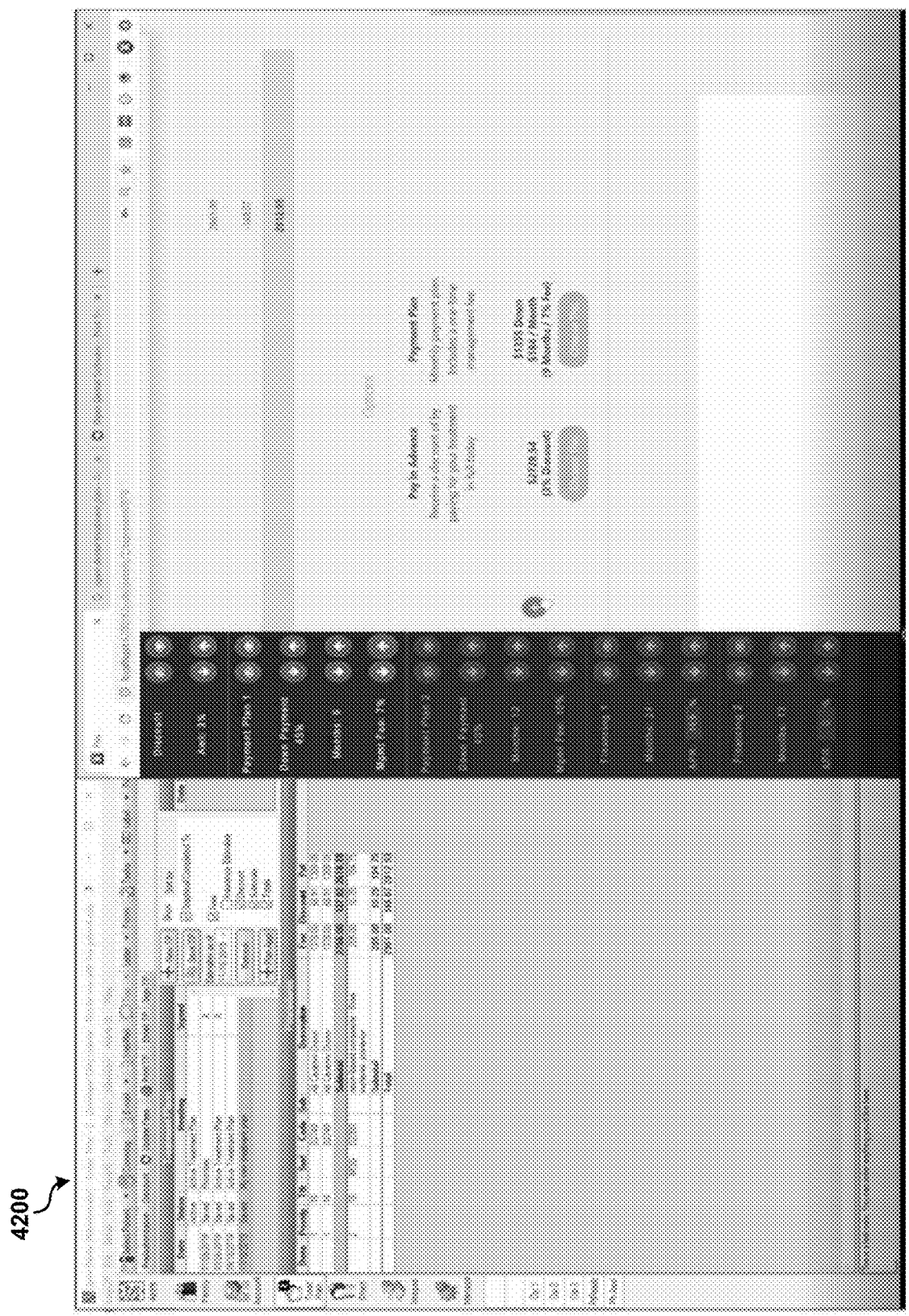
Figure 43:
Figure 44:
Figure 45:
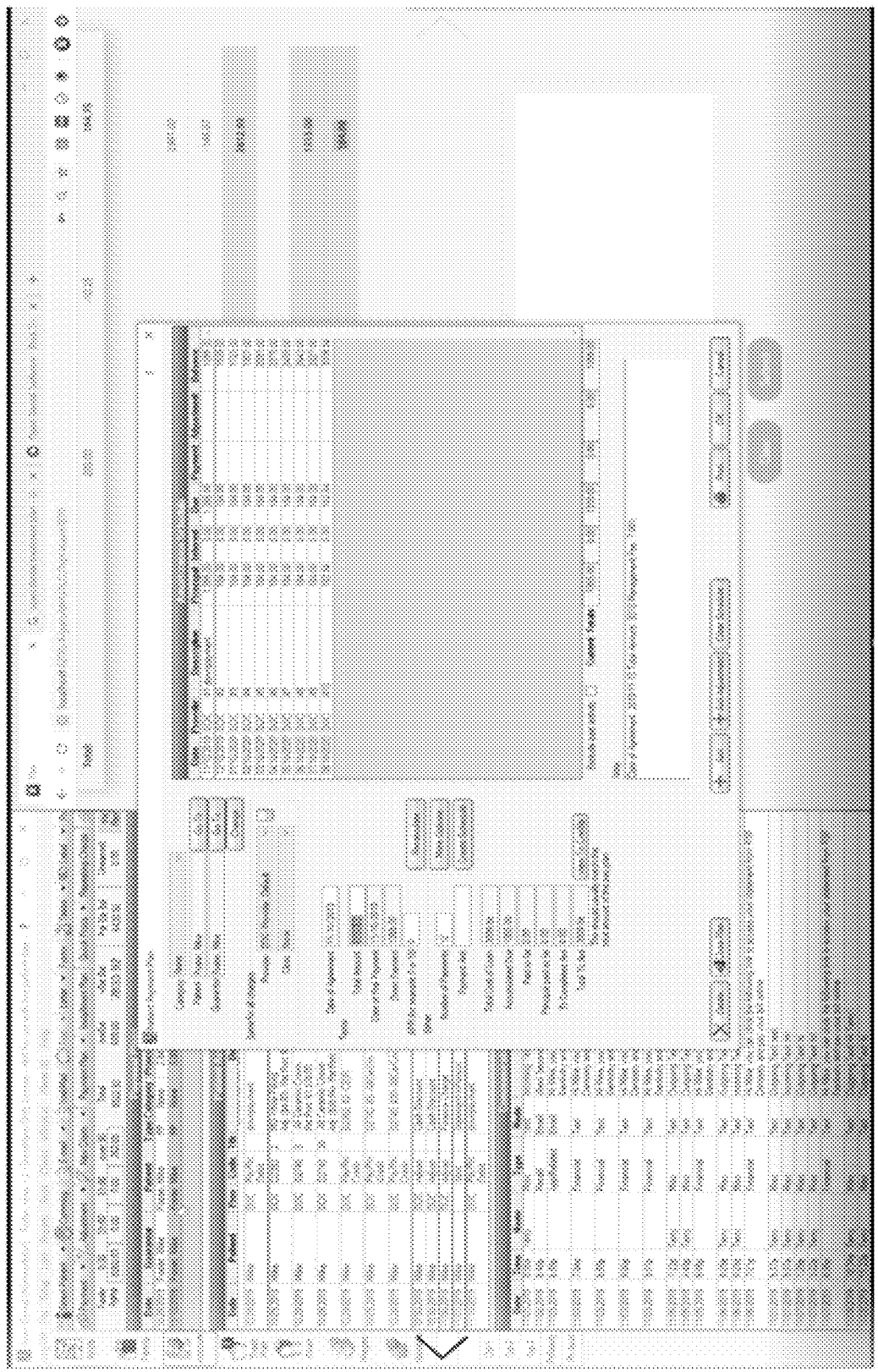
Figure 46:
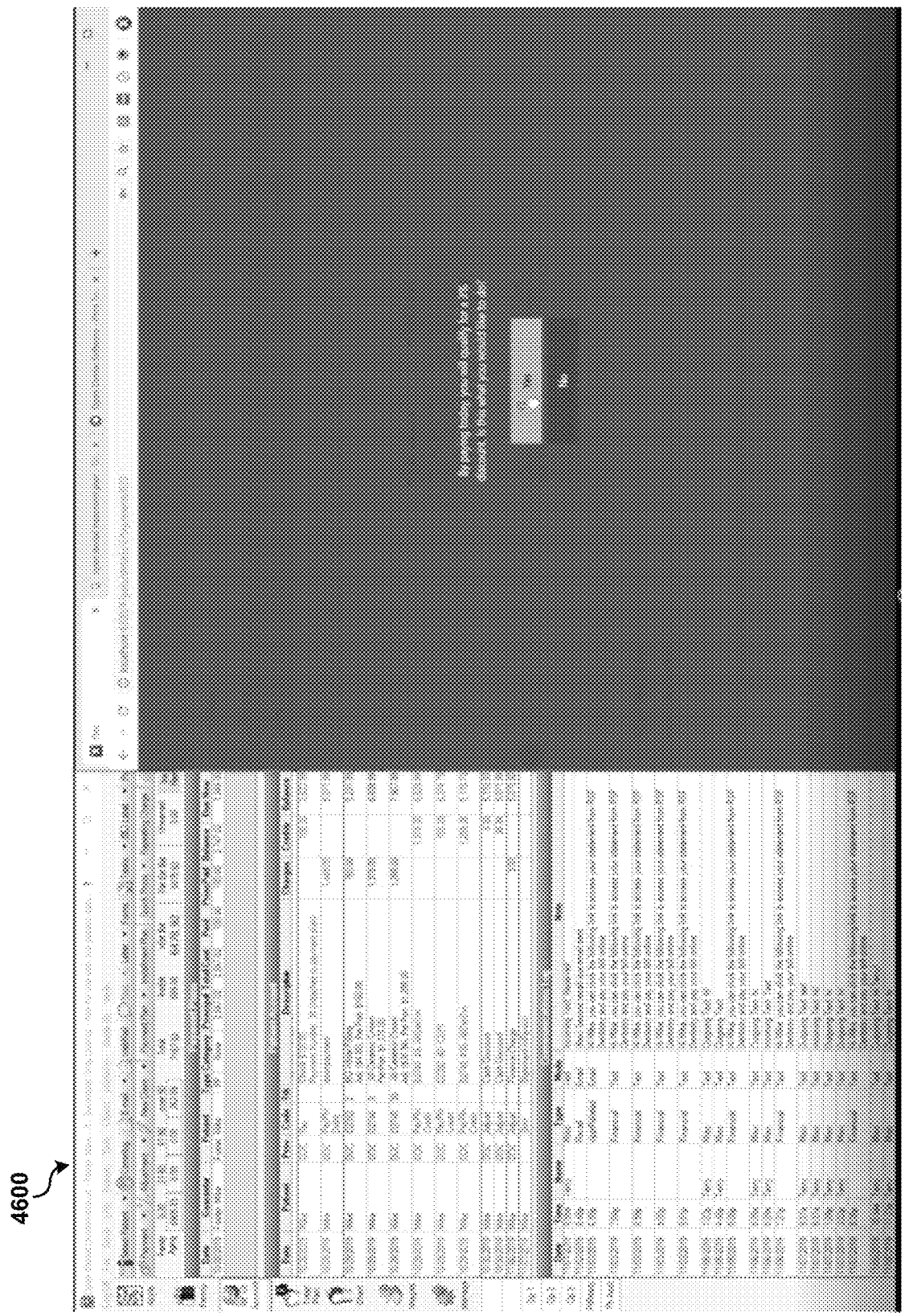
Figure 47:
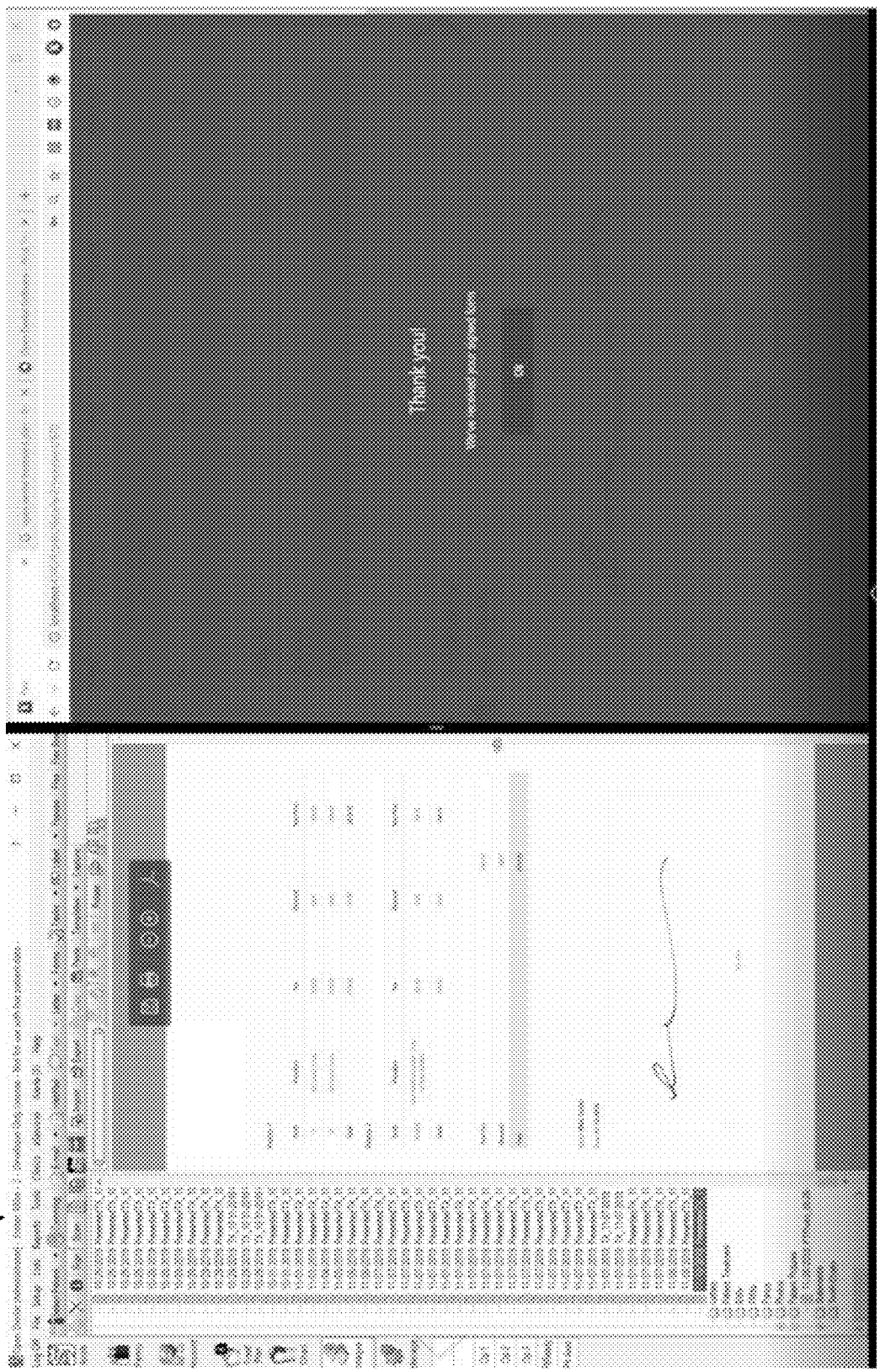

FIGS. 42-47 show examples of screens that may be displayed by the web-based platform, as a result of a patient selecting a particular payment option in their treatment plan. According to some embodiments, once a patient selects their payment choice, the treatment plan will be automatically updated on the web-based platform and the PMS. Once finished, that specific treatment plan can be marked as signed in the PMS, and automatically stored as an image (e.g., PDF), for example within a folder for treatment plan forms supported by the platform. FIG. 42 depicts a screen 4200 for choosing payment options for a treatment plan. FIG. 43 depicts a screen 4300 that can be used to submit the selected payment options for a treatment plan. FIG. 44 depicts a screen 4400 that can be used for a patient to sign for their payment option. FIG. 45 depicts a screen 4500 displaying a patient payment plan, including a amortization schedule. FIG. 46 depicts a screen 4600 displaying an example of a discount relating to the patient payment plan. FIG. 47 depicts a screen 4700 notifying that a signed form for the patient payment plan has been received.

As an additional feature of the web-based platform, a patient can submit a payment, based on their selected payment options through the platform. The web-based platform allows a user to pay directly from a treatment plan, a device associated with the dental office system (e.g., tablet used in the dental office), or from their device via a patient-specific statement. As previously described, a feature of the web-based platform enables patient-specific statements to be securely transmitted to the patient's device (e.g., text or email). As seen, FIG. 69 illustrates an example of a statement 6900 for the treatment plan including a payment option (shown as "Pay In Advance—5% Discount") that may be displayed on the patient device. In the example of FIG. 69, the statement 6900 can include: one or more treatments; the corresponding procedure code; the treatment total; current balance; office discount; a total; an amount due now; and the payment option to be viewed by the patient. For example, the statement 6900 shows that the patient (shown as "Mike Foster"), at least one treatment (shown as "All Ceramic Crown") and the corresponding procedure code (shown as "D2740"). Using secure URLs that are automatically generated by the platform (and embedded into the text or email), a patient can access a GUI which allows them to securely submit their payment (e.g., no online portal or special logins required). Once the patient's payment is made, the transaction details can be posted in real-time to the patient's account on the web-based platform and the PMS (which can includes the individual procedure allocations).

Figure 48:
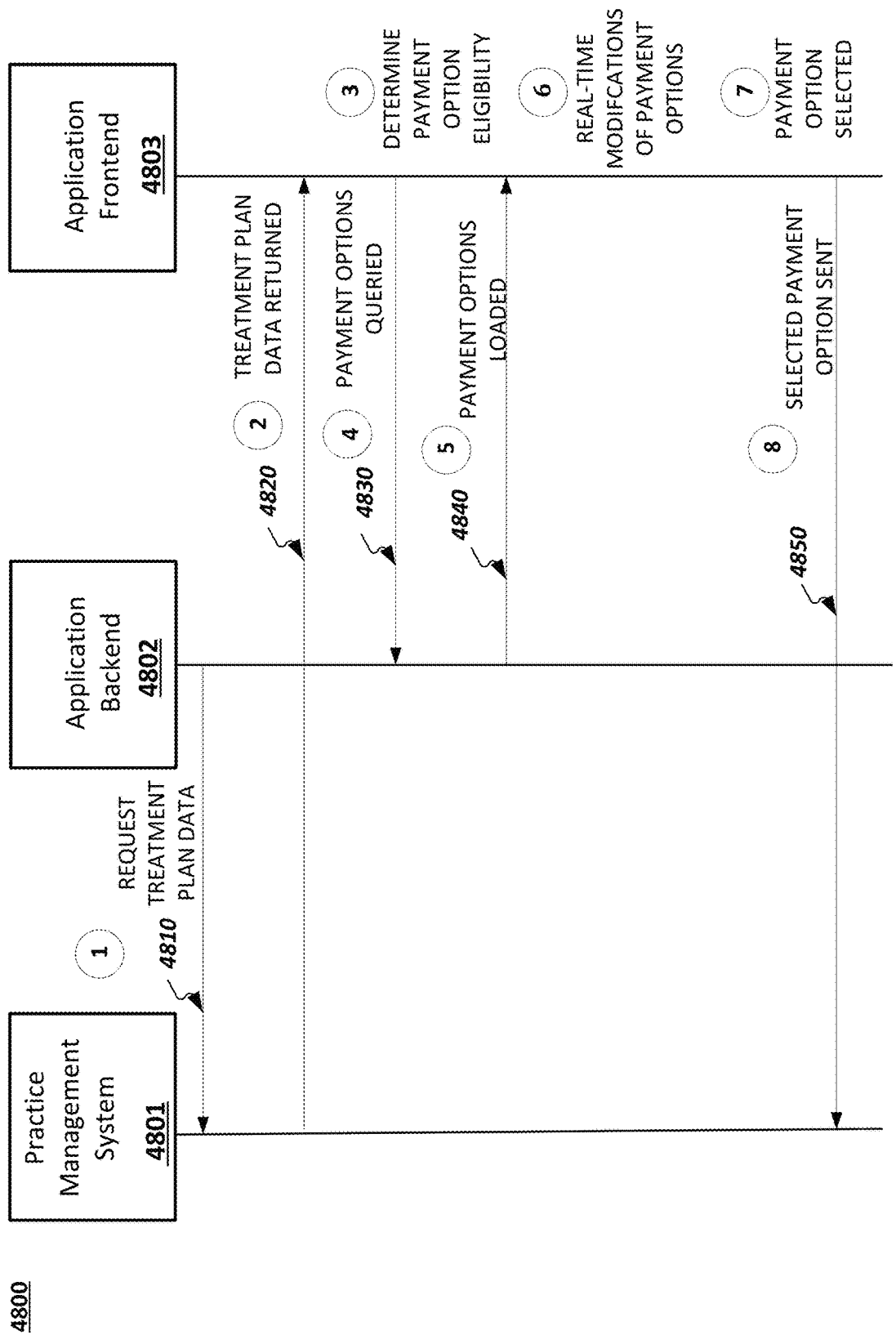
FIG. 48 illustrates an example of a message flow related to the dynamic treatment plan option of the web-based platform, according to one or more embodiments shown and described herein.

Now referring to FIG. 48, a message flow 4800 associated with the exchange of data that may occur while creating and communicating a treatment plan is depicted. The message flow 4800 can begin in exchange 4810, where the web-based platform backend 4802 requests a treatment plan from the PMS 4801. The request can involve the web-based platform backend 4802 making a call to the PMS 4801 for the data.

Then, in exchange 4820, the data returned form the PMS 4801 is transmitted to the web-based platform frontend 4803. In response to receiving the data from the PMS 4801, the web-based platform frontend 4803 can determine the payment option eligibility. To make this determination, the web-based platform frontend 4803 can query the available predefined payment options against the web-based platform backend 4802 in exchange 4830. Information for the specific patient and the specified treatment plan can be compared against those predefined parameters, to determine eligibility of each patient record.

Thereafter, in exchange 4840 the available payment options can be loaded into the web-based platform frontend 4803. After the payment options are loaded, real-time modifications of the payment options can be made via the web-based platform frontend 4803, in accordance with the dynamic aspects of the treatment plan feature (as described above). In some cases, a GUI can be provided to adjust the available payment options in real-time. Current payment options can be edited, new payment options can be added, or existing payment option removed to tailor the options to the specific patient. In exchange 4850, the payment option can be selected by the patient, as supported by the web-based platform frontend 4803. The payment option can be selected by the patient, and the option is sent to PMS 4801 to be linked to the account (or record) on the PMS 4801 that corresponds to that patient. Then, the account is setup in the PMS 4801 based on the received payment option data. For example, discounts can be applied, or a payment plan is created for that particular patient.

According to the embodiments, the disclosed web-based platform serves as an online facilitator of payment transactions between a payer (e.g., the patient) and a payee (e.g., the dental office). For example, when a dental patient purchases goods and/or services related to a dynamic treatment plan that has been automatically generated by the web-based platform, the application can also be used as the platform for billing and payment by the dental office. In other words, the web-based platform has billing, and payment capabilities integrated on the platform in a manner that supports payment transfer between patients and the dental office. For example, during a payment process, the patient can select a payment option for a dynamic treatment plan. The web-based platform can provide an HTML form to the patient that is hosted on its application backend 4802 (e.g., server). The patient can use this form to enter their payment details (e.g., credit card, debit card, or electronic funds transfer).

Subsequently, the data (in the form) is transmitted to the dental office in order to process payment. In some cases, the payment details may be entered and stored by the PMS 4801, and transferred to a payment service provider (e.g., banking system) for clearing by the application backend 4802.

As previously described, the web-based platform includes an application backend 4802 and an application frontend system 4803. The application backend 4802 can support one or more payment transactional applications and the application front end 4803 can support the online (or web-based) applications used primarily by the dental office, such as generating the dynamic treatment plan. The application backend 4802 may be implemented using a computer processing device, for example a processor-based server.

A patient may interact with the application frontend 4803 using their own device, such as a laptop or smartphone. For example, the patient can use their smartphone to select a payment option related to dental services communicated by the application frontend 4803 and further to submit payments for that payment option online to ultimately be processed by the application backend 4802. Accordingly, by using the web-based platform the patient does not need to be physically present in the dental office in order to or sending in paper-based payments by mail, which is typically the case in many conventional dental office systems. As previously described, a patient can interact with the web-based platform system using any of a variety of technologies, such as a personal computer, a cellular phone or smartphone, and the connection can be made over any kind of computer network (e.g., the Internet).

The web-based platform can facilitate payment between the patient and the dental office via the application frontend 4803 and the application backend 4802 components of the platform. The patient can have an account registered with the PMS 4801 that can also be used in the payment transaction (e.g., maintaining record of payments).

The application frontend 4803 can be implemented using object-oriented programming language, such as a JAVA-based application. The application backend 4802 can be implemented as a customer relationship management (CRM) backend system based on a high-level programming language. For communication within or by the application backend 4802, Web Services can be used. For communication between the application frontend 4803 and the application backend 4808 objects such as a remote function calls (RFCs) can be used.

In an example, the patient can receive an electronic invoice (or statement) on their patient device from the application frontend 4803. In some cases, the electronic invoice is automatically generated based on the details of the payment option selected by the patient. For instance, the patient can receive an SMS message on their smartphone including a Hypertext Transfer Protocol (HTTP) link to submit payment on their dynamic treatment plan online. The HTTP link can access a webpage that redirects the patient to a web-based form on the application backend 4802. There, patient enters the specific payment method for a payment transaction (e.g., credit card, debit card, or electronic funds transfer). After the payment is processed and cleared, confirmation from the patient's payment service provider (e.g., banking system) may be received by the application backend 4802. The application backend 4802 can thereby clear the payment and send a notification of the payment transaction (e.g., identification and status) to the PMS 4801 to record that payment has been successfully submitted by the patient. Also, the application backend 4802 can generate additional details of the transaction. After fulfillment and invoicing of the payment, the application backend 4802 can send the details of the payment transaction to update the corresponding record for the patient in the PMS 4801. After the payment is settled, the PMS 4801 can automatically match the payment transaction with the patient's record for storage (and later retrieval). Thus, any sensitive, private, or financial information relating to the patient is not maintained at the application backend 4802 itself. As alluded to above, the application backend 4803 acts as a pass-thru that handles data in a transient manner (e.g., not persistently storing data), even in payment processing. As a result, the web-based platform implements payment processing in a manner that circumvents the risk of the patient's financial information being vulnerable to cybersecurity attacks (e.g., hacking, information theft, etc.).

Figure 49:
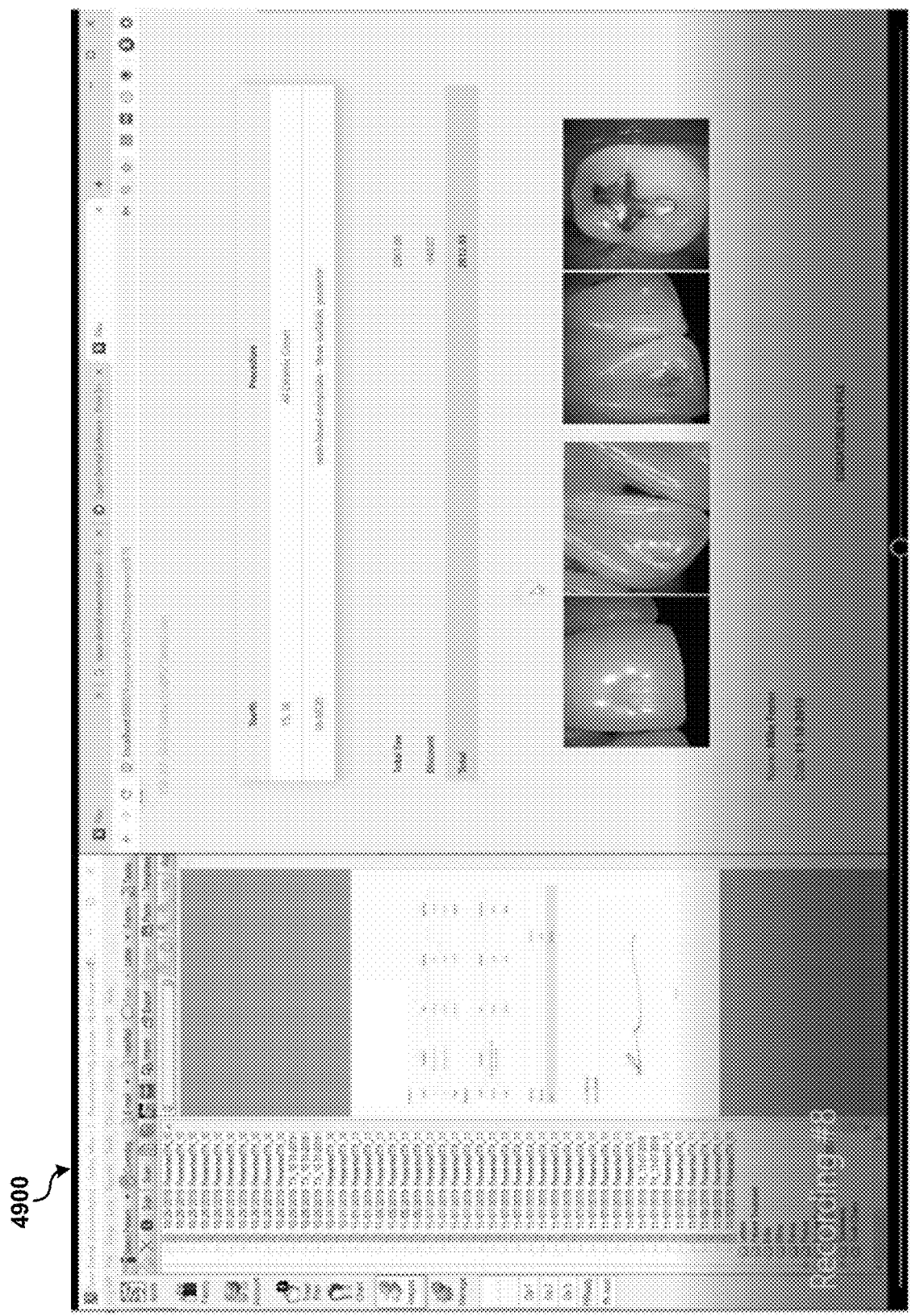
FIGS. 49-59 illustrate additional examples of displayed screens from the web-based platform associated with an implemented dynamic treatment plan feature, according to one or more embodiments shown and described herein.
Figure 50:
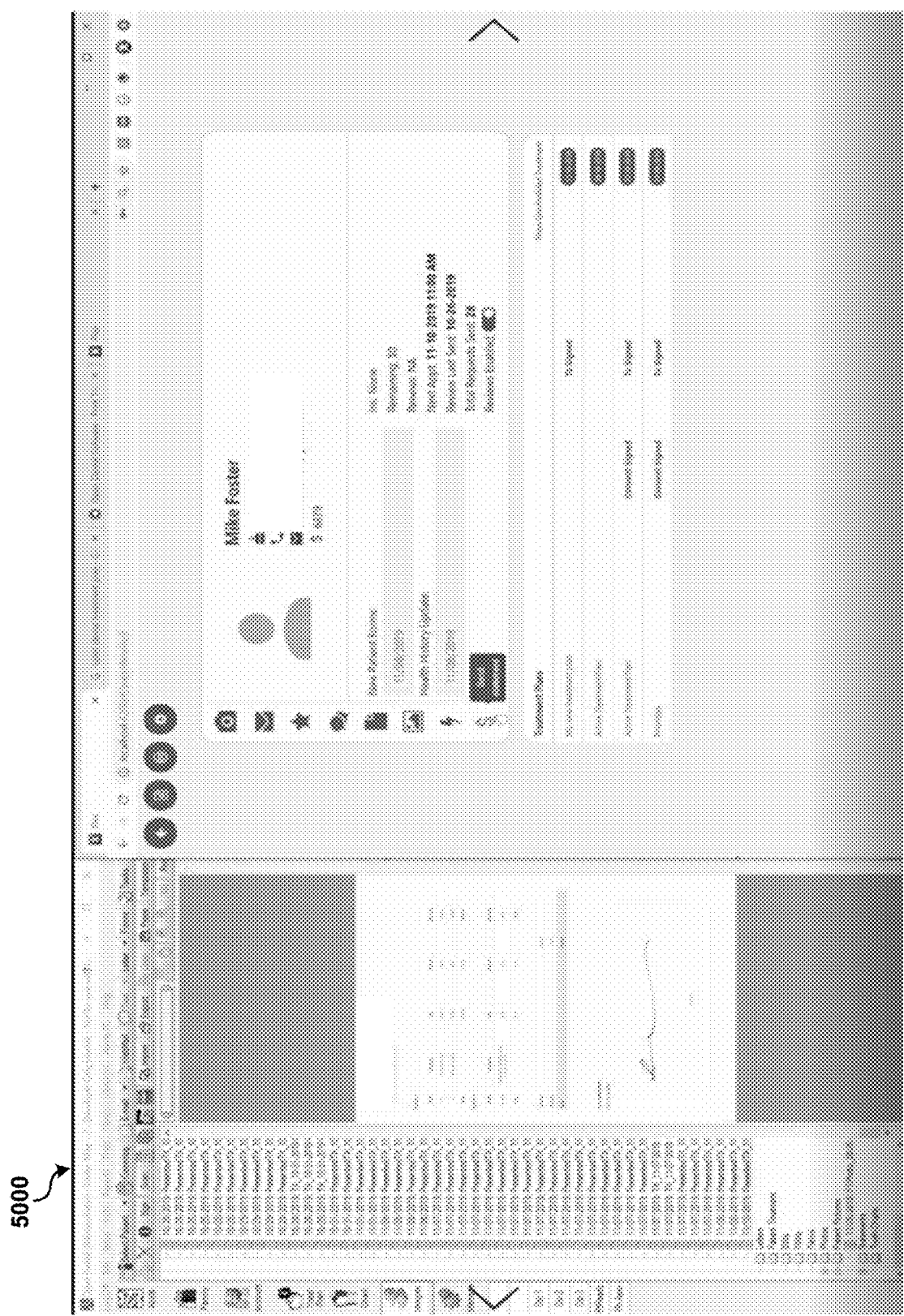
Figure 51:
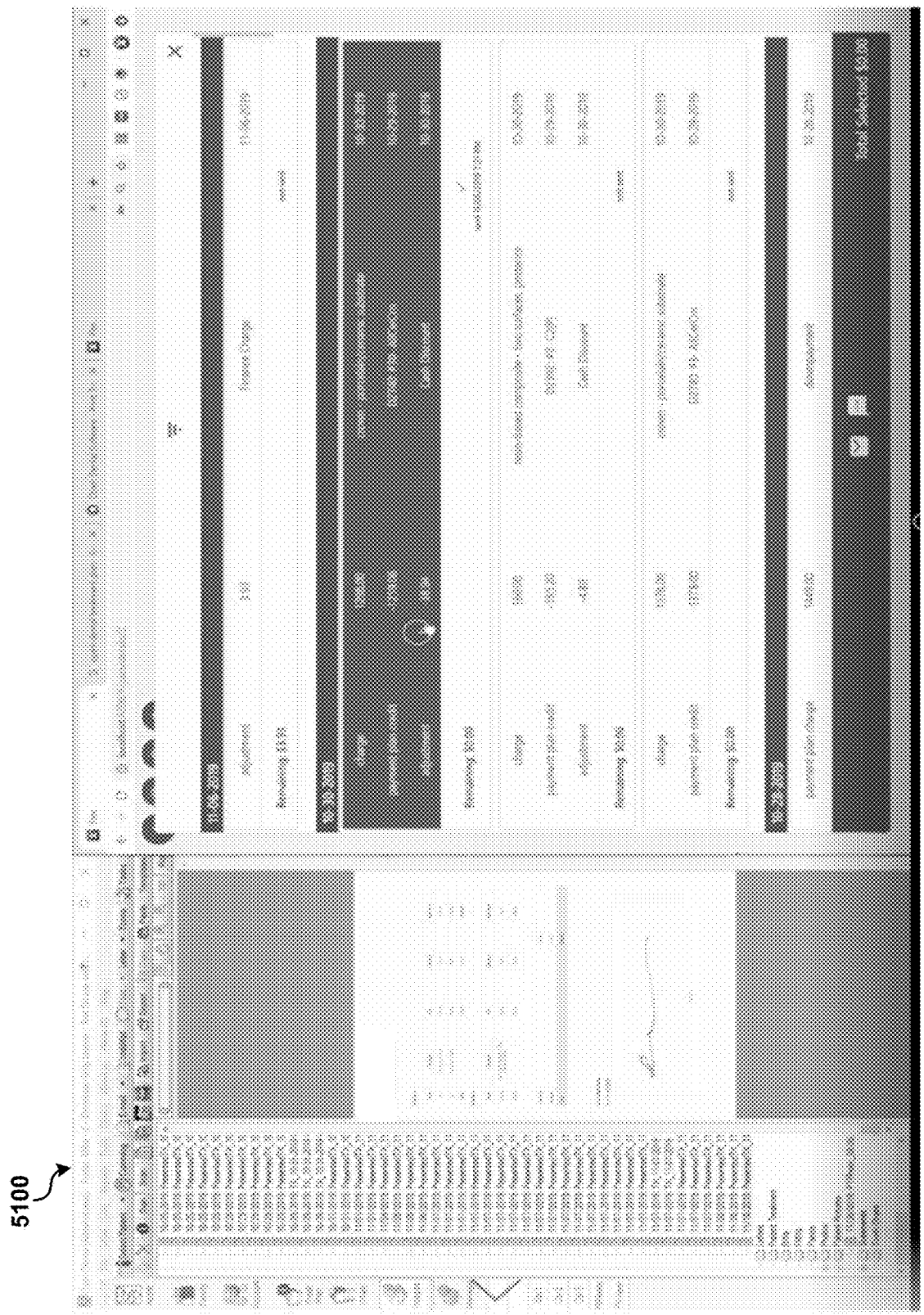
Figure 52:
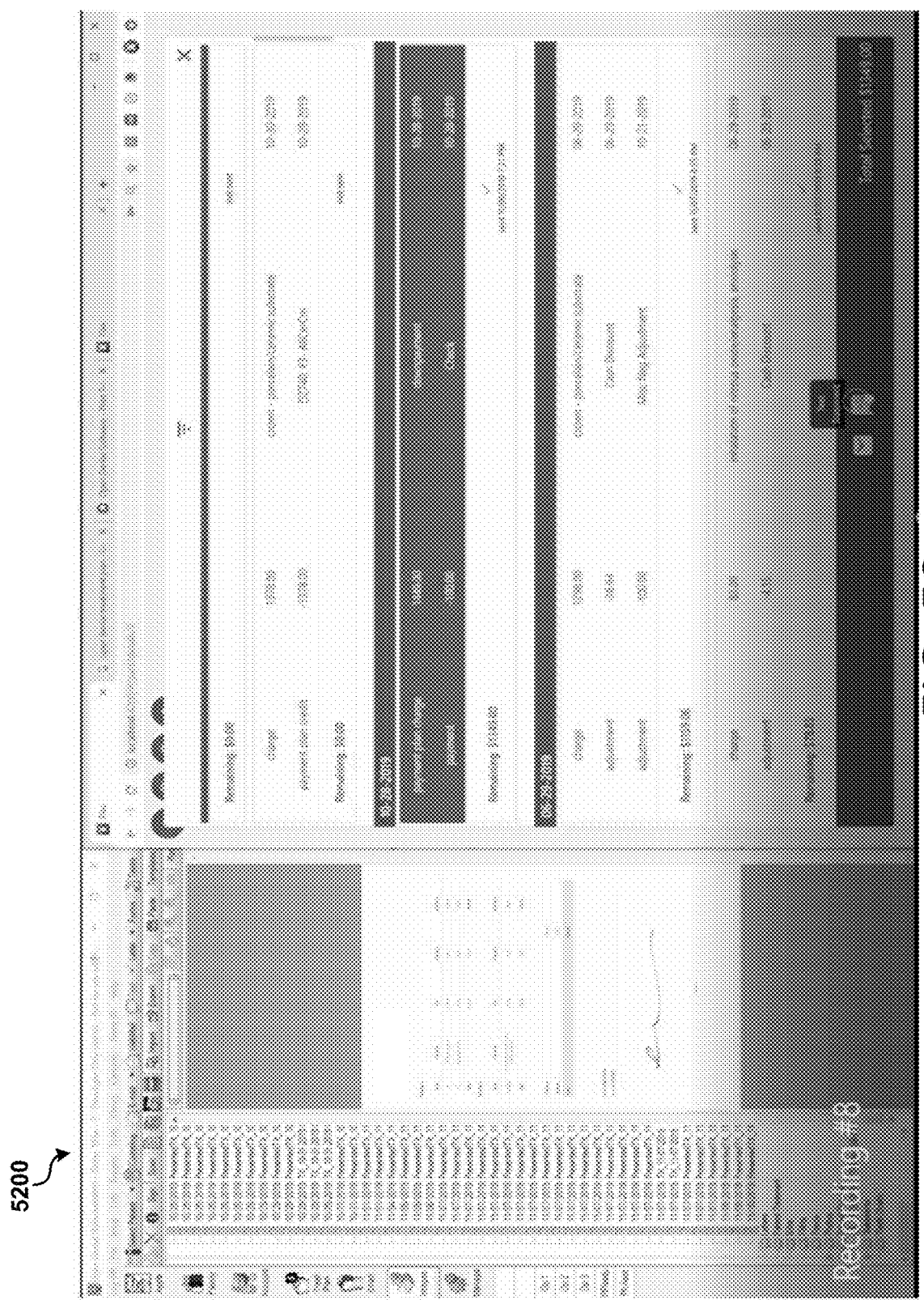
Figure 53:
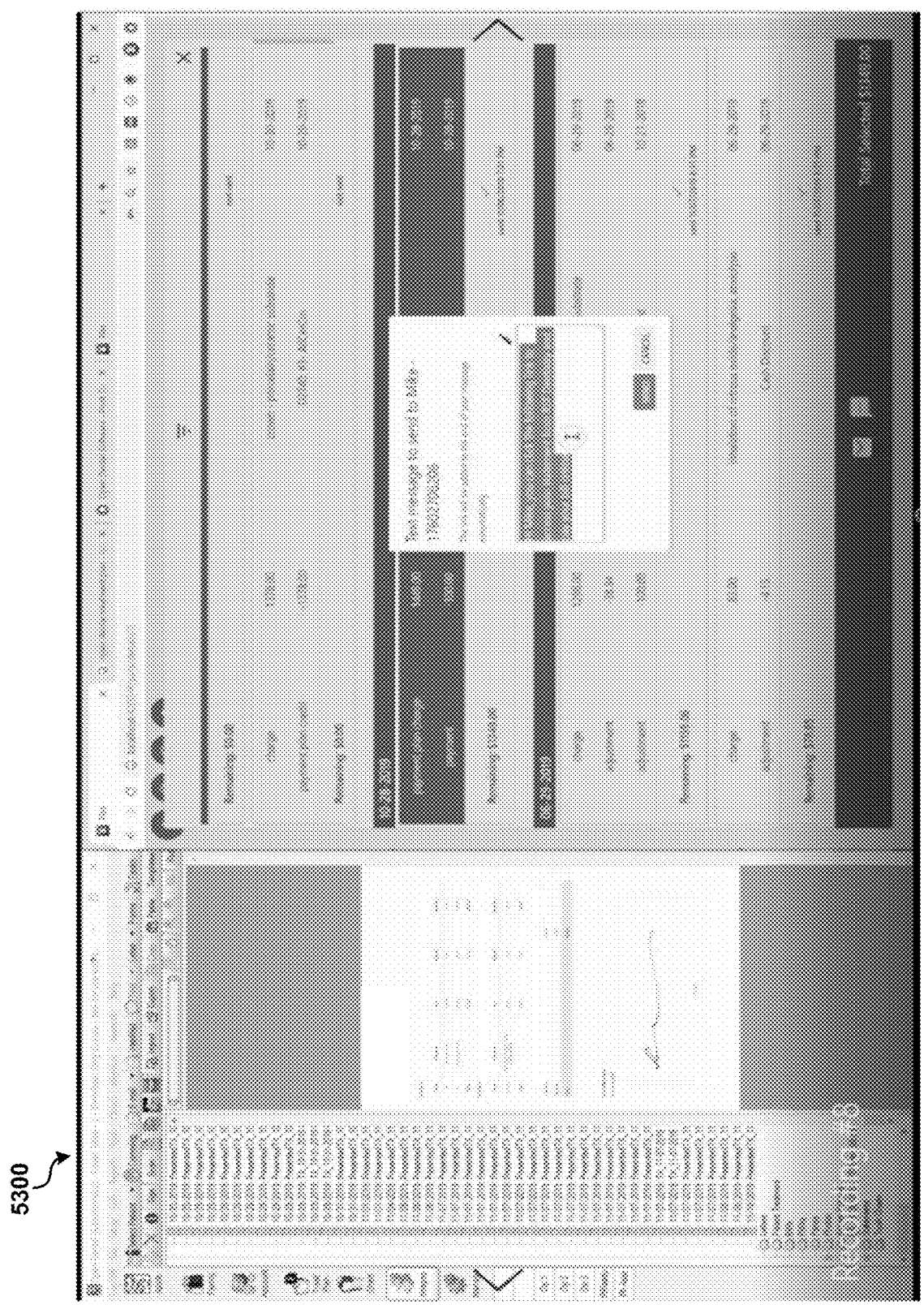
Figure 54:
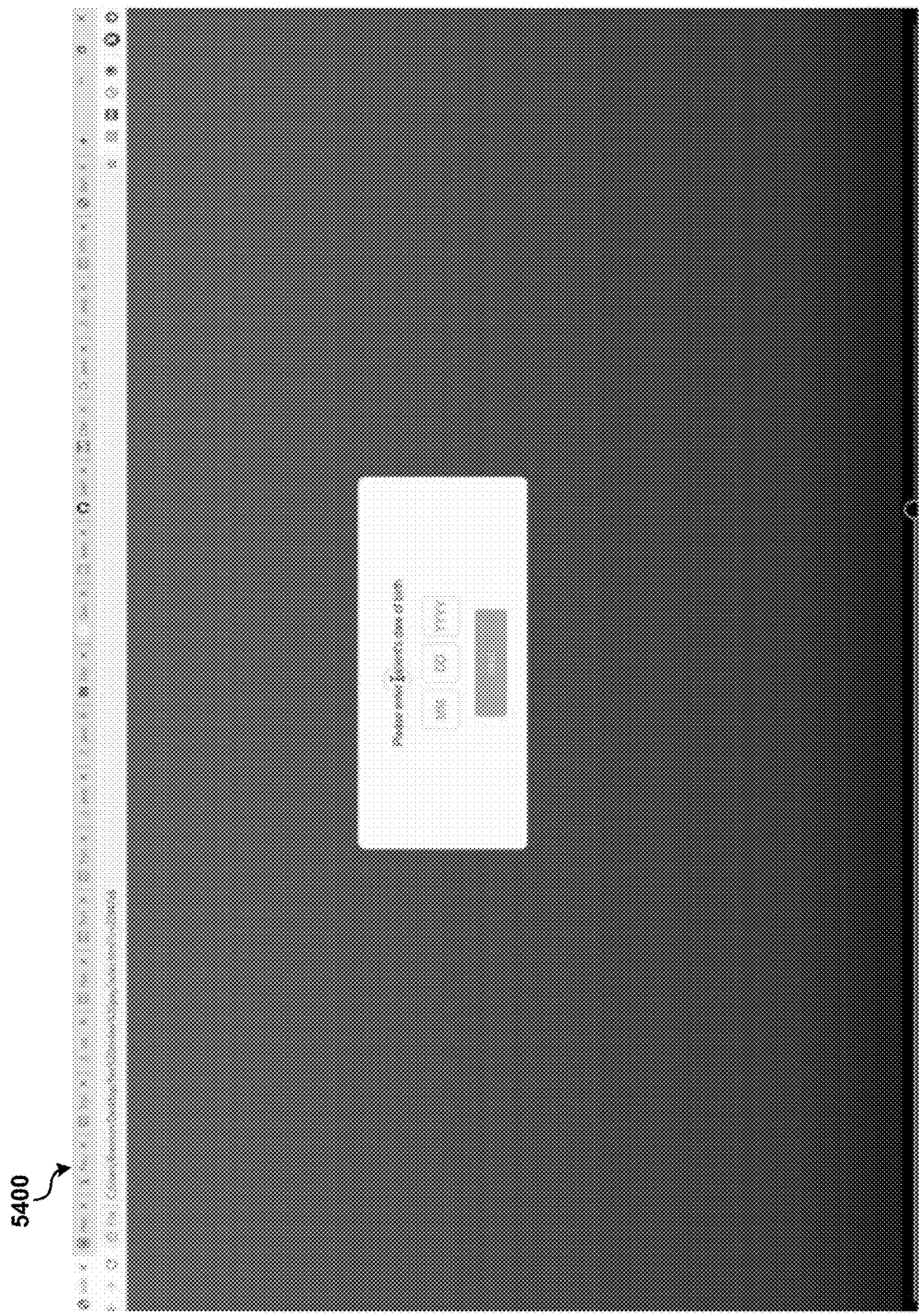
Figure 55:
Figure 56:
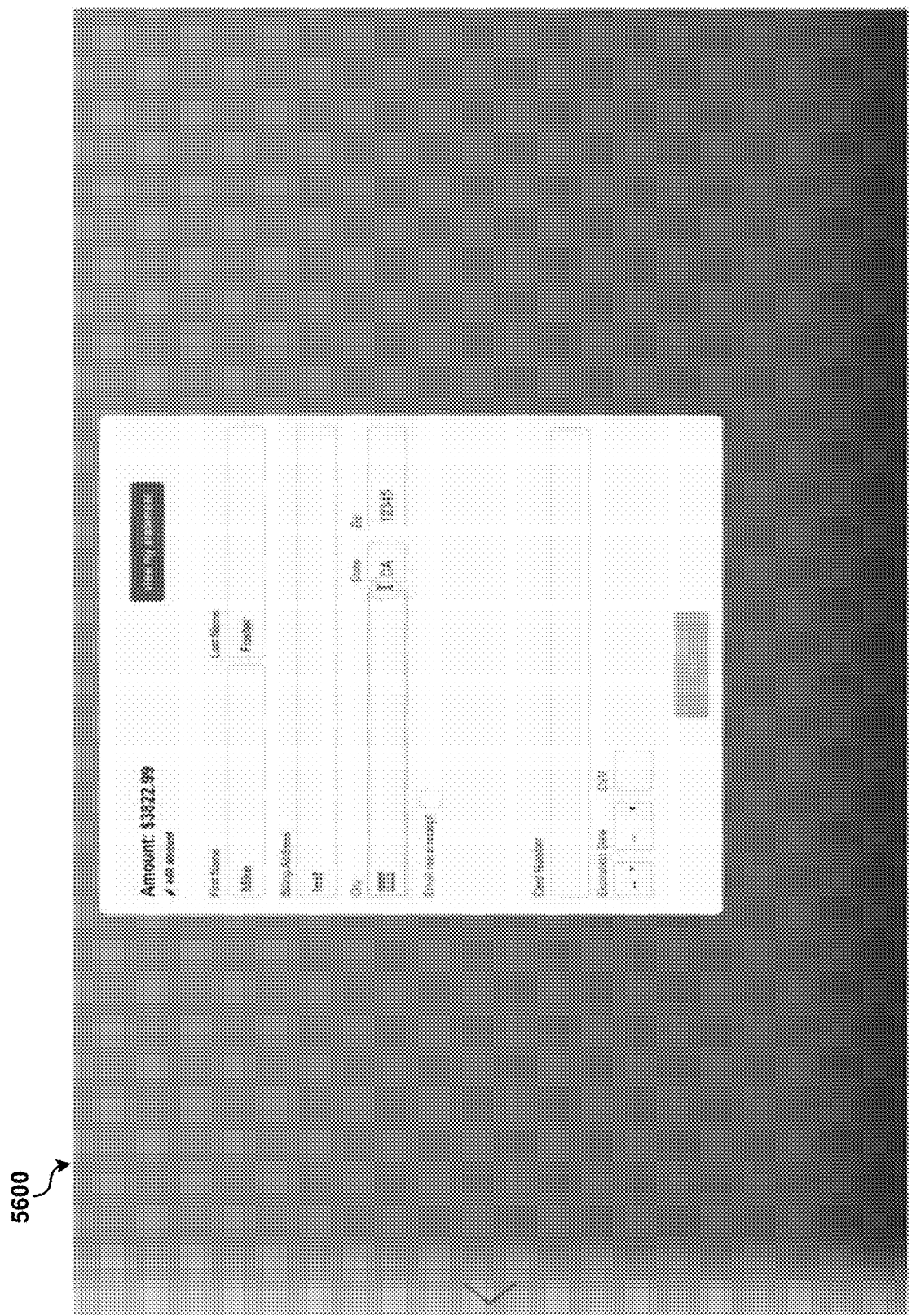
Figure 57:
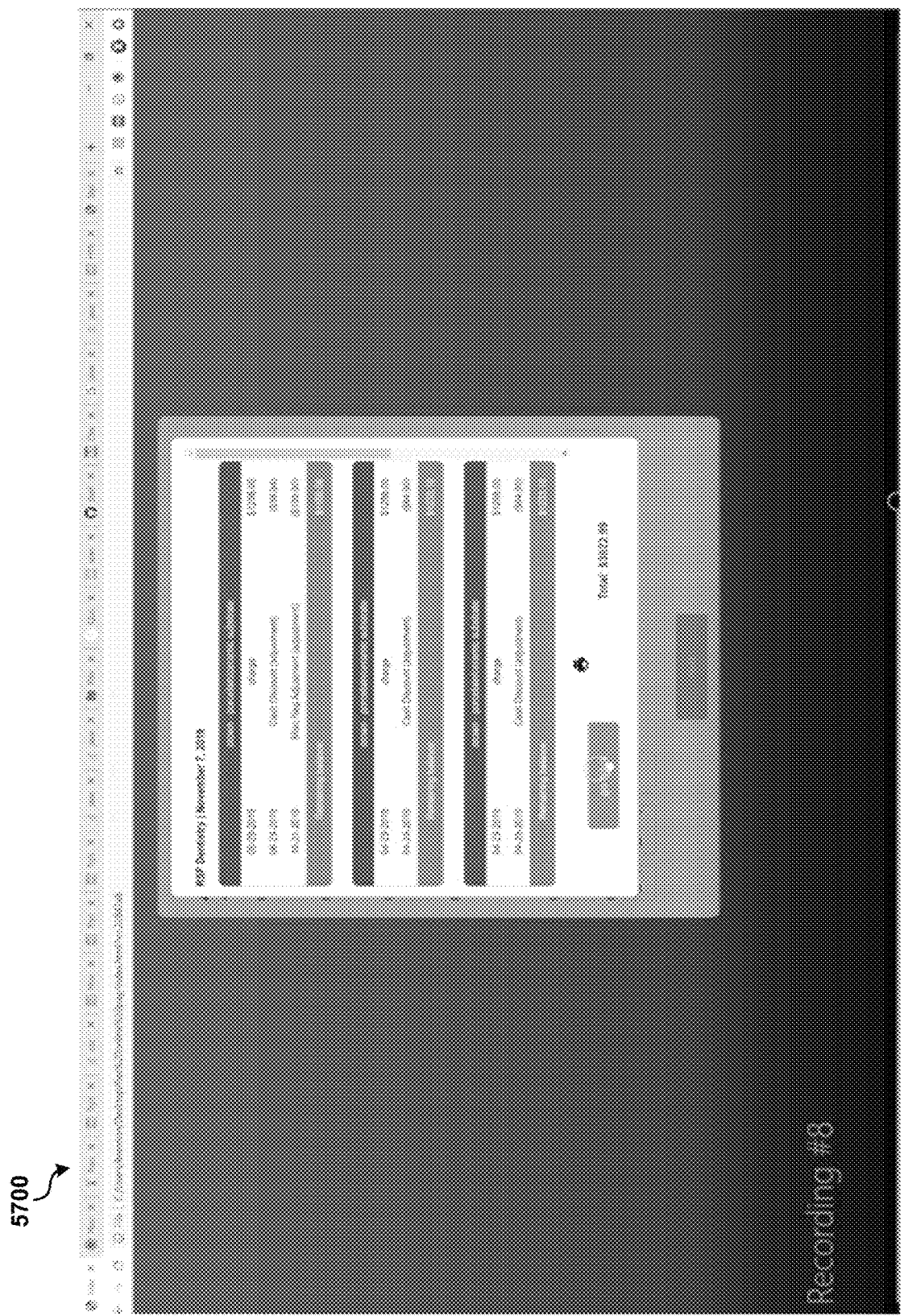
Figure 58:
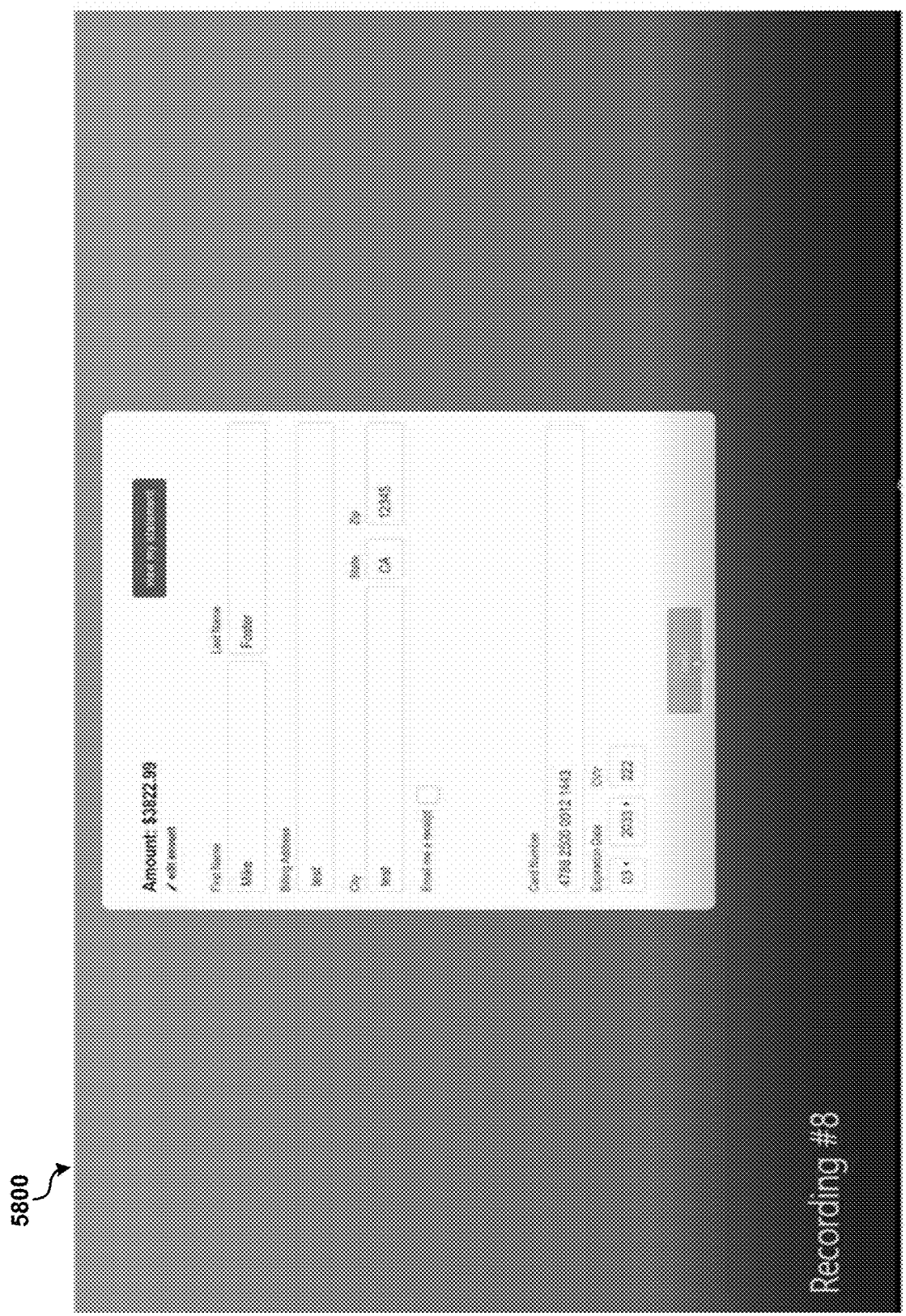
Figure 59:
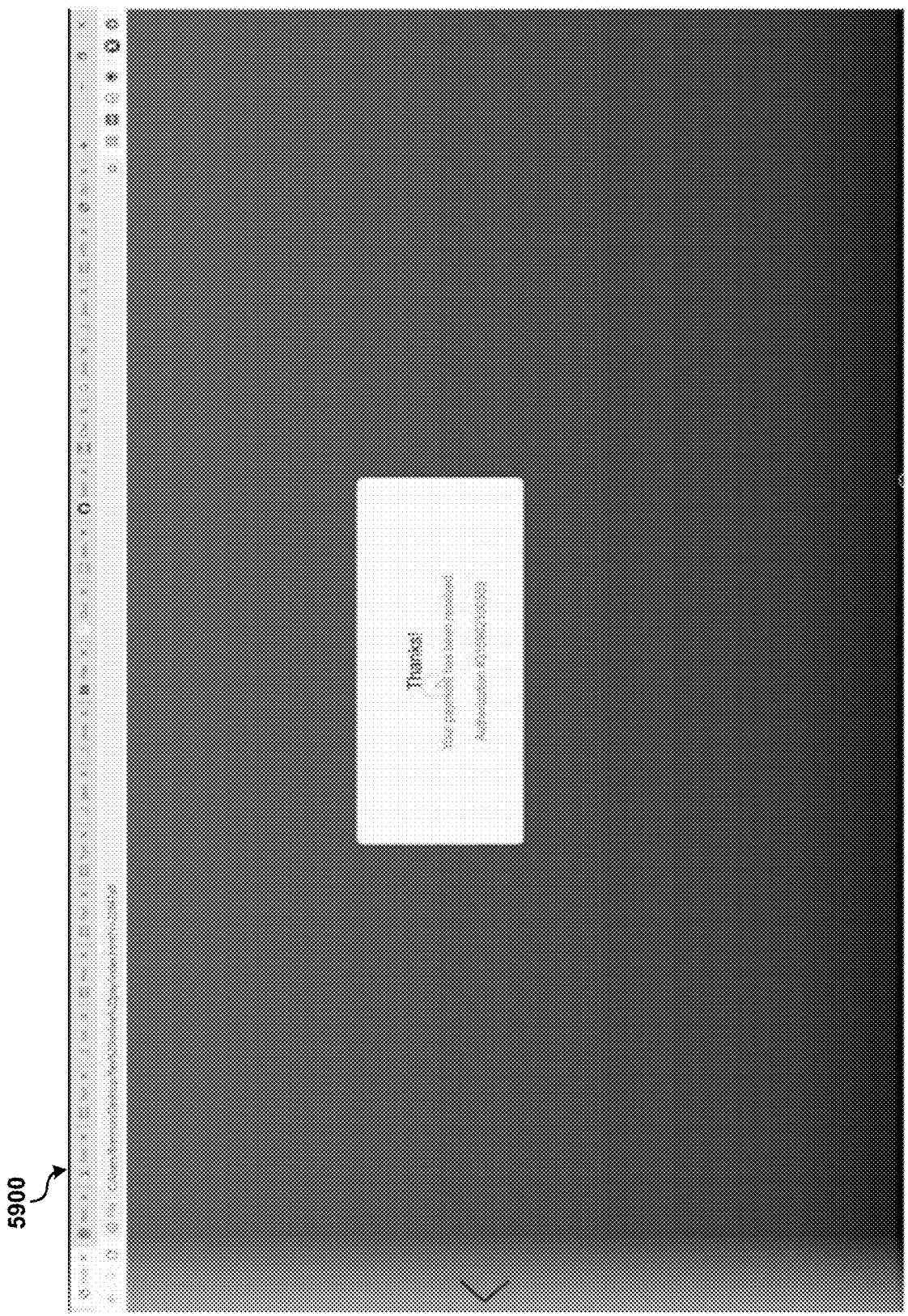
Figure 60:
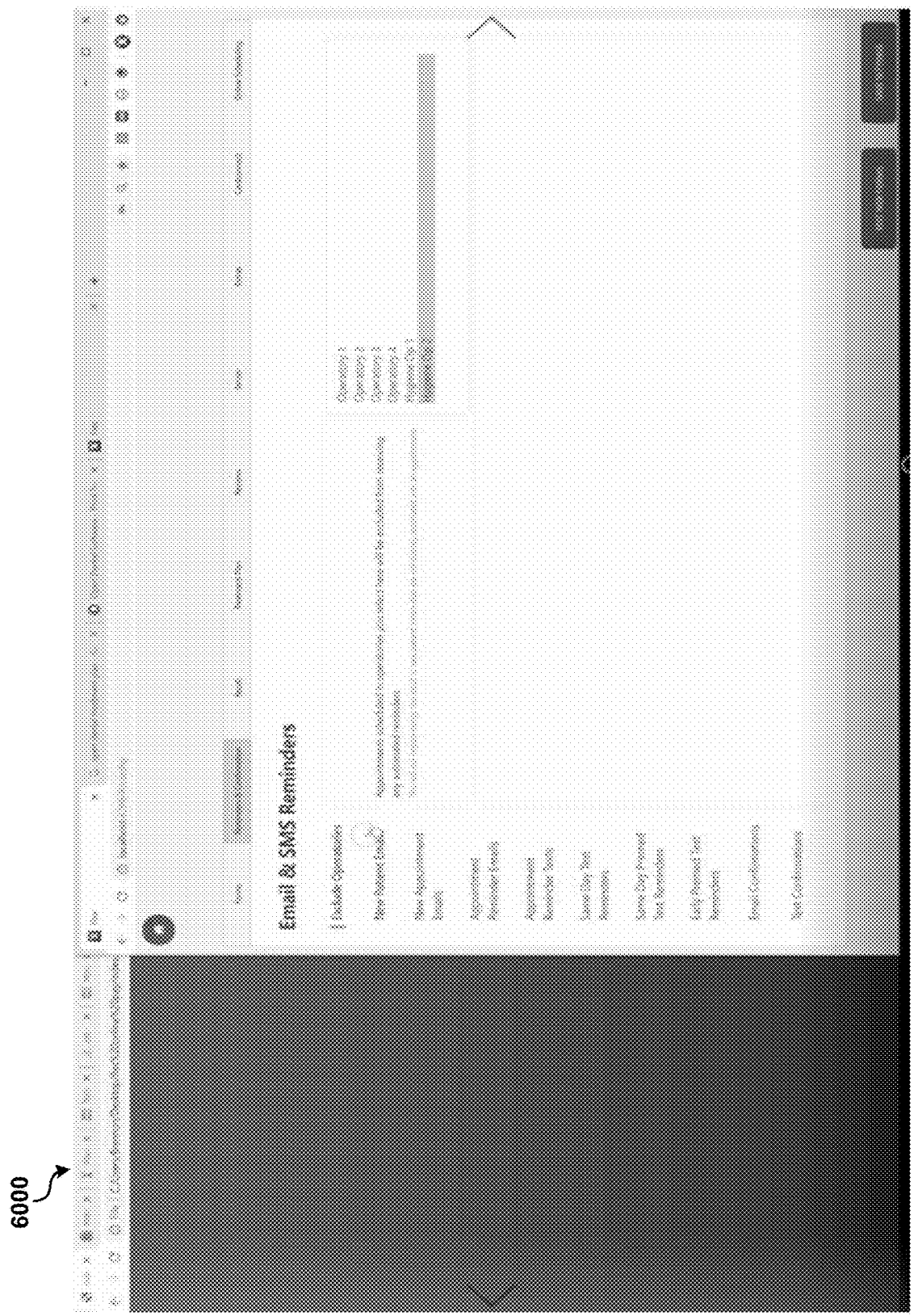
FIGS. 60-61 illustrate examples of displayed screens from the web-based platform associated with an implemented email and short messaging system (SMS) reminder feature, according to one or more embodiments shown and described herein.
Figure 61:
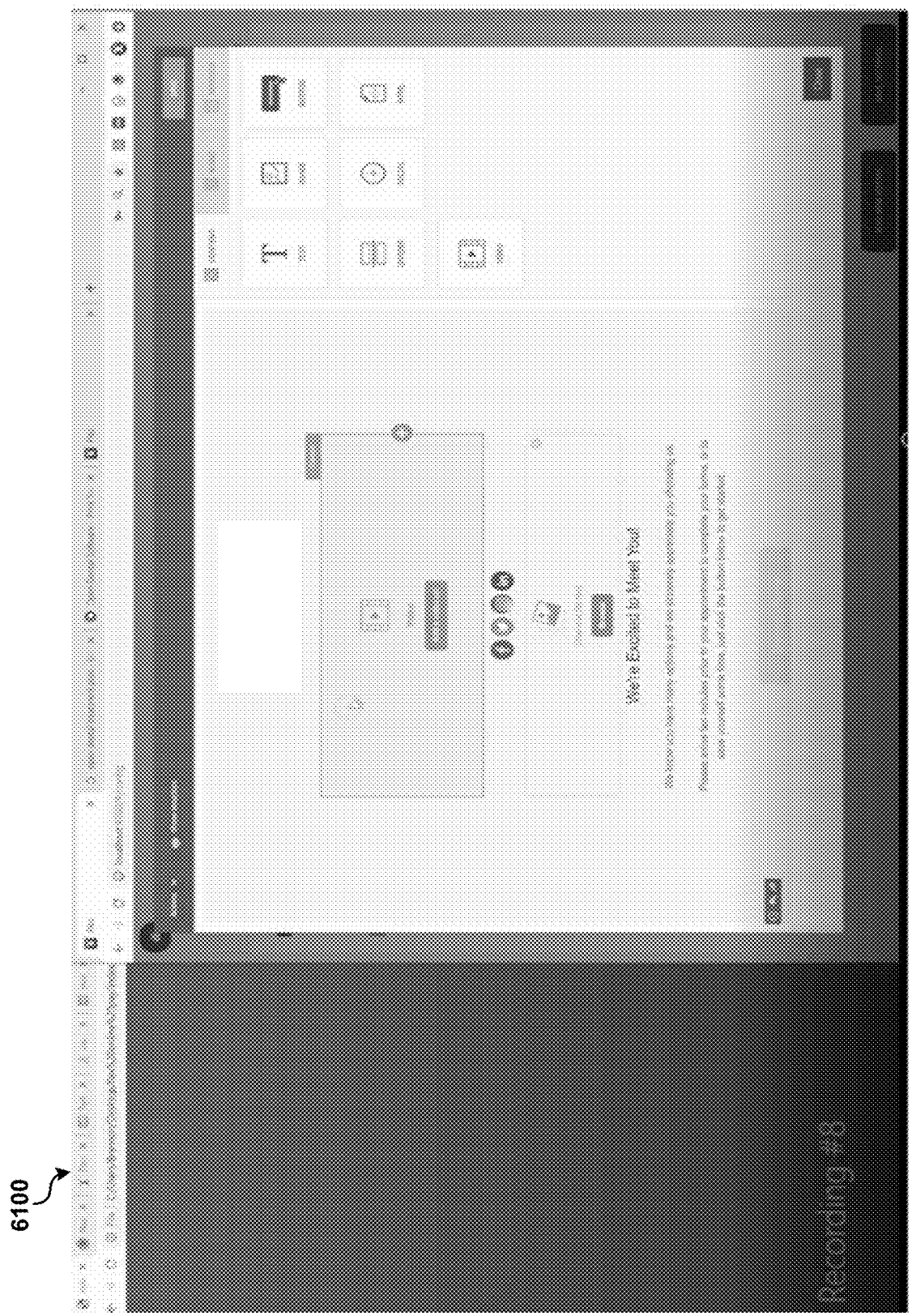
Figure 62:
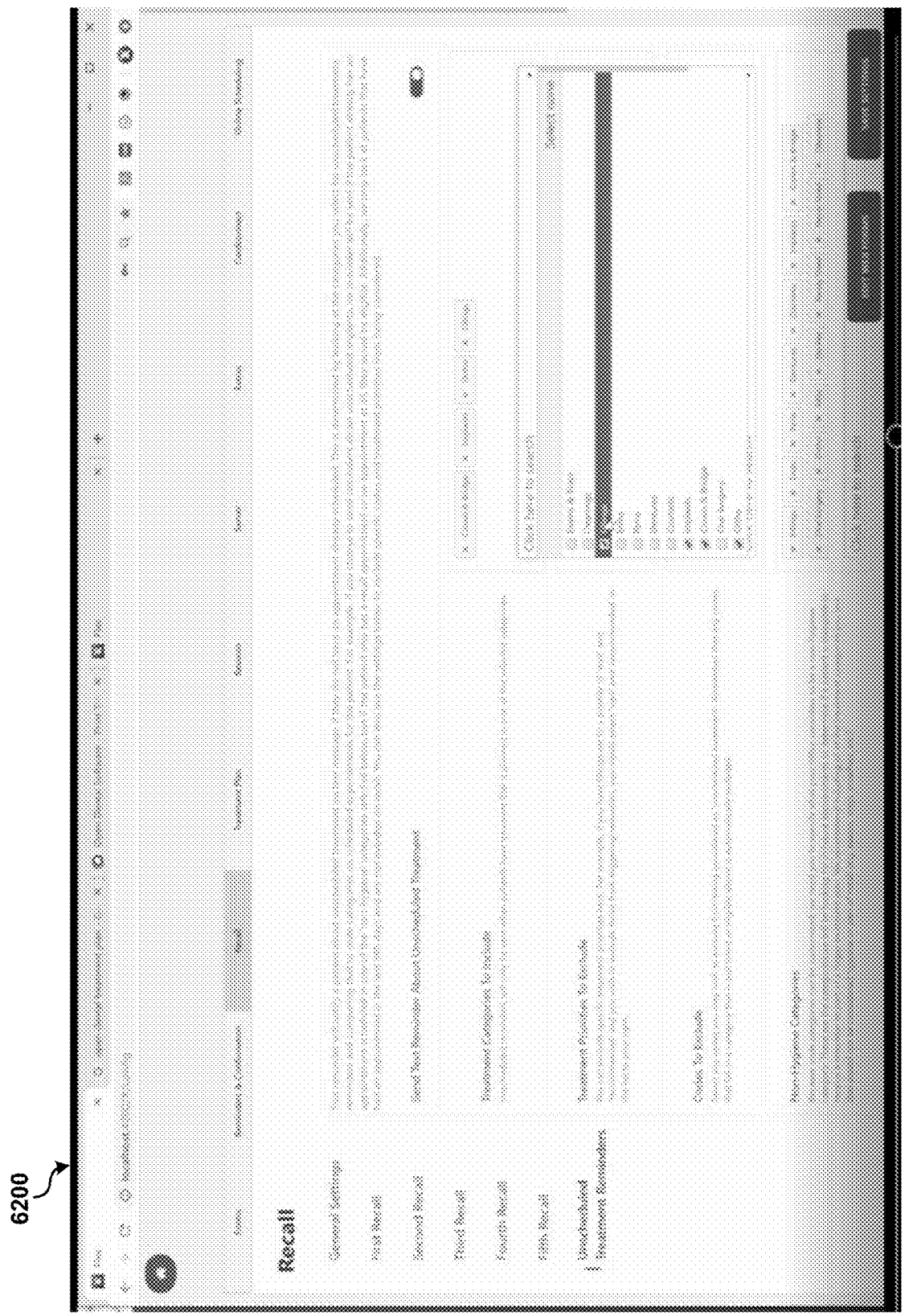
FIGS. 62-63 illustrate examples of displayed screens from the web-based platform associated with an implemented unscheduled treatment reminders feature, according to one or more embodiments shown and described herein.
Figure 63:
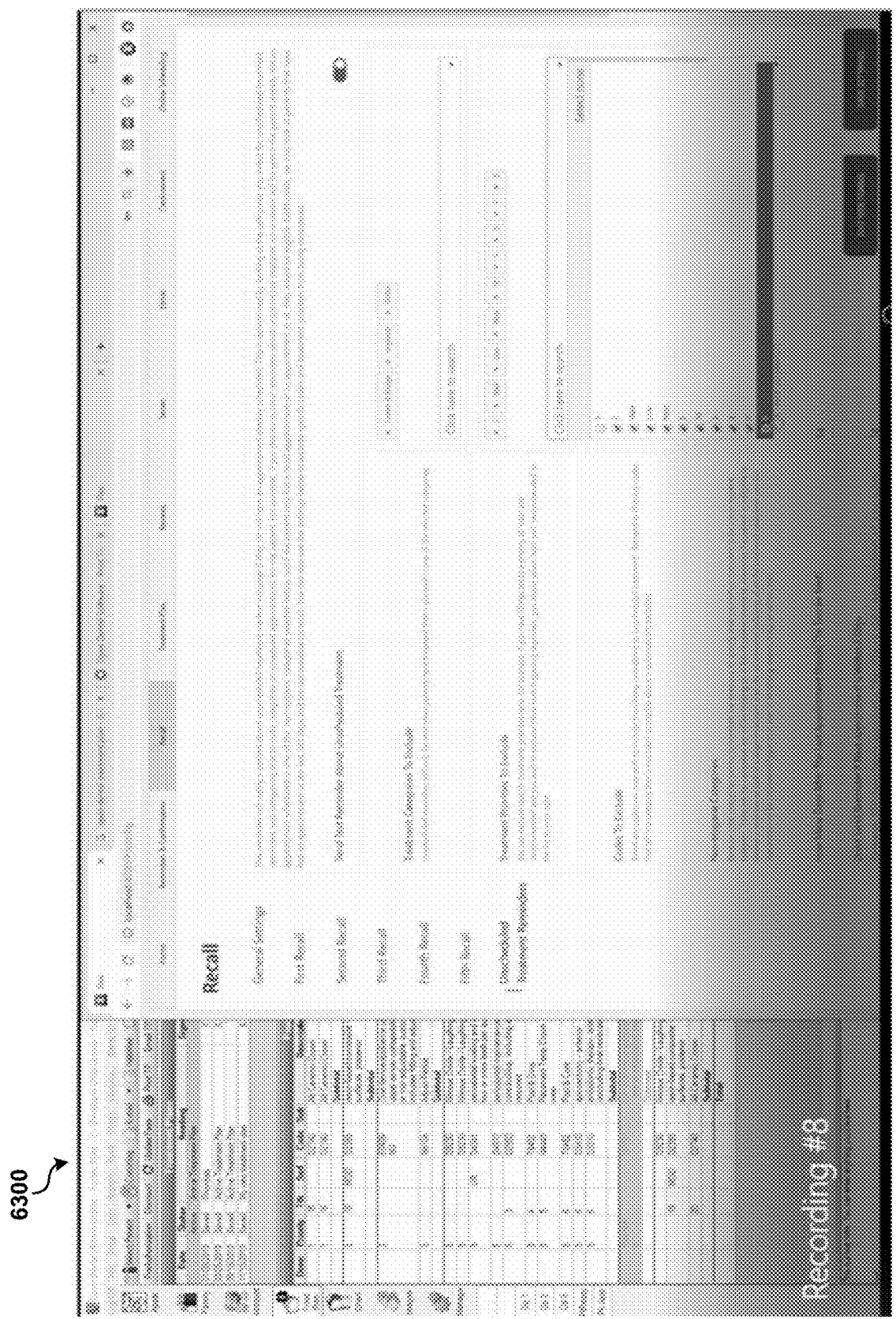

In FIG. 49, an example of a screen 4900 is shown displaying a tooth, related procedure, and a total cost related to a treatment plan. Now, referring to FIG. 50-59, examples of screens that may be displayed related to the send statement options are depicted. The send statement features allow a statement, corresponding to the dynamic treatment plan (in accordance with the payment options) to be electronically communicated to the patient. In some cases, the send statement can use email or SMS messaging. FIG. 50 depicts a screen 5000 displaying a selection to send a statement to a patient. FIG. 51 depicts a screen 5100 displaying a statement, including various payment plan charges and payment plan credits. FIG. 52 depicts a screen 5200 displaying a selection to text a statement to a patient. FIG. 53 depicts an example of a screen 5300 that can be used to compose a text message to be sent to a patient relating to the statement. FIG. 54 depicts an example of a screen 5400 that can be used to enter a patient's date of birth. FIG. 55 depicts an example of a screen 5500, and FIG. 56 depicts an example of a screen 5600, where both screens 5500, 5600 can be used to enter a patient's billing address and card number. FIG. 57 depicts a screen 5700 displaying a statement for a patient. FIG. 58 depicts another example of a screen 5800 that can be used to enter a patient's billing address and card number. FIG. 59 depicts a screen 5900 displaying a notification that payment has been received. FIGS. 60-61 show examples of screens that may be displayed related to the email and SMS reminder features, which can send automated reminders of appointment (and treatments) to users. FIG. 60 depicts an example of a screen 6000 that can be used for configuring email and SMS reminders for scheduled appointments. FIG. 61 depicts an example of a screen 6100 providing information for an appointment. Similarly, FIGS. 62-63 show examples of screens that may be displayed for the reminder features of the web-based platform, which sends automated reminders of appointment (and treatments) to users. However, these reminders are focused on procedures that may be planned for the patient, but not yet scheduled by the patient. The automated patient communication features of the web-based platform, including the reminder SMS and e-mails reminders, can be edited, controlled, and configured using the web-based platform. For example, a dental office employee can edit an e-mail to include particular contents of the message and select a time and/or frequency of when the message will be automatically sent to the patient. The automated patient communication features of the web-based platform can include, but is not limited to: sending fully customized confirmation texts that auto update PMS; automated new patient message, including URL links to complete forms; recall overdue patients (e.g., including scheduling); automated reminders for planned treatments that remain unscheduled; automated reminders to pre-medicate before an appointment; and automated patient courtesy messages (e.g., birthday greetings with images, videos, GIFs, and the like). FIG. 62 depicts an example of a screen 6200 that can be used for configuring recall reminders, where recall reminders notify patients about an unscheduled treatment. FIG. 63 depicts an example of a screen 6300 that can be used for configuring recall reminders, displaying treatment codes that can be selected to be excluded from being considered as unscheduled treatments. A mass messaging feature may be supported by the web-based platform as an additional automated patient communication feature. For example, the web-based platform can be employed to generate a mass e-mail (or SMS, text, MMS message) that is automatically communicated across the dental's office patient base, such that important information is disseminated in an automated and wide-spread manner. In some embodiments, the web-based platform provides templates that can be easily edited in order to create a mass message. Alternatively, a mass message may be completely created by a user (without using a template). Patient filters can be applied to a mass message in a manner that allows mass message be sent to a particularly selected group of recipients. For example, a mass e-mail may be targeted to patients deemed most appropriate for the message by creating a group based on patient properties (e.g., insurance status, completed procedure codes, upcoming appointment, treatment planned procedures, and other key data points).

Figure 64:
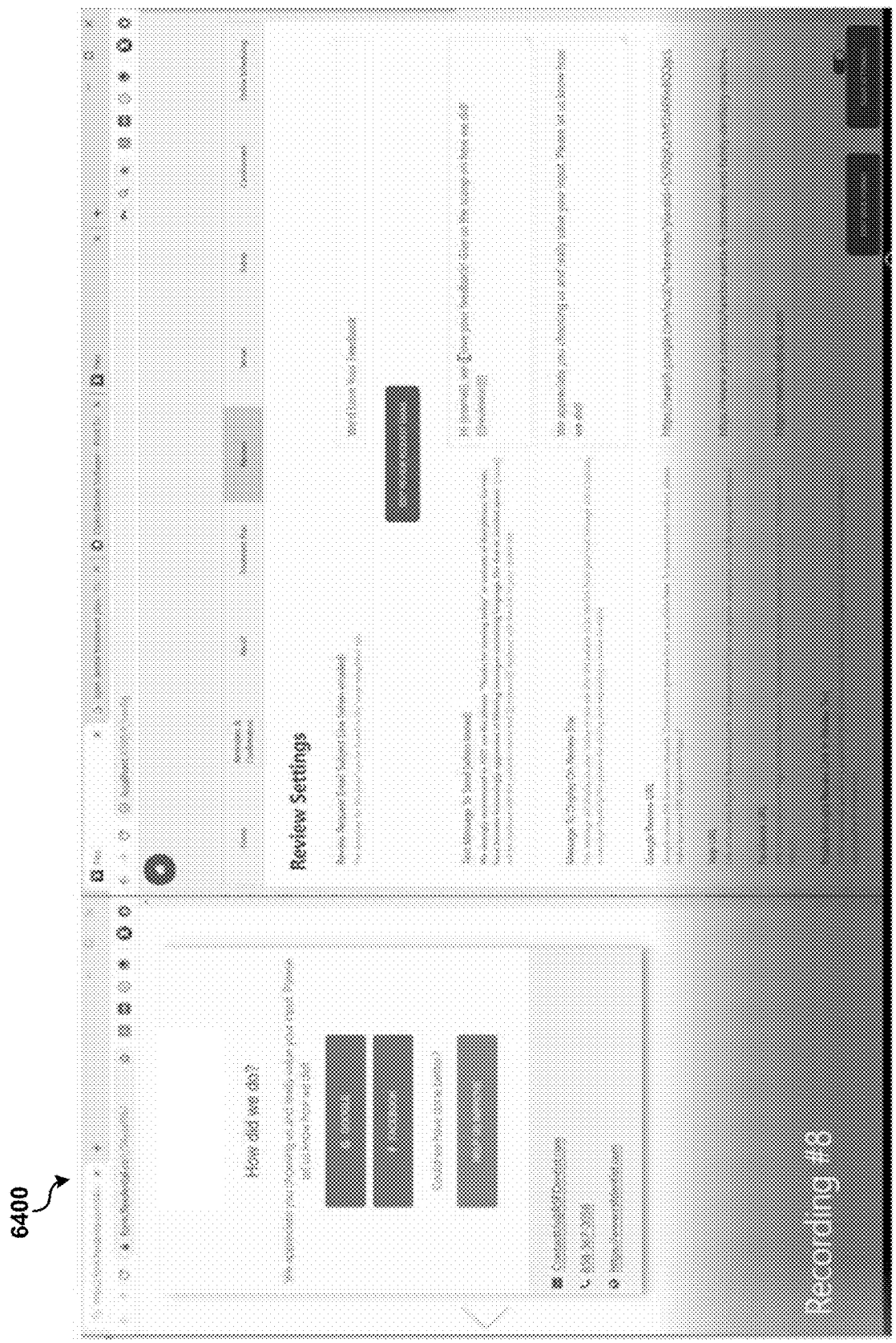
FIGS. 64-65 illustrate examples of displayed screens from the web-based platform associated with an implemented patient review feature, according to one or more embodiments shown and described herein.
Figure 65:
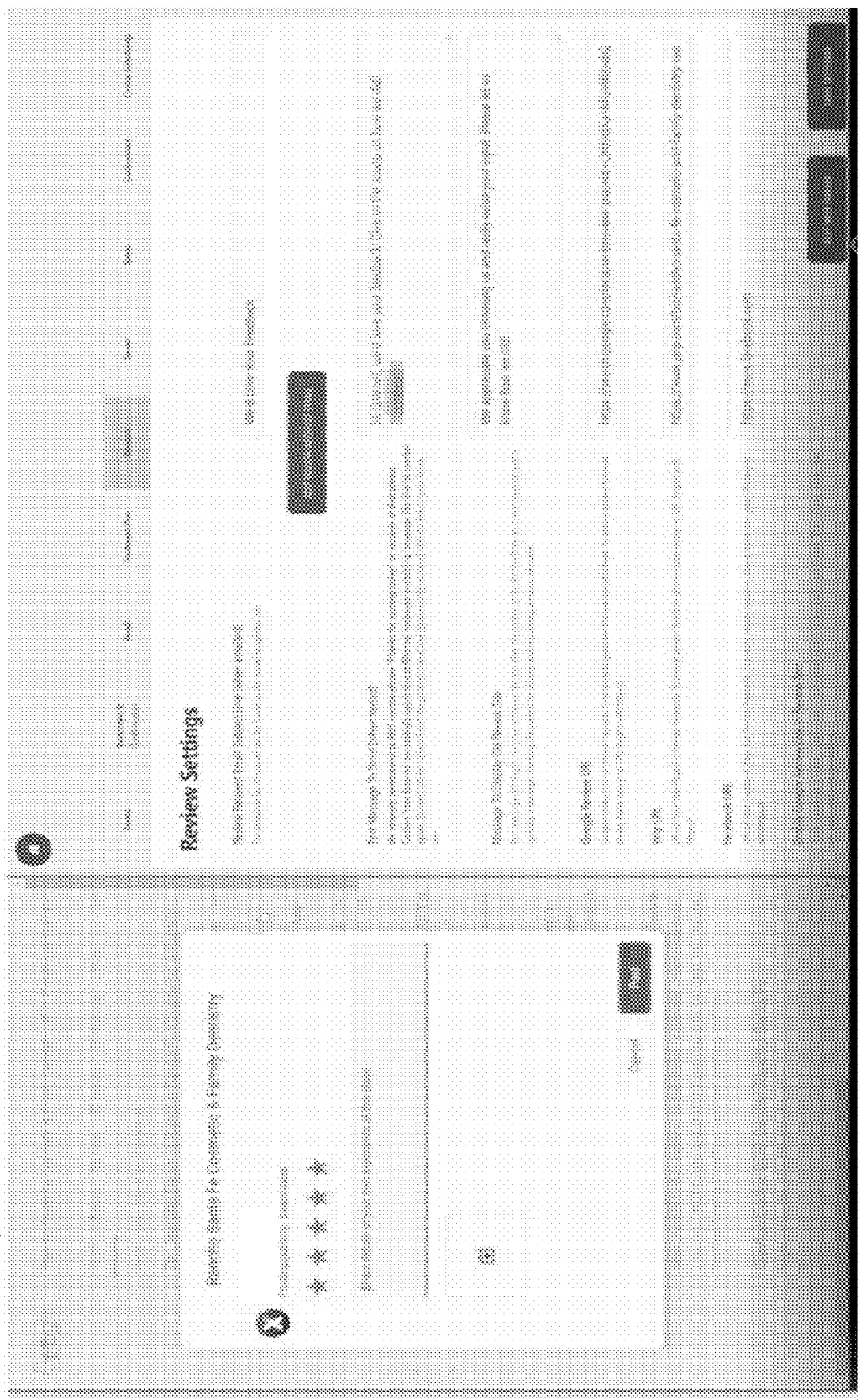

In FIG. 64-65, examples of screens that may be displayed related to patient review features of the web-based platform are shown. That is, when an appointment is completed the patient review feature can send an automated reminder to the patient, prompting them to write a review of the experience at the dental office. In some cases, the reminder is an email that includes a link to a commonly used review platform, such as Facebook, Google, and the like. FIG. 64 depicts an example of a screen 6400 that can be used for entering review settings, such as settings for review request emails. FIG. 65 depicts an example of a screen 6500 that can be used for editing a review request email.

Figure 66:
FIGS. 66-68 illustrate examples of displayed screens from the web-based platform associated with an implemented on-line appointment scheduling feature, according to one or more embodiments shown and described herein.
Figure 67:
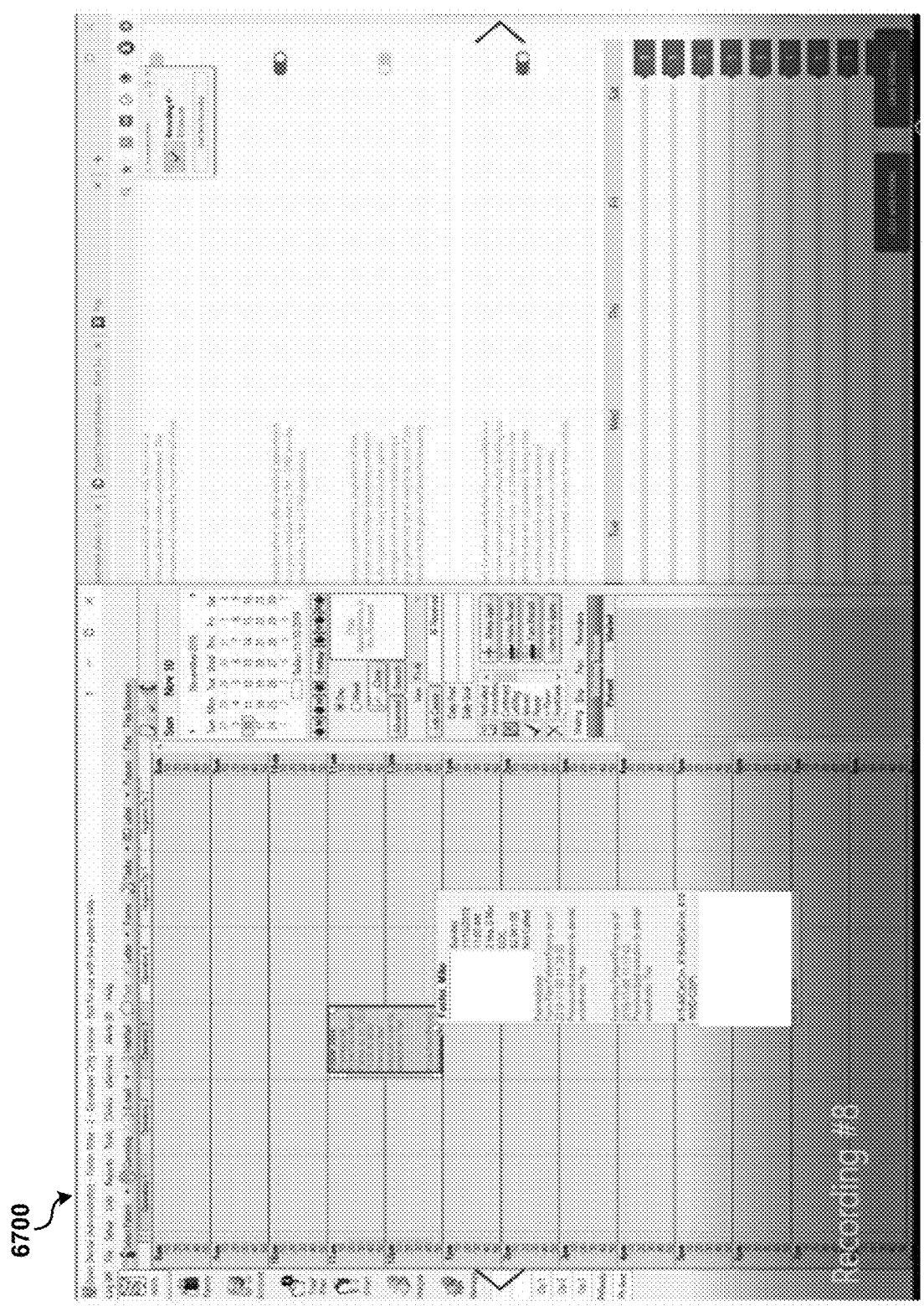
Figure 68:
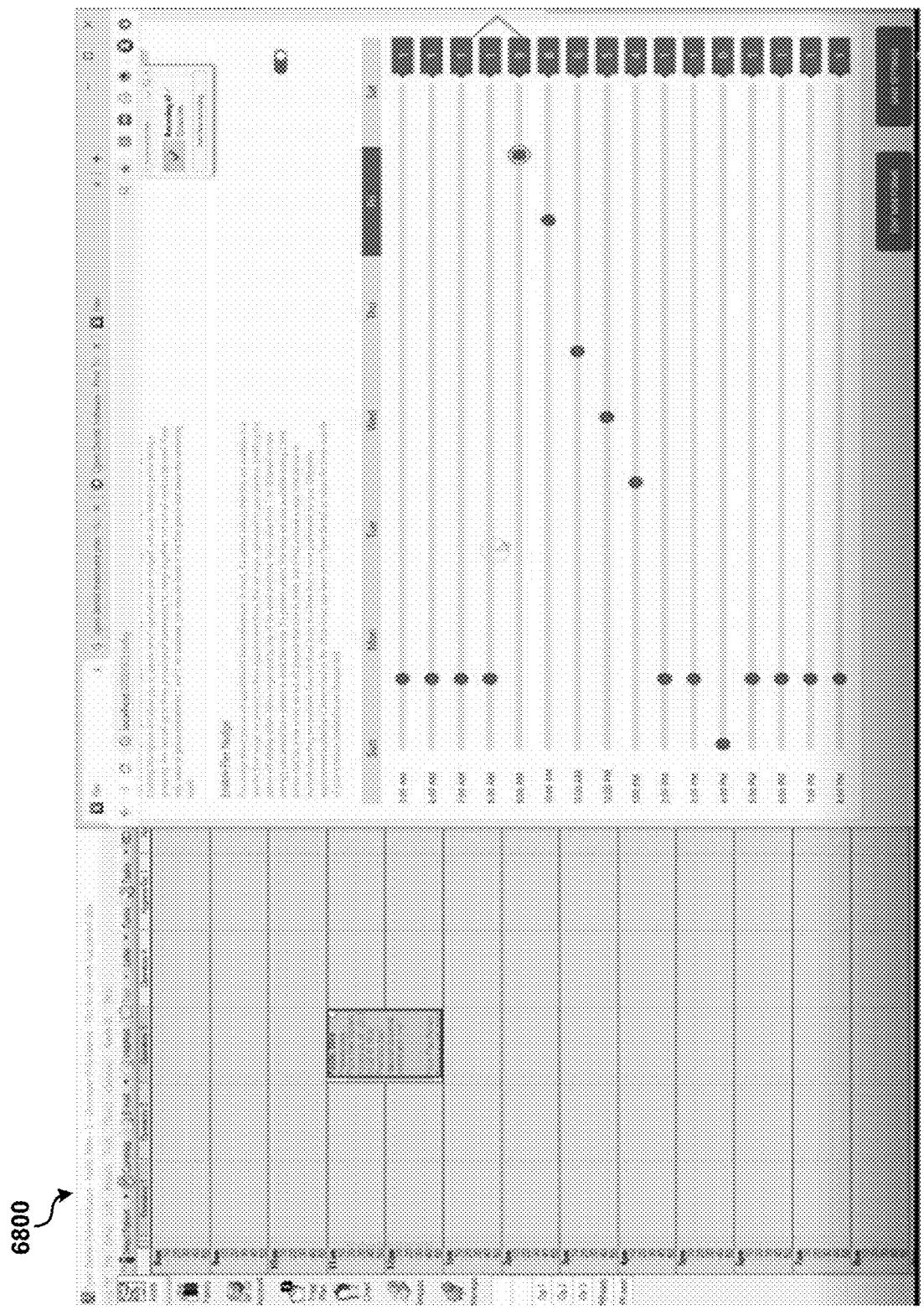

In FIGS. 66-68, examples of screens that may be displayed related to on-line appointment scheduling features of the web-based platform are shown. According to some embodiments, the on-line scheduling features include schedule intelligence functions, such as nudge and cluster, which can manage appointments that are scheduled on-line in a manner that optimizes efficiency, meets doctor preferences, while being ideal for the dental practice and the patient. FIG. 66 depicts an example of a screen 6600 displaying various intelligent scheduling options, including appointment clustering, merge operatories, and flex nudge. FIG. 67 depicts an example of a screen 6700 displaying an appointment for a patient that may be associated with the intelligent scheduling options. FIG. 68 depicts an example of a screen 6800 that can be used for setting appointment time preferences using the flex nudge feature of intelligent scheduling.

Figure 71:
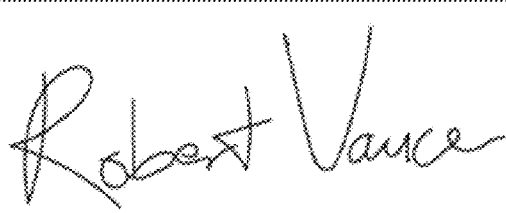
FIG. 71 depicts an example of a treatment plan including payment options that may be generated by the web-based platform as displayed on a patient device (e.g., via SMS message or e-mail), according to one or more embodiments shown and described herein.

In FIG. 71, an example of a dynamic form, namely a treatment plan including payment options that may be generated by the web-based platform, as displayed on a patient device, as shown. In the example of FIG. 71, multiple payment options (shown as "Pay In Advance", "Payment Plan", "No Interest Financing") may be displayed to the patient allowing them to select which payment option is desired. Under each payment options is a short description, such as discounts, fee, payment terms, that correspond to each payment option so that the patient can make an informed decision using the information displayed. It should be understood that the payment options that are displayed to the patient in FIG. 71 are the options that have been previously selected by the dental office as being available for that particular patient. Subsequently, the patient can select the desired payment option, and provide their signature from this screen on their patient device. For example, the patient may use a touchscreen on their laptop computer to enter their signature which is captured by the form in FIG. 71. Even further, FIG. 71 shows that the patient can select to return the completed and signed treatment plan (including the selected payment option) back to their dental office via e-mail or text message.

Figure 70:
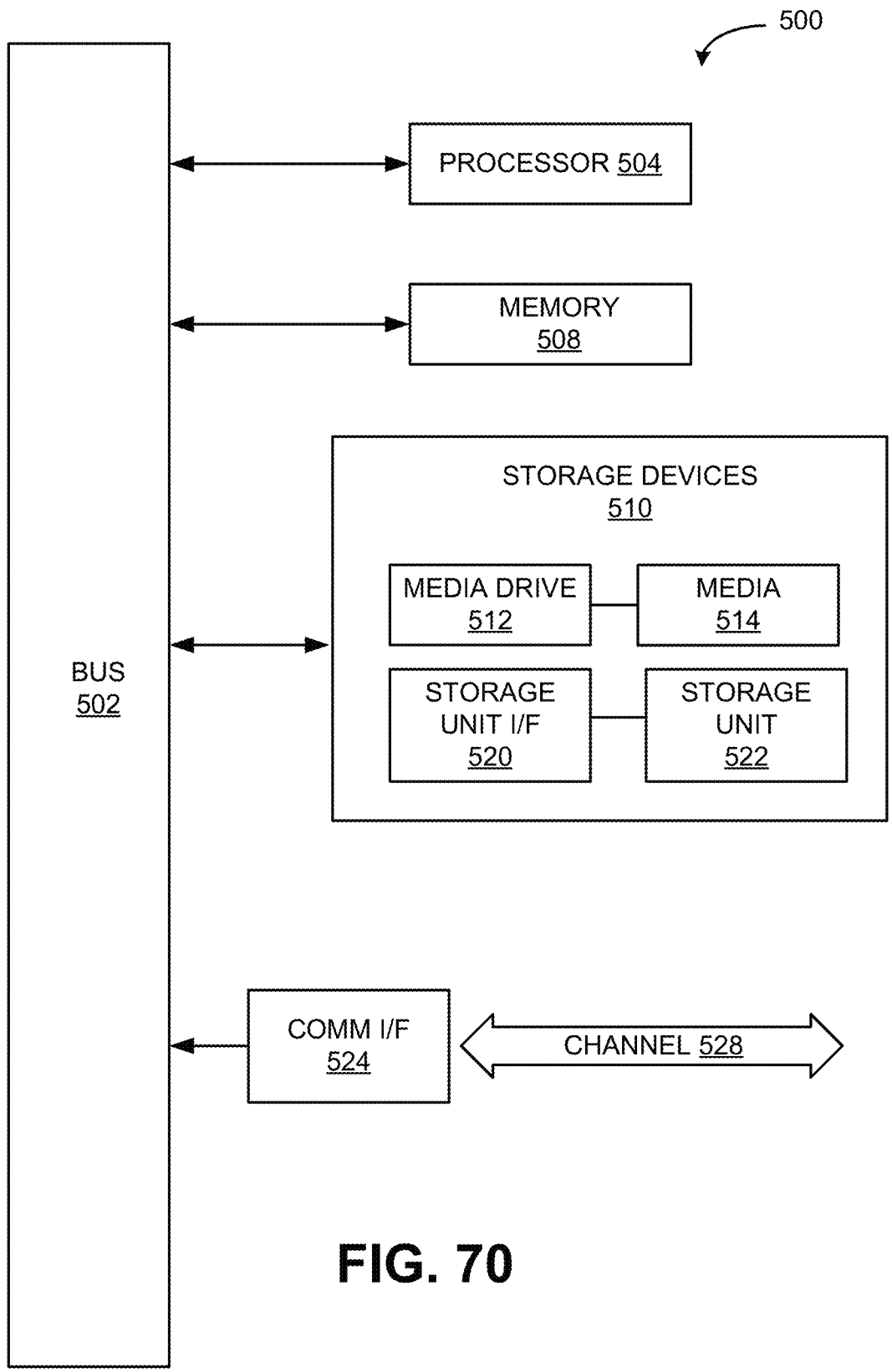
FIG. 70 depicts an example of a computing component that may be used in implementing various features of embodiments of the disclosed technology.

Referring now to FIG. 70, computing module 500 may represent, for example, computing or processing capabilities found within desktop, laptop, notebook, and tablet computers; hand-held computing devices (tablets, PDA's, smart phones, cell phones, palmtops, etc.); mainframes, supercomputers, workstations or servers; or any other type of special-purpose or general-purpose computing devices as may be desirable or appropriate for a given application or environment. For example, a computing module might be found in other electronic devices such as, for example, digital cameras, navigation systems, cellular telephones, portable computing devices, modems, routers, WAPs, terminals and other electronic devices that might include some form of processing capability.

Computing module 500 might include, for example, one or more processors, controllers, control modules, or other processing devices, such as a processor 504. Processor 504 might be implemented using a general-purpose or special-purpose processing engine such as, for example, a microprocessor, controller, or other control logic. In the illustrated example, processor 504 is connected to a bus 502, although any communication medium can be used to facilitate interaction with other components of computing module 500 or to communicate externally.

Computing module 500 might also include one or more memory modules, simply referred to herein as main memory 508. For example, preferably random-access memory (RAM) or other dynamic memory, might be used for storing information and instructions to be executed by processor 504. Main memory 508 might also be used for storing temporary variables or other intermediate information during execution of instructions to be executed by processor 504. Computing module 500 might likewise include a read only memory ("ROM") or other static storage device coupled to bus 502 for storing static information and instructions for processor 504.

The computing module 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a solid state drive, a magnetic tape drive, an optical disk drive, a CD or DVD drive (R or RW), or other removable or fixed media drive might be provided. Accordingly, storage media 514 might include, for example, a hard disk, a solid-state drive, magnetic tape, cartridge, optical disk, a CD or DVD, or other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing module 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory module) and memory slot, a PCMCIA slot and card, and other fixed or removable storage units 522 and interfaces 520 that allow software and data to be transferred from the storage unit 522 to computing module 500.

Computing module 500 might also include a communications interface 524. Communications interface 524 might be used to allow software and data to be transferred between computing module 500 and external devices. Examples of communications interface 524 might include a modem or soft modem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 524 might typically be carried on signals, which can be electronic, electromagnetic (which includes optical) or other signals capable of being exchanged by a given communications interface 524. These signals might be provided to communications interface 524 via a channel 528. This channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer readable medium", "computer usable medium" and "computer program medium" are used to generally refer to non-transitory media, volatile or non-volatile, such as, for example, memory 508, storage unit 520, media 514, and transitory channels 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 500 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

What is claimed is:

1. A web-based platform system, comprising:
   a practice management system (PMS);
   a first computer device, wherein the first computer device is associated with a patient; and
   a second computer device communicatively connected to the PMS and to the first computer device via a distributed network, wherein the second computer device is associated with a medical office and is programmed to:
   create a token that corresponds to the patient associated with the first device, wherein the token comprises a digital object identifying the patient associated with the first device; and
   pass the token to the PMS to be stored such that the token is linked to records corresponding to the patient being stored on the PMS;
   create a treatment plan corresponding to the patient and linked to the token;
   dynamically adjust the treatment plan based on selections entered into the second device linked to the token and based on data received from the first device using the token;
   create one or more payment options corresponding to the treatment plan, wherein creating the one or more payment options comprises dynamically adjusting the one or more payment options based on additional selections entered into the second device and based on additional data received from the first device; and
   synchronize the created treatment plan and the created one or more payment options with the PMS in real-time using the token such that the treatment plan and data associated with the patient is exchanged between the PMS and the first computer device to pass-thru in a transient manner, the PMS using the token to link the created treatment plan and the created one or more payment options to the records corresponding to the patient stored on the PMS.

2. The web-based platform system of claim 1, wherein the distributed network is the Internet.

3. The web-based platform system of claim 1, wherein the second computer device is further programmed to:
   control scheduling of dental appointments for each of a plurality of patients, including the patient associated with the first computer device;
   control planning of charts and treatments associated with the medical plan for each of the plurality of patients, including the patient associated with the first device; and
   control accounting and financial data associated with the dental appointments and the medical plan for each of a plurality of patients, including the patient associated with the first computer devices.

4. The web-based platform system of claim 1, wherein the second computing device is further programmed to:
   receive new patient data from the first device, wherein the new patient data is associated with a new dental appointment and including data not stored in the PMS; and
   synchronizing the new patient data with the PMS in real-time such that the new patient data is stored in the PMS.

5. The web-based platform system of claim 1, wherein the second computer device is further programmed to:
   dynamically generate one or more dynamic forms that are accessible by the first computer device via the distributed network;
   automatically transmit the one or more dynamic forms to the first computer device; and
   in response to receiving the one or more dynamic forms from the first computer device including updated data entered by the patient, automatically transmit the one or more dynamic forms to the PMS such that the updated data from the one or more dynamic forms is synchronized with PMS.

6. The web-based platform system of claim 5, wherein the one or more dynamic forms comprise at least one of: patient intake forms, consent forms, dental plans, and statement forms.

7. The web-based platform system of claim 6, wherein the second computer device is further programmed to:
   generate a plurality of procedure codes, wherein each of the plurality of procedure codes indicates a medical procedure and corresponds to a respective consent form for the medical procedure;
   link at least one of the plurality of procedure codes to the treatment plan to automatically link the consent form corresponding to the procedure code to the treatment plan for the patient;
   generate a universal resource locator (URL) that is associated with the patient, wherein clicking the URL at the first device automatically accesses the treatment plan for the patient, dynamic forms for the patient, and the linked consent forms; and
   transmit an automated message to the first device having the URL embedded therein, wherein the automatic message comprises an electronic mail (e-mail) or short messaging service (SMS) message.

8. The web-based platform system of claim 5, wherein dynamically generating each of the one or more dynamic forms comprises modifying content included in each of the forms based on data that is particularly associated with the patient in a manner that customizes the one or more dynamic forms for the patient.

9. The web-based platform system of claim 7, wherein dynamically adjusting the one or more payment options comprises modifying the payment options based on the additional data that is entered in to the second device and patient data from the PMS that is associated with the patient in a manner that omits at least one payment option that does not meet a criteria corresponding to the patient.

10. The web-based platform system of claim 9, wherein the second computer device is further programmed to:
    receive an electronic payment from the first device, wherein the electronic payment is entered into the first device via the accessed treatment plan corresponding with the patient; and
    in response to successfully processing the electronic payment, synchronize electronic payment with the PMS.

11. The web-based platform system of claim 10, wherein the at least one omitted payment option comprises: down payment, payment length term, management fees, discount, and discount amount.

12. The web-based platform system of claim 10, wherein the second computer device is further programmed to:
    associate the token with the URL transmitted within the automated message to the first device.

13. The web-based platform system of claim 10, wherein second computer device is further programmed to:
    determine the records that are stored on the PMS that are linked to the token and the identified patient; and
    dynamically load data from the determine records into the treatment plan for the patient, dynamic forms for the patient, and the linked consent forms such that the treatment plan is presented on the first computer device including the data loaded from the PMS that is specific to the patient corresponding to the token pre-populated in the treatment plan.

14. The web-based platform system of claim 13, wherein the second device is programmed to:
    validate the token transmitted to the first device.

15. The web-based platform system of claim 1, wherein the treatment plan is a dental plan, the patient is a dental patient, and the patient device is a mobile device.

16. A method, comprising:
    creating, by an application backend, a token associated with a patient, wherein the token comprises a series of characters that are automatically generated by the application backend and stored in a system such that the token corresponds to records for the patient being stored on the system and links to the token to a treatment plan for the associated patient stored on the system;
    requesting, by the application backend, data associated with the treatment plan using the token, wherein the treatment plan and the data associated with the treatment plan are saved in the system and linked to the token such that data associated with the treatment plan linked to the token automatically populates in a graphical user interface;
    receiving, by an application frontend, the token and the data associated with the treatment plan;
    querying the application backend for predefined payment options;
    determining, by the application frontend, whether a patient is eligible for one or more payment options corresponding to the treatment plan based on information for the patient saved in the system linked to the token and parameters associated with the predefined payment options, wherein the one or more payment options corresponding to the treatment plan are from the predefined payment options; and
    in response to determining that the patient is eligible for the one or more payment options corresponding to the treatment plan,
    loading, by the application frontend, the one or more payment options corresponding to the treatment plan linked to the token to present to the patient, wherein the data associated with the treatment plan and the loaded payment options are presented via the graphical user interface;
    dynamically modifying, by the application frontend, the one or more payment options corresponding to the treatment plan in real-time to present to the patient and based on the information for the patient saved in the system that is linked to the token; and
    modifying, by the application frontend, the one or more payments options based on edits entered at a dental office.

17. The method of claim 16, further comprising:
    receiving, by the application frontend, a selected payment option from the one or more payment options presented to the patient, and wherein the system is a practice management system (PMS).

18. The method of claim 17, wherein modifying the one or more payment options in real-time comprises: editing the one or more payment options; adding a new payment option to the one or more payment options; and removing a payment option from the one or more payment options.

19. The method of claim 17, further comprising:
    transmitting, by the application backend, a web-based form and the token to a patient device to submit a payment in accordance with the selected payment option, wherein the web-based form is linked to the token associated with the patient and receives financial data corresponding to the patient usable to process the payment.

20. The method of claim 19, further comprising:

processing, by the application backend, the payment submitted by the patient using the financial data in the web-based form; and storing a payment record associated with the payment at a practice management system using the token such that the payment record is stored corresponding to the records for the patient on the practice management system.

\* \* \* \* \*